United States Patent
Gibson et al.

(10) Patent No.: US 8,232,269 B2
(45) Date of Patent: Jul. 31, 2012

(54) AMIDE COMPOUNDS USEFUL IN THERAPY

(75) Inventors: Karl Richard Gibson, Sandwich (GB); Martin Peter Green, Sandwich (GB); Toby James Underwood, Sandwich (GB); Florian Wakenhut, Sandwich (GB)

(73) Assignee: Pfizer Inc., New York, NY (US)

( * ) Notice: Subject to any disclaimer, the term of this patent is extended or adjusted under 35 U.S.C. 154(b) by 235 days.

(21) Appl. No.: 12/561,398

(22) Filed: Sep. 17, 2009

(65) Prior Publication Data

US 2010/0249091 A1 Sep. 30, 2010

Related U.S. Application Data

(60) Provisional application No. 61/097,902, filed on Sep. 18, 2008.

(51) Int. Cl.
- *A61K 31/397* (2006.01)
- *A61K 31/415* (2006.01)
- *A61K 31/506* (2006.01)
- *A61K 31/4184* (2006.01)
- *A61K 31/454* (2006.01)
- *C07D 231/20* (2006.01)
- *C07D 205/04* (2006.01)
- *C07D 403/12* (2006.01)
- *C07D 235/02* (2006.01)
- *C07D 401/12* (2006.01)

(52) U.S. Cl. .......... 514/210.18; 514/210.2; 514/256; 514/326; 514/393; 514/406; 544/333; 546/211; 548/302.7; 548/364.1; 548/365.7; 548/374.1; 548/953

(58) Field of Classification Search .......... None
See application file for complete search history.

(56) References Cited

FOREIGN PATENT DOCUMENTS

WO WO 2006 111856 10/2006

*Primary Examiner* — Kamal Saeed
(74) *Attorney, Agent, or Firm* — Richard V. Zanzalari

(57) ABSTRACT

A compound of Formula (I), or a pharmaceutically acceptable salt or solvate thereof,

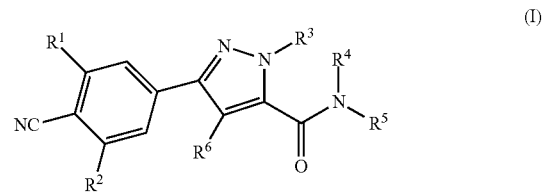

wherein, $R^1$ and $R^2$ each independently represent H, halogen, $CF_3$, $C_{1-3}$ alkyl or $C_{1-3}$ alkoxy;

$R^3$ represents $C_{1-6}$ alkyl, $C_{3-6}$ cycloalkyl, phenyl (optionally substituted by one or more substituents each independently selected from $R^a$) or Het (optionally substituted by one or more substituents each independently selected from OH, oxo, or $C_{1-4}$ alkyl);

$R^4$ represents H or $C_{1-3}$ alkyl;

$R^5$ represents $C_{1-6}$ alkyl (optionally substituted by one or more substituents each independently selected from $R^b$), $C_{3-6}$ cycloalkyl (optionally substituted by one or more substituents each independently selected from oxo or OH), or $Het^2$ (optionally substituted by one or more substituents each independently selected from $R^d$); oxygen atom or 1 sulphur atom, or (c) 1 oxygen atom or 1 sulphur atom, (optionally substituted by one or more substituents each independently selected from OH, oxo or $C_{1-4}$ alkyl); and $R^6$ represents $C_{1-3}$ alkyl (optionally substituted by one or more substituents each independently selected from $R^f$), $C_{3-5}$ cycloalkyl (optionally substituted by one or more halogen), CN or halogen; where $R^f$ represents halogen or phenyl: and compositions, processes for the preparation, and uses thereof, e.g. in the treatment of endometriosis or uterine fibroids.

23 Claims, No Drawings

AMIDE COMPOUNDS USEFUL IN THERAPY

This application claims benefit under 35 USC 119(e) to Provisional Patent Application No. 61/097,902 filed Sep. 18, 2008.

This invention relates to novel amide compounds and their derivatives, which are useful in therapy, and to processes for their preparation. It also relates to intermediates used in the preparation of such compounds and derivatives. It also relates to compositions containing such compounds and their uses, for example their use in medicine. A preferred use of the compounds is in the treatment of conditions alleviated by use of a progesterone receptor modulator, preferably a progesterone receptor antagonist. Preferably the compounds are useful in contraception, the treatment of endometriosis, uterine fibroids and related conditions, and in the treatment of breast, ovarian or endometrial cancer.

Endometriosis is a common gynecological disease that affects 10-20% women of reproductive age and manifests itself in the presence of functional ectopic endometrial glands and stroma at locations outside the uterine cavity {Prentice, A. (2001). Bmj 323, 93-95}. Patients with endometriosis may present with many different symptoms and severity. Most commonly this is dysmenorrhea, but chronic pelvic pain, dyspareunia, dyschexia, menorrhagia, lower abdominal or back pain, infertility, bloating and pain on micturition are also part of the constellation of symptoms of endometriosis.

Originally described by Von Rokitansky in 1860 {Von Rokitansky, C. (1860). Ztsch K K Gesellsch der Aerzte zu Wien 37, 577-581}, the exact pathogenesis of endometriosis is unclear {Witz, C. A. (1999). Clinical Obstetrics & Gynecology 42, 566-585; Witz, C. A. (2002). Gynecologic & Obstetric Investigation 53, 52-62}, but the most widely accepted theory is the implantation, or Sampson, theory {Sampson, J. A. (1927). American Journal of Obstetrics & Gynecology 14, 422-429}. The Sampson theory proposes that the development of endometriosis is a consequence of retrograde dissemination and implantation of endometrial tissue into the peritoneal cavity during menstruation. Following attachment, the fragments of endometrium recruit a vascular supply and undergo cycles of proliferation and shedding under local and systemic hormonal controls. In women with patent fallopian tubes, retrograde menstruation appears to be a universal phenomenon {Liu, D. T. (Hitchcock, A.). British Journal of Obstetrics & Gynecology 93, 859-862}. The disease often manifests itself as rectovaginal endometriosis or adenomyosis, ovarian cystic endometriomas and, most commonly, peritoneal endometriosis. The major sites of attachment and lesion growth within the pelvis are the ovaries, broad and round ligaments, fallopian tubes, cervix, vagina, peritoneum and the pouch of Douglas. At its most severe, endometriosis can cause profound structural modification to the peritoneal cavity, including multi-organ adhesions and fibrosis.

Symptomatic endometriosis can be managed medically and surgically, where the intention is to remove the ectopic lesion tissue. Surgical intervention can be either conservative, aiming to preserve the reproductive potential of the patient, or comparatively radical for severe disease, involving dissection of the urinary tract, bowel, and rectovaginal septum, or total abdominal hysterectomy and bilateral salpingo-oophorectomy. Medical pharmacological treatments such as the androgenic therapies, danazol and gestrinone, the constellation of GnRH agonists, buserelin, goserelin, leuprolide, nafarelin and triptorelin, GnRH antagonists, cetrorelix and abarelix, as well as the progestogens, including medroxyprogesterone acetate, induce lesion atrophy by suppressing the production of estrogen. These approaches are not without unwanted side effects; for danazol and gestrinone these include weight gain, hirsutism, acne, mood changes and metabolic effects on the cardiovascular system. The group of GnRH agonists and antagonists are found to cause a profound suppression of estrogen leading to vasomotor effects (hot flashes) and depletion of bone mineral density, which restricts their use to only six months of therapy. The group of progestogens, including medroxyprogesterone acetate, suppress the gonadotropins, but do not down-regulate ovarian estrogen production to the same extent as the GnRH analogues. The side effects include irregular bleeding, bloating, weight gain and metabolic effects on the cardiovascular system.

Uterine leiomyomas {Flake, G. P., et al. (2003). Environmental Health Perspectives 111, 1037-1054; Walker, C. L. (2002). Recent Progress in Hormone Research 57, 277-294}, or fibroids, are the most common benign tumours found in women and occur in the majority of women by the time they reach the menopause. Although uterine fibroids are the most frequent indication for hysterectomy in the United States, as with endometriosis, remarkably little is known about the underlying pathophysiology of the disease. As with endometriotic lesions, the presence of enlarged uterine fibroids is associated with abnormal uterine bleeding, dysmenorrhea, pelvic pain and infertility. Outside of surgical management, medical treatments commonly used for endometriosis, such as GnRH analogues or danazol, have been shown to suppress fibroid growth by inducing a reversible hypoestrogenic state {Chrisp, P., and Goa, K. L. (1990). Drugs 39, 523-551; Chrisp, P., and Goa, K. L. (1991). Drugs 41, 254-288; De Leo, V., et al. (2002). Drug Safety 25, 759-779; Ishihara, H., et al. (2003). Fertility & Sterility 79, 735-742}. However, the future disease management of both uterine fibroids and endometriosis will rely on the development of more effective, well-tolerated and safer agents than those that are currently available.

Steroidal progestins (i.e., progesterone receptor agonists) are commonly used in women's health, such as in contraception and hormone therapy and for the treatment of gynecological disorders. Recent studies in women and in nonhuman primates also indicate that progesterone receptor antagonists may have potential applications in contraception and for the treatment of reproductive disorders such as fibroids and endometriosis as well as dysfunctional uterine bleeding and breast and ovarian carcinomas {Spitz, I. M. (2007), Expert Review of Obstetrics and Gynecology 2(2), 227-242}. Currently, all clinically available progesterone receptor agonists and antagonists are steroidal compounds. They often cause various side effects due to their functional interactions with other steroid receptors or because of effects associated with their steroidal metabolites {Winneker, Richard C. et al.; Endocrinology and Reproductive Disorders Division, Women's Health Research Institute, Collegeville, Pa., USA. Seminars in Reproductive Medicine (2005), 23(1), 46-57}.

Progesterone receptor antagonists [anti-progestins (APs)], including the founding members of the class mifepristone (RU-486; Roussel UCLAF, Romainville, France), onapristone (ZK 98 299; Schering AG), ZK 137 316 and ZK-230 211, are compounds that bind to the progesterone receptor (PR) and prevent progesterone-induced gene expression {Spitz, I. M. (2003). Steroids 68, 981-993}. Acting on the estrogen primed endometrium, progesterone plays an essential role in the differentiation and ductal morphogenesis of endometrial tissue, but also participates in the inhibition of myometrial contractility and the polarisation of leukocyte Th1/Th2 responses that are critical for embryo implantation and the maintenance of pregnancy. A number of studies have investigated the potential beneficial effects of anti-progestins on the signs and symptoms of endometriosis {Grow, D. R., et al. (1996). Journal of Clinical Endocrinology & Metabolism 81, 1933-1939; Kettel, L. M., et al. (1996). Fertility & Sterility 65, 23-28; Kettel, L. M., et al. (1998). American Journal of Obstetrics & Gynecology 178, 1151-1156.} and uterine fibroids {Eisinger, S. H., et al. (2003). Obstetrics & Gynecology 101, 243-250; Murphy, A. A., and Castellano, P. Z. (1994). Current Opinion in Obstetrics & Gynecology 6, 269-278; Murphy, A. A., et al. (1995). Fertility & Sterility 63, 761-766; Steinauer, J., Pritts, et al. (2004). Obstetrics & Gynecology 103, 1331-1336; Yang, Y., et al. (1996). Chinese. Chung-Hua Fu Chan Ko Tsa Chih [Chinese Journal of Obstetrics & Gynecology] 31, 624-626}. Unlike GnRH analogues, and other conventional pharmacological approaches, anti-progestins, especially mifepristone, appear to be able to reduce lesion or fibroid volume, whilst maintaining a tonic level of ovarian oestrogen secretion. Such anti-progestins induce amenorrhoea and endometrial compaction, and also appear to sufficiently protect against rapid oestrogen-dependent bone loss {Grow, D. R., et al. (1996). Journal of Clinical Endocrinology & Metabolism 81, 1933-1939}. In contrast GnRH analogues cause a rapid loss in bone mineral density, a clinical feature which limits their treatment duration to 6 months. Whilst mifepristone is a potent anti-progestin, it also has equipotent anti-glucocorticoid activity. Outside of a palliative treatment of hypercortisolism for Cushing's syndrome {Chu, J. W., et al. (2001). J Clin Endocrinol Metab 86, 3568-3573; Sartor, O., and Cutler, G. B., Jr. (1996). Clin Obstet Gynaecol 39, 506-510; Spitz, I. M. (2003). Steroids 68, 981-993; Van Look, P. F., and von Hertzen, H. (1995). Human Reproduction Update 1, 19-34}, the anti-glucocorticoid activity is an undesirable feature of mifepristone and potentially many of the steroidal classes of anti-progestins.

A further class of steroidal and non-steroidal compounds, termed the progesterone receptor modulators (PRMs, or mesoprogestins), including asoprisnil (J867, benzaldehyde, 4-[(11β,17β)-17-methoxy-17-(methoxymethyl)-3-oxoestra-4,9-dien-11-yl]-, 1-oxime; Jenpharm, TAP), J912, J956, J1042, have also been described. In addition to their potential utility in hormone replacement and as contraceptives, these classes of compounds could be considered to have utility in the treatment of endometriosis and uterine leiomyoma {Chwalisz, K., et al. (2004). Semin Reprod Med 22, 113-119; Chwalisz, K., et al. (2002). Annals of the New York Academy of Sciences 955, 373-388; discussion 389-393; DeManno, D., et al. (2003). Steroids 68, 1019-1032}. Asoprisnil and structurally-related PRMs differ from anti-progestins and progestins in animal models, demonstrating partial progestogenic activity in the rabbit endometrium (McPhail's test {McPhail, M. K. (1934). Journal of physiology 83, 145-156.}) and guinea pig vagina, for instance. Pre-clinical studies with asoprisinil in primates have indicated that PRMs suppress endometrial growth and, unlike the effects of progestins, endometrial ER and PR expression is not repressed {Chwalisz, K., et al. (2000). Steroids 65, 741-751; DeManno, D., et al. (2003). Steroids 68, 1019-1032; Elger, W., et al. (2000). Steroids 65, 713-723}.

The expression of both PR isoforms in reproductive tissues is altered during carcinogenesis. The over expression of PR-B, for instance, has been shown to correlate with more aggressive endometrial and ovarian cancers {Fujimoto et al (1995) Tumour Biology 16, 254-60}. In the area of either breast cancer protection or for the treatment of hormone-dependent breast cancer, there are already pre-clinical data with RU486, onapristone and CDB-4124 in DMBA-induced breast cancer in the rat {Wiehle et al 2007 Oncology Reports 18, 167-174}. In these studies, both agents decreased tumour volume and increased apoptosis. Three small clinical trials in women with advanced metastatic breast cancer have shown that onapristone and RU486 have some efficacy {Klijn et al. 1989 Cancer Research 49, 2851-6; Romieu et al 1987 Bull Cancer 74, 455-61; Robertson et al. 1999 European Journal of Cancer 35, 214-8}. In a Phase 2 study in ovarian cancer patients, refractory to cisplatin and paclitaxel, 26.5% of patients had a clinical response to RU486 (200 mg/day) {Rocereto et al. 2000 Gynecological Oncology 77, 429-32}.

Women with mutations in the breast cancer susceptibility gene BRCA1 are pre-disposed to breast and ovarian cancers. Mammary glands of nulliparous Brca1/p53-deficient mice develop palpable tumours within 6 months of age. Treatment of Brca1/p53-deficient mice with RU486 prevented mammary tumorigenesis, raising the possibility that anti-progesterone treatment may be effective in breast cancer prevention in individuals with BRCA1 mutations {Aleksandra et al. 2006 Science 314, 1467-1470}.

A selective progesterone receptor antagonist, which is devoid of anti-glucocorticoid activity, may be less affected by dose-limiting side effects and prove effective in treating endometrial, ovarian and breast cancer.

The compounds of the present invention have been found to have potentially useful pharmaceutical properties. They may be used to treat conditions such as endometriosis, uterine fibroids (leiomyomata) and menorrhagia, adenomyosis, primary and secondary dysmenorrhea (including symptoms of dyspareunia, dyschexia and chronic pelvic pain), chronic pelvic pain syndrome, precocious puberty, cervical ripening, contraception (emergency), breast carcinoma, ovarian carcinoma, endometrial carcinoma, prostate carcinoma, pulmonary carcinoma, testicular carcinoma, gastric carcinoma, meningioma, anxiety, premenstrual syndrome, premenstrual dysphoric disorder, alcohol abuse and reward, or Charcot-Marie-Tooth disease. Particularly of interest is the treatment of the following diseases or disorders: endometriosis, uterine fibroids (leiomyomata), menorrhagia, adenomyosis, primary and secondary dysmenorrhea (including symptoms of dyspareunia, dyschexia and chronic pelvic pain), chronic pelvic pain syndrome, and breast, ovarian or endometrial cancer.

More particularly of interest is the treatment or prevention of one or more pain and/or other symptoms associated with endometriosis and/or uterine fibroids. These symptoms may comprise dysmenorrhea; chronic non-menstrual pelvic pain; dyspareunia; dyschexia; menorrhagia; lower abdominal or back pain; infertility and subfertility; dysuria; bloating and pain on micturition; nausea, vomiting and/or diarrohea. Such treatment may involve curative, prophylactic or palliative treatment of the underlying condition or of one or more symptoms of the condition, for example, pain.

In particular, the compounds and derivatives of the present invention exhibit activity as progesterone receptor modulators and may be useful for treatment where progesterone receptor modulation is indicated.

More particularly, the compounds and derivatives of the present invention may be useful for treating endometriosis and/or uterine fibroids (leiomyomata), including the pain symptoms thereof, and for the treatment of breast, ovarian or endometrial cancer.

According to one aspect of the present invention there is provided a compound of Formula (I), or a pharmaceutically acceptable salt or solvate thereof:

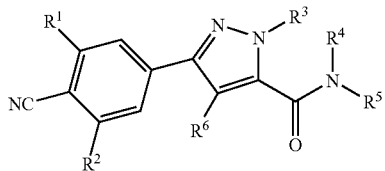

wherein, $R^1$ and $R^2$ each independently represent H, halogen, $CF_3$, $C_{1-3}$ alkyl or $C_{1-3}$ alkoxy;

$R^3$ represents $C_{1-6}$ alkyl, $C_{3-6}$ cycloalkyl, phenyl (optionally substituted by one or more substituents each independently selected from $R^a$) or Het (optionally substituted by one or more substituents each independently selected from OH, oxo, or $C_{1-4}$ alkyl);

$R^a$ represents halogen, $CF_3$, or CN;

Het represents a 5- or 6-membered, saturated, partially saturated, or aromatic, heterocyclic ring comprising (a) from 1 to 4 nitrogen atoms, or
(b) 1 or 2 nitrogen atoms and 1 oxygen atom or 1 sulphur atom, or (c) 1 oxygen atom or 1 sulphur atom;

$R^4$ represents H or $C_{1-3}$ alkyl;

$R^5$ represents $C_{1-6}$ alkyl (optionally substituted by one or more substituents each independently selected from $R^b$), $C_{3-6}$ cycloalkyl (optionally substituted by one or more substituents each independently selected from oxo or OH), or $Het^2$ (optionally substituted by one or more substituents each independently selected from $R^d$); where $R^b$ represents OH, halogen, $C_{3-6}$ cycloalkyl, $OC_{1-4}$ alkyl, $COR^c$, $NR^d_2$, or $Het^1$; where $R^c$ independently represents $-NH_2$, $-NHC_{1-4}$ alkyl, $-N(C_{1-4}\text{ alkyl})_2$, $-OC_{1-4}$ alkyl or $-C_{1-4}$ alkyl;

$R^d$ independently represents H or $C_{1-4}$ alkyl; and $Het^1$ independently represents a 5- or 6-membered, saturated, partially saturated, or aromatic, heterocyclic ring comprising (a) from 1 to 4 nitrogen atoms, or (b) 1 or 2 nitrogen atoms and 1 oxygen atom or 1 sulphur atom, or (c) 1 oxygen atom or 1 sulphur atom, (optionally substituted by one or more substituents each independently selected from OH, oxo or $C_{1-4}$ alkyl);

$Het^2$ represents a 4- to 6-membered, saturated, partially saturated, or aromatic, monocyclic heterocyclic ring, or a 7- to 12-membered saturated, partially saturated, or aromatic, bicyclic heterocyclic ring, comprising (a) from 1 to 4 nitrogen atoms, or (b) 1 or 2 nitrogen atoms and 1 oxygen atom or 1 sulphur atom, or (c) 1 oxygen atom or 1 sulphur atom; and $R^d$ represents $C_{1-4}$ alkyl, oxo, OH, $COC_{1-4}$ alkyl, $COOC_{1-4}$ alkyl, $SO_2C_{1-4}$ alkyl, $NH_2$, $CONHC_{1-4}$ alkyl, or $CON(C_{1-4}\text{ alkyl})_2$; and $R^6$ represents $C_{1-3}$ alkyl (optionally substituted by one or more substituents each independently selected from $R^f$), $C_{3-5}$ cycloalkyl (optionally substituted by one or more halogen), CN or halogen; where $R^f$ represents halogen or phenyl.

The invention described herein also provides pharmaceutical compositions comprising a compound of Formula (I), or a pharmaceutically acceptable salt or solvate (including hydrate) thereof, and a pharmaceutically acceptable carrier.

The following embodiments are preferred:

(i) a compound of Formula (I), as defined above, wherein $R^1$ represents H or $C_{1-3}$ alkyl;

(ii) a compound of Formula (I), as defined above, or embodiment (i) above, wherein $R^1$ represents $C_{1-3}$ alkyl, preferably methyl;

(iii) a compound of Formula (I), as defined above, or embodiment (i) above, wherein $R^1$ represents H;

(iv) a compound of Formula (I), as defined above, or embodiment (i) above, wherein $R^1$ represents methyl;

(v) a compound of Formula (I), as defined above, or any of embodiments (i) to (iv) above, wherein $R^2$ represents H, Cl or $C_{1-3}$ alkyl;

(vi) a compound of Formula (I), as defined above, or any of embodiments (i) to (v) above, wherein $R^2$ represents $C_{1-3}$ alkyl, preferably methyl;

(vii) a compound of Formula (I), as defined above, or any of embodiments (i) to (v) above, wherein $R^2$ represents H;

(viii) a compound of Formula (I), as defined above, or any of embodiments (i) to (v) above, wherein $R^2$ represents methyl;

(ix) a compound of Formula (I), as defined above, or any of embodiments (i) to (viii) above, wherein $R^3$ represents $C_{1-6}$ alkyl, $C_{3-6}$ cycloalkyl, or Het;

(x) a compound of Formula (I), as defined above, or any of embodiments (i) to (ix) above, wherein when $R^3$ represents $C_{1-6}$ alkyl, it is $C_{3-4}$ alkyl, preferably isopropyl or butan-2-yl;

(xi) a compound of Formula (I), as defined above, or any of embodiments (i) to (ix) above, wherein when $R^3$ represents cycloalkyl, it is $C_{3-4}$ cycloalkyl, preferably cyclopropyl or cyclobutyl;

(xii) a compound of Formula (I), as defined above, or any of embodiments (i) to (ix) above, wherein when $R^3$ represents cycloalkyl, it is cyclobutyl;

(xiii) a compound of Formula (I), as defined above, or any of embodiments (i) to (ix) above, wherein when $R^3$ represents Het, it is tetrahydrofuranyl, preferably 3-tetrahydrofuranyl;

(xiv) a compound of Formula (I), as defined above, or any of embodiments (i) to (x) above, wherein $R^3$ represents $C_3$ alkyl, preferably isopropyl.

(xv) a compound of Formula (I), as defined above, or any of the embodiments (i) to (xiv) above, wherein $R^4$ represents H or $C_{1-3}$ alkyl, preferably H or methyl;

(xvi) a compound of Formula (I), as defined above, or any of the embodiments (i) to (xv) above, wherein $R^4$ represents H;

(xvii) a compound of Formula (I), as defined above, or any of the embodiments (i) to (xvi) above, wherein when $R^5$ represents $C_{1-6}$ alkyl, it is $C_{1-4}$ alkyl;

(xviii) a compound of Formula (I), as defined above, or any of the embodiments (i) to (xvii) above, wherein when $R^5$ represents $C_{1-4}$ alkyl, $R^b$ represents OH;

(xix) a compound of Formula (I), as defined above, or any of the embodiments (i) to (xvii) above, wherein when $R^5$ represents $C_i$ alkyl, $R^b$ represents $COR^c$;

(xx) a compound of Formula (I), as defined above, or any of the embodiments (i) to (xvii) above, wherein when $R^5$ represents $C_{2-3}$ alkyl, it is unsubstituted;

(xxi) a compound of Formula (I), as defined above, or any of the embodiments (i) to (xvii) above, wherein when $R^5$ represents $C_3$ alkyl, it is unsubstituted;

(xxii) a compound of Formula (I), as defined above, or any of the embodiments (i) to (xvi) above, wherein when $R^5$ represents $C_3$ cycloalkyl, it is unsubstituted;

(xxiii) a compound of Formula (I), as defined above, or any of the embodiments (i) to (xvii) above, wherein $R^b$ represents OH, halogen, $C_{3-4}$ cycloalkyl, $OC_{1-4}$ alkyl, $COR^c$, $NR^d_2$, or $Het^1$;

(xxiv) a compound of Formula (I), as defined above, or any of the embodiments (i) to (xvii) above, wherein $R^b$ represents OH, halogen, $C_{3-4}$ cycloalkyl, OMe, $COR^c$, $NR^d_2$, or $Het^1$;

(xxv) a compound of Formula (I), as defined above, or any of the embodiments (i) to (xvii) above, wherein $R^b$ represents OH, $C_{3-6}$ cycloalkyl, $OC_{1-4}$ alkyl, $COR^c$, $NR^d_2$;

(xxvi) a compound of Formula (I), as defined above, or any of the embodiments (i) to (xvii) above, wherein $R^b$ represents OH, $C_{3-6}$ cycloalkyl, $OC_{1-4}$ alkyl, $COR^c$, $NR^d_2$;

(xxvii) a compound of Formula (I), as defined above, or any of the embodiments (i) to (xvii) above, wherein $R^b$ represents OH, $C_{3-4}$ cycloalkyl, $OC_{1-4}$ alkyl, $COR^c$, $NR^d_2$;

(xxviii) a compound of Formula (I), as defined above, or any of the embodiments (i) to (xvii) above, wherein $R^b$ represents OH, $C_{3-4}$ cycloalkyl, OMe, $COR^c$, $NR^d_2$;

(xxix) a compound of Formula (I), as defined above, or any of the embodiments (i) to (xvii) above, wherein $R^b$ represents $NR^d_2$;

(xxx) a compound of Formula (I), as defined above, or any of the embodiments (i) to (viii) above, wherein $R^c$ represents —NHMe, —$OC_{1-4}$ alkyl, or —$C_{1-4}$ alkyl;

(xxxi) a compound of Formula (I), as defined above, or any of the embodiments (i) to (viii) above, wherein $R^c$ represents —$NHC_{1-4}$ alkyl, —OMe, or —$C_{1-4}$ alkyl;

(xxxii) a compound of Formula (I), as defined above, or any of the embodiments (i) to (viii) above, wherein $R^c$ represents —$NHC_{1-4}$ alkyl, —$OC_{1-4}$ alkyl, or methyl;

(xxxiii) a compound of Formula (I), as defined above, or any of the embodiments (i) to (xxxi) above, wherein $R^c$ represents —NHMe, —OMe, or —$C_{1-4}$ alkyl;

(xxxiv) a compound of Formula (I), as defined above, or any of the embodiments (i) to (xxxiii) above, wherein $R^c$ represents —NHMe, —OMe, or methyl;

(xxxv) a compound of Formula (I), as defined above, or any of the embodiments (i) to (xxxiv) above, wherein $R^d$ is independently selected from H and $C_{1-2}$ alkyl;

(xxxvi) a compound of Formula (I), as defined above, or any of the embodiments (i) to (xxxiv) above, wherein $R^d$ is independently selected from H and ethyl;

(xxxvii) a compound of Formula (I), as defined above, or any of the embodiments (i) to (xxxiv) above, wherein $R^d$ is independently selected from H and methyl;

(xxxviii) a compound of Formula (I), as defined above, or any of the embodiments (i) to (xxxvii) above, wherein $Het^1$ represents a 5- or 6-membered saturated, partially saturated, or aromatic, heterocyclic ring comprising (a) from 1 to 4 nitrogen atoms, or (b) 1 or 2 nitrogen atoms and 1 oxygen atom, or (c) 1 oxygen atom, (optionally substituted with one or more substituents independently selected from $C_{1-4}$ alkyl or oxo);

(xxxix) a compound of Formula (I), as defined above, or any of the embodiments (i) to (xxxviii) above, wherein $Het^1$ represents a 5- or 6-membered saturated, partially saturated, or aromatic, heterocyclic ring comprising (a) from 1 to 2 nitrogen atoms, or (b) 1 or 2 nitrogen atoms and 1 oxygen atom, or (c) 1 oxygen atom, (optionally substituted with one or more substituents independently selected from $C_{1-4}$ alkyl or oxo);

(xl) a compound of Formula (I), as defined above, or any of the embodiments (i) to (xxxix) above, wherein $Het^1$ represents tetrahydrofuran, pyrimidine, pyrrolidinone, or pyrazole;

(xli) a compound of Formula (I), as defined above, or any of the embodiments (i) to (xl) above, wherein $Het^2$ represents a 4- to 6-membered saturated, partially saturated, or aromatic, monocyclic heterocyclic ring or a 7- to 12-membered saturated, partially saturated, or aromatic, bicyclic heterocyclic ring, comprising (a) from 1 to 4 nitrogen atoms, or (b) 1 or 2 nitrogen atoms and 1 oxygen atom, or (c) 1 oxygen atom, (optionally substituted with one or more substituents independently selected from oxo);

(xlii) a compound of Formula (I), as defined above, or any of the embodiments (i) to (xli) above, wherein $Het^2$ represents a 4- to 6-membered saturated, partially saturated, or aromatic, monocyclic heterocyclic ring or a 7- to 12-membered saturated, partially saturated, or aromatic, bicyclic heterocyclic ring, comprising (a) 1 or 2 nitrogen atoms, or (b) 1 nitrogen atom and 1 oxygen atom, or (c) 1 oxygen atom, (optionally substituted with one or more substituents independently selected from oxo);

(xliii) a compound of Formula (I), as defined above, or any of the embodiments (i) to (xlii) above, wherein $Het^2$ represents pyrrolidine, pyrrolidinone, piperidinone, azetidine, tetrahydrofuran, dihydrofuranone; tetrahydropyran, or dihydropyrroloimidazole;

(xliv) a compound of Formula (I), as defined above, or any of the embodiments (i) to (xliii) above, wherein $R^6$ represents $C_{1-3}$ alkyl (optionally substituted by one or more phenyl substituents), $C_{3-5}$ cycloalkyl (optionally substituted by one or more halogen), CN or halogen;

(xlv) a compound of Formula (I), as defined above, or any of the embodiments (i) to (xliv) above, wherein $R^6$ represents $C_{1-3}$ alkyl (optionally substituted by one or more phenyl substituents), $C_{3-5}$ cycloalkyl (optionally substituted by one or more F), CN or halogen;

(xlvi) a compound of Formula (I), as defined above, or any of the embodiments (i) to (xlv) above, wherein $R^6$ represents $C_{1-2}$ alkyl (optionally substituted by one or more phenyl substituents), $C_{3-4}$ cycloalkyl (optionally substituted by one or more F), CN or halogen, preferably methyl, ethyl, cyclopropyl, 3,3-difluorocyclobutyl, benzyl, cyano or chloro; (xlvii) a compound of Formula (I), as defined above, or any of the embodiments (i) to (xlvi) above, wherein $R^6$ represents $C_{1-3}$ alkyl, $C_{3-5}$ cycloalkyl, CN or halogen;

(xlviii) a compound of Formula (I), as defined above, or any of the embodiments (i) to (xlvii) above, wherein $R^6$ represents $C_{1-3}$ alkyl, $C_{3-5}$ cycloalkyl, CN or chloro;

(xlix) a compound of Formula (I), as defined above, or any of the embodiments (i) to (xlvi) above, wherein $R^6$ represents methyl, ethyl, cyclopropyl, 3,3-difluorocyclobutyl, chloro or cyano;

(l) a compound of Formula (I), as defined above, or any of the embodiments (i) to (xlvi) above, wherein when $R^6$ represents cyclopropyl or methyl, preferably cyclopropyl.

(li) a compound of Formula (I), as defined above, or any of the embodiments (i) to (l) above, as permissible, wherein $R^5$ represents $C_{1-6}$ alkyl optionally substituted by hydroxy, fluoro, methoxy, $C_{1-4}$ alkanoyl, $C_{1-4}$ alkylaminocarbonyl, amino, $C_{1-4}$ alkoxycarbonyl, $C_{3-6}$ cycloalkyl or $Het^1$; $Het^2$, or $C_{3-6}$ cycloalkyl optionally substituted by hydroxy; and preferably is $C_{1-6}$ alkyl optionally substituted by hydroxy;

(lii) a compound of Formula (I), as defined above, or any of the embodiments (i) to (li) above, as permissible, wherein $R^5$ represents methyl, ethyl, n-propyl, isopropyl, t-butyl, 2-butyl, 2,2-dimethylprop-1-yl, 2-methyl-2-hydroxyprop-1-yl, 2-hydroxyprop-1-yl, 3-hydroxy-2-methylprop-2-yl, 2,2,2-trifluoroethyl, 3-methoxyprop-1-yl, 2-methoxyethyl, 3,3,3-trifluoroprop-1-yl, acetylmethyl, methylaminocarbonylmethyl, ethylaminocarbonylmethyl, 2-aminoethyl, 2-amino-2-methylprop-1-yl, 2-methoxycarbonylprop-2-yl, cyclopropylmethyl, 2-cyclopropylethyl, tetrahydrofuran-2-ylmethyl, 1-(1-methyl-1H-pyrazol-4-yl)ethyl, pyrimidin-4-ylmethyl, 1-(1H-pyrazol-1-yl)prop-2-yl, 3-(2-oxopyrrolidin-1-yl)prop-1-yl, (1-methyl-1H-pyrazol-4-yl)methyl, 1-t-butoxycarbonyl pyrrolidin-3-yl, 1-t-butoxycarbonylazetidin3-yl, pyrrolidin-3-yl, azetidin-3-yl, 1-isopropylcarbonylpyrrolidin-3-yl, 1-ethylcarbonylpyrrolidin-3-yl, 1-methanesulphonylpyrrolidin-3-yl, 1-isopropylcarbonylazetidin-3-yl, 1-ethylcarbonylazetidin-3-yl, 1-methanesulphonylazetidin-3-yl, 1-acetylazetidin-3-yl, 2-oxotetrahydrofuran-3-yl, 6,7-dihydro-5H-pyrrolo[1,2-a]imidazol-6-yl, tetrahydro-2H-pyran-3-yl, tetrahydro-2H-pyran-4-yl, 1-methyl-6-oxopiperidin-3-yl, 5-oxopyrrolidin-3-yl, tetrahydrofuran-3-yl, 1,1-dioxidotetrahydro-3-thienyl, cyclopentyl, cyclobutyl, 3-hydroxycyclobutyl or 3-hydroxycyclopentyl; and preferably is 2-methyl-2-hydroxyprop-1-yl.

According to another aspect of the present invention there is provided a compound of Formula (Ia), or a pharmaceutically acceptable salt or solvate thereof:

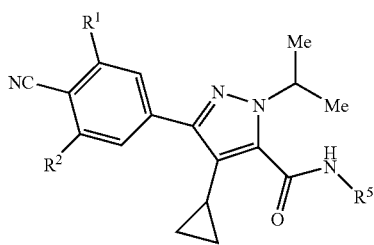

wherein, $R^1$, $R^2$ and $R^5$ are as defined for a compound of formula (I) above and preferably $R^1$ and $R^2$ are both H.

According to another aspect of the present invention there is provided a compound of Formula (Ib), or a pharmaceutically acceptable salt or solvate thereof:

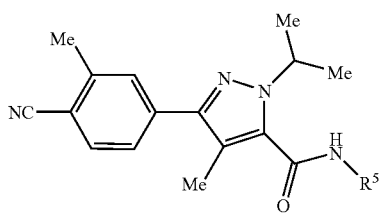

wherein, $R^5$ is as defined for a compound of formula (I) above.

According to another aspect of the present invention there is provided a compound of Formula (Ic), or a pharmaceutically acceptable salt or solvate thereof:

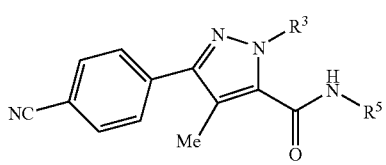

wherein, $R^3$ and $R^5$ are as defined for a compound of formula (I) above.

According to another aspect of the present invention there is provided a compound of Formula (Id), or a pharmaceutically acceptable salt or solvate thereof:

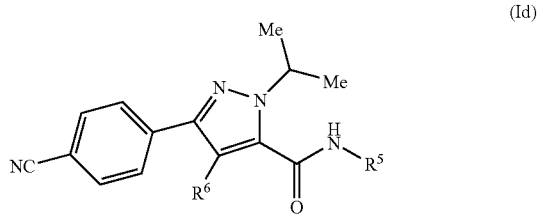

wherein, $R^5$ and $R^6$ are as defined for a compound of formula (I) above.

Particular compounds of interest falling within the scope of the invention are:
3-(4-cyanophenyl)-4-cyclopropyl-N-(2-hydroxy-2-methylpropyl)-1-isopropyl-1H-pyrazole-5-carboxamide;
3-(4-cyanophenyl)-4-cyclopropyl-N-[(2S)-2-hydroxypropyl]-1-isopropyl-1H-pyrazole-5-carboxamide;
3-(4-cyanophenyl)-4-cyclopropyl-N-[(2R)-2-hydroxypropyl]-1-isopropyl-1H-pyrazole-5-carboxamide;
3-(4-cyanophenyl)-4-cyclopropyl-N,1-diisopropyl-1H-pyrazole-5-carboxamide;
tert-butyl (3R)-3-({[3-(4-cyanophenyl)-4-cyclopropyl-1-isopropyl-1H-pyrazol-5-yl]carbonyl}amino)pyrrolidine-1-carboxylate;
tert-butyl (3S)-3-({[3-(4-cyanophenyl)-4-cyclopropyl-1-isopropyl-1H-pyrazol-5-yl]carbonyl}amino)pyrrolidine-1-carboxylate;
tert-butyl 3-({[3-(4-cyanophenyl)-4-cyclopropyl-1-isopropyl-1H-pyrazol-5-yl]carbonyl}amino)azetidine-1-carboxylate;
3-(4-cyanophenyl)-4-cyclopropyl-1-isopropyl-N-[(3R)-pyrrolidin-3-yl]-1H-pyrazole-5-carboxamide;
3-(4-cyanophenyl)-4-cyclopropyl-1-isopropyl-N-[(3S)-pyrrolidin-3-yl]-1H-pyrazole-5-carboxamide;
N-azetidin-3-yl-3-(4-cyanophenyl)-4-cyclopropyl-1-isopropyl-1H-pyrazole-5-carboxamide;
3-(4-cyanophenyl)-4-cyclopropyl-N-[(3R)-1-isobutyrylpyrrolidin-3-yl]-1-isopropyl-1H-pyrazole-5-carboxamide;
3-(4-Cyanophenyl)-4-cyclopropyl-1-isopropyl-N-[(3S)-1-propionylpyrrolidin-3-yl]-1H-pyrazole-5-carboxamide;
3-(4-cyanophenyl)-4-cyclopropyl-1-isopropyl-N-[(3R)-1-(methylsulfonyl)pyrrolidin-3-yl]-1H-pyrazole-5-carboxamide;
3-(4-cyanophenyl)-4-cyclopropyl-N-[(3S)-1-isobutyrylpyrrolidin-3-yl]-1-isopropyl-1H-pyrazole-5-carboxamide;
3-(4-cyanophenyl)-4-cyclopropyl-1-isopropyl-N-[(3S)-1-propionylpyrrolidin-3-yl]-1H-pyrazole-5-carboxamide;
3-(4-cyanophenyl)-4-cyclopropyl-N-(1-isobutyrylazetidin-3-yl)-1-isopropyl-1H-pyrazole-5-carboxamide;
3-(4-cyanophenyl)-4-cyclopropyl-1-isopropyl-N-(1-propionylazetidin-3-yl)-1H-pyrazole-5-carboxamide;
3-(4-cyanophenyl)-4-cyclopropyl-1-isopropyl-N-[1-(methylsulfonyl)azetidin-3-yl]-1H-pyrazole-5-carboxamide;
N-(1-acetylazetidin-3-yl)-3-(4-cyanophenyl)-4-cyclopropyl-1-isopropyl-1H-pyrazole-5-carboxamide;
3-(4-cyanophenyl)-4-cyclopropyl-1-isopropyl-N-propyl-1H-pyrazole-5-carboxamide;
3-(4-cyanophenyl)-4-cyclopropyl-1-isopropyl-N-(3-methoxypropyl)-1H-pyrazole-5-carboxamide;

3-(4-cyanophenyl)-4-cyclopropyl-1-isopropyl-N-(3,3,3-trifluoropropyl)-1H-pyrazole-5-carboxamide;
3-(4-cyanophenyl)-4-cyclopropyl-1-isopropyl-N-(pyrimidin-4-ylmethyl)-1H-pyrazole-5-carboxamide;
3-(4-cyanophenyl)-4-cyclopropyl-1-isopropyl-N-[(3S)-2-oxotetrahydrofuran-3-yl]-1H-pyrazole-5-carboxamide;
3-(4-cyanophenyl)-4-cyclopropyl-1-isopropyl-N-[2-(methylamino)-2-oxoethyl]-1H-pyrazole-5-carboxamide;
3-(4-cyanophenyl)-4-cyclopropyl-1-isopropyl-N-[3-(2-oxopyrrolidin-1-yl)propyl]-1H-pyrazole-5-carboxamide;
methyl N-{[3-(4-cyanophenyl)-4-cyclopropyl-1-isopropyl-1H-pyrazol-5-yl]carbonyl}-2-methylalaninate;
N-(2-aminoethyl)-3-(4-cyanophenyl)-4-cyclopropyl-1-isopropyl-1H-pyrazole-5-carboxamide;
N-(2-amino-2-methylpropyl)-3-(4-cyanophenyl)-4-cyclopropyl-1-isopropyl-1H-pyrazole-5-carboxamide;
3-(4-cyanophenyl)-4-cyclopropyl-1-isopropyl-N-[(1-methyl-1H-pyrazol-4-yl)methyl]-1H-pyrazole-5-carboxamide;
3-(4-cyanophenyl)-4-cyclopropyl-N-[(1R,3S)-3-hydroxycyclopentyl]-1-isopropyl-1H-pyrazole-5-carboxamide;
3-(4-cyanophenyl)-4-cyclopropyl-N-(cis-3-hydroxycyclobutyl)-1-isopropyl-1H-pyrazole-5-carboxamide;
3-(4-cyanophenyl)-4-cyclopropyl-1-isopropyl-N-[(1S)-1-methylpropyl]-1H-pyrazole-5-carboxamide;
3-(4-cyanophenyl)-4-cyclopropyl-N-(2,2-dimethylpropyl)-1-isopropyl-1H-pyrazole-5-carboxamide;
3-(4-cyanophenyl)-4-cyclopropyl-1-isopropyl-N-[(1R)-1-methylpropyl]-1H-pyrazole-5-carboxamide;
3-(4-cyanophenyl)-4-cyclopropyl-1-isopropyl-N-(tetrahydrofuran-2-ylmethyl)-1H-pyrazole-5-carboxamide;
3-(4-cyanophenyl)-4-cyclopropyl-N-[(6S)-6,7-dihydro-5H-pyrrolo[1,2-a]imidazol-6-yl]-1-isopropyl-1H-pyrazole-5-carboxamide;
3-(4-cyanophenyl)-4-cyclopropyl-N-[(6R)-6,7-dihydro-5H-pyrrolo[1,2-a]imidazol-6-yl]-1-isopropyl-1H-pyrazole-5-carboxamide;
3-(4-cyanophenyl)-4-cyclopropyl-1-isopropyl-N-[1-(1-methyl-1H-pyrazol-4-yl)ethyl]-1H-pyrazole-5-carboxamide;
3-(4-cyanophenyl)-4-cyclopropyl-1-isopropyl-N-(tetrahydro-2H-pyran-3-yl)-1H-pyrazole-5-carboxamide;
3-(4-cyanophenyl)-4-cyclopropyl-1-isopropyl-N-(1-methyl-6-oxopiperidin-3-yl)-1H-pyrazole-5-carboxamide;
3-(4-cyanophenyl)-4-cyclopropyl-N-[2-(ethylamino)-2-oxoethyl]-1-isopropyl-1H-pyrazole-5-carboxamide;
3-(4-cyanophenyl)-4-cyclopropyl-1-isopropyl-N-(tetrahydro-2H-pyran-4-yl)-1H-pyrazole-5-carboxamide;
3-(4-cyanophenyl)-4-cyclopropyl-1-isopropyl-N-[1-methyl-2-(1H-pyrazol-1-yl)ethyl]-1H-pyrazole-5-carboxamide;
3-(4-cyanophenyl)-4-cyclopropyl-1-isopropyl-N-[(3R)-5-oxopyrrolidin-3-yl]-1H-pyrazole-5-carboxamide;
3-(4-cyanophenyl)-4-cyclopropyl-1-isopropyl-N-methyl-1H-pyrazole-5-carboxamide;
3-(4-cyanophenyl)-4-cyclopropyl-N-ethyl-1-isopropyl-1H-pyrazole-5-carboxamide;
3-(4-cyanophenyl)-4-cyclopropyl-1-isopropyl-N-(2,2,2-trifluoroethyl)-1H-pyrazole-5-carboxamide;
3-(4-cyanophenyl)-4-cyclopropyl-N-(cyclopropylmethyl)-1-isopropyl-1H-pyrazole-5-carboxamide;
3-(4-cyanophenyl)-N-cyclobutyl-4-cyclopropyl-1-isopropyl-1H-pyrazole-5-carboxamide;
3-(4-cyanophenyl)-4-cyclopropyl-N-(cyclopropylmethyl)-1-isopropyl-N-methyl-1H-pyrazole-5-carboxamide;
3-(4-cyanophenyl)-4-cyclopropyl-1-isopropyl-N-(tetrahydrofuran-3-yl)-1H-pyrazole-5-carboxamide;
3-(4-cyanophenyl)-4-cyclopropyl-1-isopropyl-N-[(2R)-tetrahydrofuran-2-ylmethyl]-1H-pyrazole-5-carboxamide;
3-(4-cyanophenyl)-4-cyclopropyl-N-(2-cyclopropylethyl)-1-isopropyl-1H-pyrazole-5-carboxamide;
3-(4-cyanophenyl)-4-cyclopropyl-1-isopropyl-N-[(2S)-tetrahydrofuran-2-ylmethyl]-1H-pyrazole-5-carboxamide;
3-(4-cyanophenyl)-4-cyclopropyl-N-(2-hydroxy-1,1-dimethylethyl)-1-isopropyl-1H-pyrazole-5-carboxamide;
3-(4-cyanophenyl)-4-cyclopropyl-N-(1,1-dioxidotetrahydro-3-thienyl)-1-isopropyl-1H-pyrazole-5-carboxamide;
3-(4-cyanophenyl)-N,4-dicyclopropyl-1-isopropyl-1H-pyrazole-5-carboxamide;
3-(4-cyanophenyl)-4-cyclopropyl-1-isopropyl-N-(2-methoxyethyl)-1H-pyrazole-5-carboxamide;
N-tert-butyl-3-(4-cyanophenyl)-4-cyclopropyl-1-isopropyl-1H-pyrazole-5-carboxamide;
3-(4-cyanophenyl)-4-cyclopropyl-1-isopropyl-N-(2-oxopropyl)-1H-pyrazole-5-carboxamide;
3-(4-cyano-3-methylphenyl)-N-(cyclopropylmethyl)-1-isopropyl-4-methyl-1H-pyrazole-5-carboxamide;
3-(4-cyano-3-methylphenyl)-N-[(2S)-2-hydroxypropyl]-1-isopropyl-4-methyl-1H-pyrazole-5-carboxamide;
3-(4-cyano-3-methylphenyl)-N-[(2R)-2-hydroxypropyl]-1-isopropyl-4-methyl-1H-pyrazole-5-carboxamide;
3-(4-cyano-3-methylphenyl)-N-ethyl-1-isopropyl-4-methyl-1H-pyrazole-5-carboxamide;
3-(4-cyano-3-methylphenyl)-N,1-diisopropyl-4-methyl-1H-pyrazole-5-carboxamide;
3-(4-cyano-3-methylphenyl)-N-cyclopropyl-1-isopropyl-4-methyl-1H-pyrazole-5-carboxamide;
3-(4-cyano-3-methylphenyl)-N-(2-hydroxy-2-methylpropyl)-1-isopropyl-4-methyl-1H-pyrazole-5-carboxamide;
3-(4-cyanophenyl)-1-cyclobutyl-N-(cyclopropylmethyl)-4-methyl-1H-pyrazole-5-carboxamide;
3-(4-cyanophenyl)-1-cyclobutyl-N,4-dimethyl-1H-pyrazole-5-carboxamide;
3-(4-cyanophenyl)-1-cyclobutyl-N-cyclopropyl-4-methyl-1H-pyrazole-5-carboxamide;
3-(4-cyanophenyl)-1-cyclobutyl-N-[(2S)-2-hydroxypropyl]-4-methyl-1H-pyrazole-5-carboxamide;
3-(4-cyanophenyl)-1-cyclobutyl-N-[(2R)-2-hydroxypropyl]-4-methyl-1H-pyrazole-5-carboxamide;
3-(4-cyanophenyl)-1-cyclobutyl-N-(2-hydroxy-2-methylpropyl)-4-methyl-1H-pyrazole-5-carboxamide;
3-(4-cyanophenyl)-1-cyclobutyl-4-methyl-N-[2-(methylamino)-2-oxoethyl]-1H-pyrazole-5-carboxamide;
3-(4-cyanophenyl)-N-ethyl-4-methyl-1-(tetrahydrofuran-3-yl)-1H-pyrazole-5-carboxamide;
3-(4-cyanophenyl)-N-isopropyl-4-methyl-1-(tetrahydrofuran-3-yl)-1H-pyrazole-5-carboxamide;
3-(4-cyanophenyl)-N-[(2S)-2-hydroxypropyl]-4-methyl-1-(tetrahydrofuran-3-yl)-1H-pyrazole-5-carboxamide;
3-(4-cyanophenyl)-N-[(2R)-2-hydroxypropyl]-4-methyl-1-(tetrahydrofuran-3-yl)-1H-pyrazole-5-carboxamide;
3-(4-cyanophenyl)-N-(2-hydroxy-2-methylpropyl)-4-methyl-1-(tetrahydrofuran-3-yl)-1H-pyrazole-5-carboxamide;
3-(4-cyanophenyl)-1-cyclopropyl-N,4-dimethyl-1H-pyrazole-5-carboxamide;
3-(4-cyanophenyl)-1-cyclopropyl-N-(cyclopropylmethyl)-4-methyl-1H-pyrazole-5-carboxamide;
3-(4-cyanophenyl)-1-cyclopropyl-N-ethyl-4-methyl-1H-pyrazole-5-carboxamide;
3-(4-cyanophenyl)-N,1-dicyclopropyl-4-methyl-1H-pyrazole-5-carboxamide;
3-(4-cyanophenyl)-1-cyclopropyl-N-isopropyl-4-methyl-1H-pyrazole-5-carboxamide;
3-(4-cyanophenyl)-1-cyclopropyl-N-[(2S)-2-hydroxypropyl]-4-methyl-1H-pyrazole-5-carboxamide;

3-(4-cyanophenyl)-1-cyclopropyl-N-[(2R)-2-hydroxypropyl]-4-methyl-1H-pyrazole-5-carboxamide;
3-(4-cyanophenyl)-1-cyclopropyl-N-(2-hydroxy-2-methylpropyl)-4-methyl-1H-pyrazole-5-carboxamide;
4-cyano-3-(4-cyanophenyl)-N-ethyl-1-isopropyl-1H-pyrazole-5-carboxamide;
3-(4-cyano-3-methylphenyl)-1-isopropyl-N,4-dimethyl-1H-pyrazole-5-carboxamide;
4-cyano-3-(4-cyanophenyl)-N,1-diisopropyl-1H-pyrazole-5-carboxamide;
4-cyano-3-(4-cyanophenyl)-1-isopropyl-N-methyl-1H-pyrazole-5-carboxamide;
4-cyano-3-(4-cyanophenyl)-N-(cyclopropylmethyl)-1-isopropyl-1H-pyrazole-5-carboxamide;
4-cyano-3-(4-cyanophenyl)-N-cyclopropyl-1-isopropyl-1H-pyrazole-5-carboxamide;
4-benzyl-3-(4-cyanophenyl)-N,1-diisopropyl-1H-pyrazole-5-carboxamide;
4-benzyl-3-(4-cyanophenyl)-N-cyclopropyl-1-isopropyl-1H-pyrazole-5-carboxamide;
4-benzyl-3-(4-cyanophenyl)-N-ethyl-1-isopropyl-1H-pyrazole-5-carboxamide;
3-(4-cyanophenyl)-N-cyclopropyl-4-(3,3-difluorocyclobutyl)-1-isopropyl-1H-pyrazole-5-carboxamide;
3-(4-cyanophenyl)-4-(3,3-difluorocyclobutyl)-1-isopropyl-N-methyl-1H-pyrazole-5-carboxamide;
3-(4-cyanophenyl)-4-(3,3-difluorocyclobutyl)-N-ethyl-1-isopropyl-1H-pyrazole-5-carboxamide;
1-sec-butyl-3-(4-cyanophenyl)-N-(cyclopropylmethyl)-4-ethyl-1H-pyrazole-5-carboxamide;
1-sec-butyl-3-(4-cyanophenyl)-4-ethyl-N-isopropyl-1H-pyrazole-5-carboxamide;
1-sec-butyl-3-(4-cyanophenyl)-N,4-diethyl-1H-pyrazole-5-carboxamide;
1-sec-butyl-3-(4-cyanophenyl)-N-cyclopropyl-4-ethyl-1H-pyrazole-5-carboxamide;
1-sec-butyl-3-(4-cyanophenyl)-4-ethyl-N-methyl-1H-pyrazole-5-carboxamide;
1-sec-butyl-3-(4-cyanophenyl)-4-ethyl-N-(2-hydroxy-2-methylpropyl)-1H-pyrazole-5-carboxamide;
1-sec-butyl-3-(4-cyanophenyl)-4-ethyl-N-[(2R)-2-hydroxypropyl]-1H-pyrazole-5-carboxamide;
1-sec-butyl-3-(4-cyanophenyl)-4-ethyl-N-[(2S)-2-hydroxypropyl]-1H-pyrazole-5-carboxamide;
1-sec-butyl-3-(4-cyanophenyl)-4-ethyl-N-[2-(methylamino)-2-oxoethyl]-1H-pyrazole-5-carboxamide;
3-(4-cyanophenyl)-N-(cyclopropylmethyl)-4-ethyl-1-isopropyl-1H-pyrazole-5-carboxamide;
3-(4-cyanophenyl)-N-cyclopropyl-4-ethyl-1-isopropyl-1H-pyrazole-5-carboxamide;
3-(4-cyanophenyl)-4-ethyl-1-isopropyl-N-methyl-1H-pyrazole-5-carboxamide;
3-(4-cyano-3-methylphenyl)-1-isopropyl-4-methyl-N-[2-(methylamino)-2-oxoethyl]-1H-pyrazole-5-carboxamide;
3-(4-cyanophenyl)-4-ethyl-N-[(2S)-2-hydroxypropyl]-1-isopropyl-1H-pyrazole-5-carboxamide;
3-(4-cyanophenyl)-4-ethyl-N-[(2R)-2-hydroxypropyl]-1-isopropyl-1H-pyrazole-5-carboxamide;
3-(4-cyanophenyl)-N,4-diethyl-1-isopropyl-1H-pyrazole-5-carboxamide;
3-(4-cyanophenyl)-4-ethyl-N,1-diisopropyl-1H-pyrazole-5-carboxamide;
3-(4-cyanophenyl)-4-ethyl-N-(2-hydroxy-2-methylpropyl)-1-isopropyl-1H-pyrazole-5-carboxamide;
3-(4-cyanophenyl)-4-ethyl-1-isopropyl-N-[2-(methylamino)-2-oxoethyl]-1H-pyrazole-5-carboxamide; and
3-(4-cyano-3-methylphenyl)-4-cyclopropyl-1-isopropyl-N-[2-(methylamino)-2-oxoethyl]-1H-pyrazole-5-carboxamide;
or a pharmaceutically acceptable salt or solvate of any thereof.

Further preferred compounds of the invention are selected from those described in Examples 121 to 134 hereafter, including the pharmaceutically acceptable salts and solvates thereof.

In the above definitions alkyl groups containing the requisite number of carbon atoms, except where indicated, can be unbranched or branched chain. Examples include methyl, ethyl, n-propyl, i-propyl, n-butyl, i-butyl, sec-butyl and t-butyl. Examples of alkyloxy (alkoxy) include methoxy, ethoxy, n-propyloxy, i-propyloxy, n-butyloxy, i-butyloxy, sec-butyloxy and t-butyloxy. Examples of cycloalkyl include cyclopropyl, cyclobutyl, cyclopentyl, and cyclohexyl. The term halogen means fluoro, chloro, bromo or iodo.

The above described (preferred) embodiments of the invention may be combined with one or more further embodiments such that further embodiments are provided wherein two or more variables are defined more specifically in combination. All such combinations of the more specific embodiments described and defined above are within the scope of the invention.

Pharmaceutically acceptable derivatives of the compounds of formula (I) included in the present invention include salts, solvates (including hydrates), complexes, polymorphs and crystal habits thereof, prodrugs, stereoisomers, geometric isomers, tautomeric forms, and isotopic variations of compounds of formula (I). Preferably, pharmaceutically acceptable derivatives of compounds of formula (I) comprise salts or solvates (including hydrates) of the compounds of formula (I).

The pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemi-salts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or (iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised. By the same token, salts of prodrugs of compounds of formula (I) can be prepared in an analogous manner.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds and salts of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see "Polymorphism in Pharmaceutical Solids" by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $-COO^-Na^+$, $-COO^-K^+$, or $-SO_3^-Na^+$) or non-ionic (such as $-N^-N^+(CH_3)_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula (I) include references to salts, solvates, multi-component complexes, prodrugs, liquid crystals, etc. thereof and to solvates, multi-component complexes and liquid crystals of salts thereof, etc.

As indicated above, so-called 'prodrugs' of the compounds of formula (I) are also within the scope of the invention. Thus certain derivatives of compounds of formula (I), which may have little or no pharmacological activity themselves, can be converted into compounds of formula (I) having the desired activity, for example by hydrolytic cleavage, when administered into, or onto, the body. Such derivatives are referred to as 'prodrugs'. Further information on the use of prodrugs may be found in "Pro-drugs as Novel Delivery Systems", Vol. 14, ACS Symposium Series (T. Higuchi and W. Stella) and "Bioreversible Carriers in Drug Design", Pergamon Press, 1987 (Ed. E. B. Roche, American Pharmaceutical Association).

Prodrugs in accordance with the invention can be produced by replacing appropriate functionalities present in the compounds of formula (I) with certain moieties known to those skilled in the art as 'pro-moieties' as described, for example, in "Design of Prodrugs" by H. Bundgaard (Elsevier, 1985).

Some examples of prodrugs in accordance with the invention include
(i) where the compound of formula (I) contains an alcohol functionality, the phosphate ester thereof, for example, a compound wherein the hydrogen of the alcohol functionality of the compound of formula (I) is replaced by $PO_3H_2$ (these prodrugs may be prepared by the methods laid out in WO 99/33815) and
(ii) where the compound of formula (I) contains a primary or secondary amino functionality ($-NH_2$ or $-NHR$ where $R \neq H$), an amide thereof, for example, a compound wherein, as the case may be, one or both hydrogens of the amino functionality of the compound of formula (I) is/are replaced by $(C_1-C_{10})$alkanoyl.

Moreover, certain compounds of formula (I) may themselves act as prodrugs of other compounds of formula (I).

Also included within the scope of the invention are metabolites of compounds of formula (I), that is, compounds formed in vivo upon administration of the drug. Thus within the scope of the invention are envisaged the metabolites of the compounds of formula (I) when formed in vivo.

Compounds of formula (I) or derivative herein defined containing one or more asymmetric carbon atoms can exist as two or more stereoisomers. Where a compound of formula (I) or derivative contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) or derivative containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (I) or derivatives, including compounds exhibiting more than one type of isomerism, and mixtures of one or more thereof. Also included are acid addition or base salts wherein the counter ion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) or derivative contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

The present invention includes all pharmaceutically acceptable isotopically-labelled compounds of formula (I) or derivatives herein defined, wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I) or derivative herein defined, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labelled compounds of formula (I) or derivatives herein defined can generally be prepared by conventional techniques known to those skilled in the art or by processes analogous to those described in the accompanying Examples and Preparations using an appropriate isotopically-labelled reagent in place of the non-labelled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of formula (I) or their derivatives herein defined should be assessed for their biopharmaceutical properties, such as solubility and solution stability (across pH), permeability, etc., in order to select the most appropriate dosage form and route of administration for treatment of the proposed indication.

Compounds (I) and derivatives herein defined of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

The compounds (I) and derivatives of the invention may be administered alone or in combination with one or more other compounds or derivatives of the invention or in combination with one or more other therapeutically active substances (drugs) (or as any combination thereof).

The compounds (I) and derivatives of the present invention may be administered in combination with COX inhibitors. Thus in a further aspect of the invention, there is provided a pharmaceutical product containing a progesterone receptor modulator and one or more COX inhibitors as a combined preparation for simultaneous, separate or sequential use in the treatment of endometriosis.

COX inhibitors useful for combining with the compounds of formula (I) and derivatives thereof of the present invention include, but are not limited to:

(i) ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenec, alclofenac, ibufenac, isoxepac, furofenac, tiopinac, zidometacin, acetyl salicylic acid, indometacin, piroxicam, tenoxicam, nabumetone, ketorolac, azapropazone, mefenamic acid, tolfenamic acid, diflunisal, podophyllotoxin derivatives, acemetacin, droxicam, floctafenine, oxyphenbutazone, phenylbutazone, proglumetacin, acemetacin, fentiazac, clidanac, oxipinac, mefenamic acid, meclofenamic acid, flufenamic acid, niflumic acid, flufenisal, sudoxicam, etodolac, piprofen, salicylic acid, choline magnesium trisalicylate, salicylate, benorylate, fentiazac, clopinac, feprazone, isoxicam and 2-fluoro-a-methyl[1,1'-biphenyl]-4-acetic acid, 4-(nitrooxy)butyl ester (See Wenk, et al., *Europ. J. Pharmacol.* 453:319-324 (2002));

(ii) meloxicam, (CAS registry number 71125-38-7; described in U.S. Pat. No. 4,233,299), or a pharmaceutically acceptable salt or prodrug thereof;
(iii) celecoxib (U.S. Pat. No. 5,466,823), valdecoxib (U.S. Pat. No. 5,633,272), deracoxib (U.S. Pat. No. 5,521,207), rofecoxib (U.S. Pat. No. 5,474,995), etoricoxib (International Patent Application Publication No. WO 98/03484), JTE-522 (Japanese Patent Application Publication No. 9052882), or a pharmaceutically acceptable salt or prodrug thereof;
(iv) Parecoxib (described in U.S. Pat. No. 5,932,598), which is a therapeutically effective prodrug of the tricyclic Cox-2 selective inhibitor valdecoxib (described in U.S. Pat. No. 5,633,272), in particular sodium parecoxib;
(v) ABT-963 (described in International Patent Application Publication No. WO 00/24719)
(vi) Nimesulide (described in U.S. Pat. No. 3,840,597), flosulide (discussed in J. Carter, *Exp. Opin. Ther. Patents,* 8(1), 21-29 (1997)), NS-398 (disclosed in U.S. Pat. No. 4,885,367), SD 8381 (described in U.S. Pat. No. 6,034, 256), BMS-347070 (described in U.S. Pat. No. 6,180,651), S-2474 (described in European Patent Publication No. 595546) and MK-966 (described in U.S. Pat. No. 5,968, 974);
(vii) darbufelone (Pfizer), CS-502 (Sankyo), LAS 34475 (Almirall Profesfarma), LAS 34555 (Almirall Profesfarma), S-33516 (Servier), SD 8381 (Pharmacia, described in U.S. Pat. No. 6,034,256), BMS-347070 (Bristol Myers Squibb, described in U.S. Pat. No. 6,180,651), MK-966 (Merck), L-783003 (Merck), T-614 (Toyama), D-1367 (Chiroscience), L-748731 (Merck), CT3 (Atlantic Pharmaceutical), CGP-28238 (Novartis), BF-389 (Biofor/Scherer), GR-253035 (Glaxo Wellcome), 6-dioxo-9H-purin-8-yl-cinnamic acid (Glaxo Wellcome), and S-2474 (Shionogi).

The compounds of formula (I) or derivatives as herein defined of the present invention may be administered in combination with an agent which lowers estrogen levels, or which antagonises the estrogen receptor. Thus, in a further aspect of the invention, there is provided a pharmaceutical product containing a compound of formula (I) or derivative as herein defined and one or more agents which lower estrogen levels, or antagonise the estrogen receptor, as a combined preparation for simultaneous, separate or sequential use in the treatment of endometriosis.

Agents which lower estrogen levels include gonadotropin releasing hormone (GnRH) agonists, GnRH antagonists and estrogen synthesis inhibitors. Agents which antagonise the estrogen receptor, i.e. estrogen receptor antagonists, include anti-estrogens, or agents which selectively agonise the beta subtype of the estrogen receptor (ERβ agonists).

GnRH agonists suitable for the present invention include leuprorelin (Prostap—Wyeth), buserelin (Suprefact—Shire), goserelin (Zoladex—Astra Zeneca), triptorelin (De-capeptyl—Ipsen), nafarelin (Synarel—Searle), deslorelin (Somagard—Shire), and histrelin/supprelin (Ortho Pharmaceutical Corp/Shire).

GnRH antagonists suitable for the present invention include teverelix (also known as antarelix), abarelix (Plenaxis—Praecis Pharmaceuticals Inc.), cetrorelix (Cetrotide—ASTA Medica), ganirelix (Orgalutran—Organon), ozarelix (Spectrum) and elagolix (Neurocrine Biosciences Inc).

Anti-estrogens suitable for the present invention include tamoxifen, Faslodex (Astra Zeneca), idoxifene (see Coombes et al. (1995) Cancer Res. 55, 1070-1074), raloxifene or EM-652 (Labrie, F et al, (2001) J steroid Biochem Mol Biol, 79, 213).

ERβ agonists suitable for the present invention include prinaberel (ERB-041) and ERB-196 (Wyeth).

Estrogen synthesis inhibitors suitable for the present invention include aromatase inhibitors. Examples of aromatase inhibitors include Formestane (4-OH androstenedione), Exemestane, Anastrozole (Arimidex) and Letroxole.

The compounds of formula (I) or derivative as herein defined of the present invention may be administered in combination with an alpha-2-delta ligand. Thus, in a further aspect of the invention, there is provided a pharmaceutical product containing a compound of formula (I) or derivative as herein defined and one or more alpha-2-delta ligands, as a combined preparation for simultaneous, separate or sequential use in the treatment of endometriosis.

Examples of alpha-2-delta ligands for use in the present invention are those compounds, or pharmaceutically acceptable salts thereof, generally or specifically disclosed in U.S. Pat. No. 4,024,175, particularly gabapentin, EP641330, particularly pregabalin, U.S. Pat. No. 5,563,175, WO-A-97/33858, WO-A-97/33859, WO-A-99/31057, WO-A-99/31074, WO-A-97/29101, WO-A-02/085839, particularly [(1R,5R,6S)-6-(aminomethyl)bicyclo[3.2.0]hept-6-yl]acetic acid, W O-A-99/31075, particularly 3-(1-aminomethyl-cyclohexylmethyl)-4H-[1,2,4]oxadiazol-5-one and C-[1-(1H-tetrazol-5-ylmethyl)-cycloheptyl]-methylamine, WO-A-99/21824, particularly (3S,4S)-(1-aminomethyl-3,4-dimethylcyclopentyl)-acetic acid, W O-A-01/90052, WO-A-01/28978, particularly (1α,3α,5α)(3-amino-methyl-bicyclo [3.2.0]hept-3-yl)-acetic acid, EP0641330, WO-A-98/17627, WO-A-00/76958, particularly (3S,5R)-3-aminomethyl-5-methyl-octanoic acid, WO-A-03/082807, particularly (3S, 5R)-3-amino-5-methyl-heptanoic acid, (3S,5R)-3-amino-5-methyl-nonanoic acid and (3S,5R)-3-amino-5-methyl-octanoic acid, WO-A-2004/039367, particularly (2S,4S)-4-(3-fluoro-phenoxymethyl)-pyrrolidine-2-carboxylic acid, (2S,4S)-4-(2,3-difluoro-benzyl)-pyrrolidine-2-carboxylic acid, (2S,4S)-4-(3-chlorophenoxy)proline and (2S,4S)-4-(3-fluorobenzyl)proline, EP1178034, EP1201240, WO-A-99/31074, WO-A-03/000642, WO-A-02/22568, WO-A-02/30871, WO-A-02/30881 WO-A-02/100392, WO-A-02/100347, WO-A-02/42414, WO-A-02/32736 and WO-A-02/28881, all of which are incorporated herein by reference.

Preferred alpha-2-delta ligands for use in the combination of the present invention include: gabapentin, pregabalin, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (1α,3α,5α)(3-amino-methyl-bicyclo [3.2.0]hept-3-yl)-acetic acid, (3S,5R)-3-aminomethyl-5-methyl-octanoic acid, (3S,5R)-3-amino-5-methyl-heptanoic acid, (3S,5R)-3-amino-5-methyl-nonanoic acid, (3S,5R)-3-amino-5-methyl-octanoic acid, (2S,4S)-4-(3-chlorophenoxy)proline and (2S,4S)-4-(3-fluorobenzyl)proline or pharmaceutically acceptable salts thereof.

Further preferred alpha-2-delta ligands for use in the combination of the present invention are (3S,5R)-3-amino-5-methyloctanoic acid, (3S,5R)-3-amino-5-methylnonanoic acid, (3R,4R,5R)-3-amino-4,5-dimethylheptanoic acid and (3R,4R,5R)-3-amino-4,5-dimethyloctanoic acid, and the pharmaceutically acceptable salts thereof.

Particularly preferred alpha-2-delta ligands for use in the combination of the present invention are selected from gabapentin, pregabalin, (1α,3α,5α)(3-amino-methyl-bicyclo [3.2.0]hept-3-yl)-acetic acid, (2S,4S)-4-(3-chlorophenoxy) proline and (2S,4S)-4-(3-fluorobenzyl)proline or pharmaceutically acceptable salts thereof.

Further preferred alpha-2-delta ligands for use in the combination of the present invention are gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-amino-5-methyl-nonanoic acid, (3R,4R,5R)-3-amino-4,5-dimethyl-heptanoic acid, (3R,4R,5R)-3-amino-4,5-dimethyl-octanoic acid, (3S,5R)-3-aminomethyl-6-cyclopropyl-5-methylhexanoic acid, (3S,5R)-3-aminomethyl-6-cyclobutyl-5-methylhexanoic acid and (3S,5R)-3-aminomethyl-6-cyclopentyl-5-methylhexanoic acid.

The contents of the published patent applications mentioned above, and in particular the general formulae of the therapeutically active compound of formula (I) or derivative as herein defined of the claims and exemplified compounds therein, are incorporated herein in their entirety by reference thereto.

The compounds of the present invention may also be administered in combination with any one or more of the following
(i) Aromatase inhibitor;
(ii) Estrogen receptor agonist;
(iii) Angiogenesis inhibitor;
(iv) VEGF inhibitor;
(v) Kinase inhibitor;
(vi) Protein farnesyl transferase inhibitor;
(vii) Androgen receptor modulator;
(viii) Androgen receptor agonists;
(ix) Androgen receptor antagonists;
(x) Prostanoid receptor agonist;
(xi) Prostanoid receptor antagonist;
(xi) Prostaglandin synthetase inhibitor;
(xii) Bioflavanoid;
(xiii) Alkylating agent;
(xiv) Microtubule modulator, e.g. Microtubule stabilizer;
(xv) Topoisomerase I inhibitor;
(xvi) Metalloprotease inhibitor;
(xvii) Progesterone modulator; or
(xviii) 17-β-hydroxysteroid dehydrogenase inhibitor.

Thus, in a further aspect of the invention, there is provided a pharmaceutical product containing a compound of formula (I) or derivative as herein defined and any one or more of the following
(i) Aromatase inhibitor;
(ii) Estrogen receptor agonist;
(iii) Angiogenesis inhibitor;
(iv) VEGF inhibitor;
(v) Kinase inhibitor;
(vi) Protein farnesyl transferase inhibitor;
(vii) Androgen receptor modulator;
(viii) Androgen receptor agonist;
(ix) Androgen receptor antagonist;
(x) Prostanoid receptor agonist;
(xi) Prostanoid receptor antagonist;
(xi) Prostaglandin synthetase inhibitor;
(xii) Bioflavanoid;
(xiii) Alkylating agent;
(xiv) Microtubule modulator, e.g. Microtubule stabilizer;
(xv) Topoisomerase I inhibitor;
(xvi) Metalloprotease inhibitor;
(xvii) Progesterone modulator; or
(xviii) 17-β-hydroxysteroid dehydrogenase inhibitor;
as a combined preparation for simultaneous, separate or sequential use in the treatment of endometriosis or uterine fibroids.

The compounds of the invention may have the advantage that they are more potent, have a longer duration of action, have a broader range of activity, are more stable, have fewer side effects or are more selective, or have other more useful properties than the compounds of the art.

Thus the invention provides:
(i) a compound of formula (I) or a pharmaceutically acceptable salt, solvate (including hydrate), or prodrug thereof, as herein defined;
(ii) a process for the preparation of a compound of formula (I) or a pharmaceutically acceptable salt, solvate (including hydrate), or prodrug thereof as herein defined;
(iii) a pharmaceutical formulation including a compound of formula (I) or a pharmaceutically acceptable salt, solvate (including hydrate), or prodrug thereof as herein defined, together with a pharmaceutically acceptable excipient, diluent or carrier;
(iv) a compound of formula (I) or a pharmaceutically acceptable salt, solvate (including hydrate), or prodrug thereof as herein defined or composition thereof, for use as a medicament;
(v) a compound of formula (I) or a pharmaceutically acceptable salt, solvate (including hydrate), or prodrug thereof as herein defined for use as a medicament for the treatment of a disorder which would benefit from progesterone receptor antagonism.
(vi) a compound of formula (I) or a pharmaceutically acceptable salt, solvate (including hydrate), or prodrug thereof as herein defined or composition thereof, for use in treating endometriosis, uterine fibroids (leiomyomata), menorrhagia, adenomyosis, primary and secondary dysmenorrhea (including symptoms of dyspareunia, dyschexia and chronic pelvic pain) or chronic pelvic pain syndrome;
(vii) a compound as in (vi) where the disease or disorder is endometriosis and/or uterine fibroids (leiomyomata);
(viii) the use of a compound of formula (I) or a pharmaceutically acceptable salt, solvate (including hydrate), or prodrug thereof as herein defined or composition thereof, for the manufacture of a medicament for the treatment of endometriosis, uterine fibroids (leiomyomata), menorrhagia, adenomyosis, primary and secondary dysmenorrhea (including symptoms of dyspareunia, dyschexia and chronic pelvic pain) or chronic pelvic pain syndrome;
(ix) use as in (viii) where the disease or disorder is endometriosis and/or uterine fibroids (leiomyomata);
(x) a method of treatment of a mammal to treat endometriosis, uterine fibroids (leiomyomata), menorrhagia, adenomyosis, primary and secondary dysmenorrhea (including symptoms of dyspareunia, dyschexia and chronic pelvic pain) or chronic pelvic pain syndrome including treating said mammal with an effective amount of compound of formula (I) or a pharmaceutically acceptable salt, solvate (including hydrate), or prodrug thereof as herein defined or composition thereof;
(xi) a method as in (x) where the disease or disorder is endometriosis and/or uterine fibroids (leiomyomata);
(xii) a compound of the formula (III), (IV), (V), (VI) or (VII);
(xiii) a combination as described herein;

(xiv) a compound, salt, solvate (including hydrate), prodrug, process, method of treatment, combination therapy, intermediate or pharmaceutical composition, substantially as described herein.

Other aspects of the invention will be apparent from the claims.

Generally, compounds of formula (I) or derivatives as herein defined of the invention will be administered as a formulation in association with one or more pharmaceutically acceptable excipients, diluents or carriers. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of the compounds of formula (I) or derivatives as herein defined of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

The compounds of formula (I) or derivatives as herein defined of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of formula (I) or derivatives as herein defined of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets", Vol. 1, by H. Lieberman and L. Lachman (Marcel Dekker, New York, 1980).

Consumable oral films are typically pliable water-soluble or water-swellable thin film dosage forms which may be rapidly dissolving or mucoadhesive and typically comprise a compound of formula (I) or derivative as herein defined, a film-forming polymer, a binder, a solvent, a humectant, a plasticiser, a stabiliser or emulsifier, a viscosity-modifying agent and a solvent. Some components of the formulation may perform more than one function.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of formula (I) or derivatives as herein defined of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) or derivatives as herein defined used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of formula (I) or derivatives as herein defined of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of formula (I) or derivatives as herein defined of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µL to 100 µL. A typical formulation may comprise a compound of formula (I) or derivative as herein defined, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

The compounds of formula (I) or derivatives as herein defined of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of formula (I) or derivatives as herein defined of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

The compounds of formula (I) or derivatives as herein defined of the invention may also be administered vaginally via a vaginal ring. Examples of formulations of vaginal ring are described in U.S. Pat. Nos. 5,972,372; 6,126,958; and 6,125,850. Use of the vaginal ring is timed to the cycle to which the compound is being administered, including a 28-day cycle. However, it can be inserted for a longer or shorter period of time. For example, the ring can be inserted into the vagina to remain in place for three consecutive weeks. During the fourth week, the vaginal ring is removed and menses occurs. The following week, a new ring can be inserted and worn for the next consecutive three weeks then removed for the next menses to occur. In an alternative regimen, the vaginal ring can be replaced weekly for three consecutive weeks, followed by a week without the ring during menses. Regimens including longer and shorter cycles are also envisaged.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound of formula (I) or derivative as herein defined in accordance with the invention, may conveniently be combined in the form of a kit suitable for coadministration of the compositions.

Thus the kit of the invention comprises two or more separate pharmaceutical compositions, at least one of which contains a compound of formula (I) or derivative as herein defined in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compound of formula (I) or derivative as herein defined of the invention is typically in the range <1 mg to 1000 mg depending, of course, on the mode of administration. For example, oral administration may require a total daily dose of from <1 mg to 1000 mg, while an intravenous dose may only require from <1 mg to 500 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

The terms "treating", "treat", or "treatment" as used herein are intended to embrace both prevention and control i.e., prophylactic, palliative and curative treatment of the indicated conditions.

As used herein, the terms "treating" and "to treat", mean to alleviate symptoms, eliminate the causation either on a temporary or permanent basis, or to prevent or slow the appearance of symptoms. The term "treatment" includes alleviation, elimination of causation (either on a temporary or permanent basis) of, or prevention of symptoms and disorders associated with endometriosis and/or uterine leiomyoma. The treatment may be a pre-treatment as well as a treatment at the on-set of symptoms.

The compounds of the present invention should be useful for the treatment of gynecological symptoms of painful menstruation (dysmenorrhea), painful intercourse (dyspareunia), painful defecation (dyzchexia) or micturition (dysuria) provoked by menstruation, chronic pelvic pain (constant or cyclic painful symptoms present for more than six months), excessive menstrual blood loss (menorrhagia), frequent periods (polymenorrhagia) or infrequent or irregular periods (oligoamenorrhoea or amenorrhoea) either occurring in the absence of specific pathology (dysfunctional uterine bleeding and/or primary dysmenorrhea), or in association with endometriosis, adenomyosis, polycystic ovarian syndrome, or uterine fibroids (leiomyomata).

It is intended that the term treatment encompasses not only the management of the pain symptoms associated with the abovementioned conditions, but also modification of the disease progression itself, i.e. a clinically meaningful benefit to the patients is achieved. Modification of disease progression may result in reduction or elimination of pain. More preferably, modification of disease progression may result in reduction or elimination of pain, and prolonged intervals to symptom onset. Even more preferably, modification of disease progression may result in reduction or elimination of pain, prolonged intervals to symptom onset, and reduction in the need for surgery. Most preferably, modification of disease progression may result in reduction or elimination of pain, prolonged intervals to symptom onset, a reduction in the need of surgery, and preserved and/or improved fertility.

The compounds of formula (I) or derivatives as herein defined of the present invention may be tested in the screens set out below:

1.0 In vitro Functional Assay for Progesterone Receptor (PR) Antagonists, Agonists and Modulators The assay for PR antagonism takes advantage of the extensively reported modulation of alkaline phosphatase (AP) expression in human breast T47D mammary carcinoma cells {Beck et al., D. P. (1993). The progesterone antagonist RU486 acquires agonist activity upon stimulation of cAMP signalling pathways. Proc Natl Acad Sci USA 90, 4441-4445; Fensome et al. (2002). New progesterone receptor antagonists: 3,3-disubstituted-5-aryloxindoles. Bioorg Med Chem Lett 12, 3487-3490; Zhang et al., (2002a). 6-Aryl-1,4-dihydro-benzo d1,3oxazin-2-ones: a novel class of potent, selective, and orally active nonsteroidal progesterone receptor antagonists. Journal of Medicinal Chemistry 45, 4379-4382; Zhang et al., (2003). Novel 6-aryl-1,4-dihydrobenzo d oxazine-2-thiones as potent, selective, and orally active nonsteroidal progesterone receptor agonists. Bioorganic & Medicinal Chemistry Letters 13, 1313-1316; Zhang et al., (2002b). Potent nonsteroidal progesterone receptor agonists: synthesis and SAR study of 6-aryl benzoxazines. Bioorganic & Medicinal Chemistry Letters 12, 787-790; Zhang, Z. et al., (2000). In vitro characterization of trimegestone: a new potent and selective progestin. Steroids 65, 637-643}. In the presence of progesterone or progesterone receptor agonists endogenous AP expression is induced in T47D cells and is inhibited by compounds possessing PR antagonistic activity. In the absence of progesterone any agonist activity is also observed as an induction of AP activity. By running the assay in two formats (+/−progesterone (P4)), compounds behaving as PR antagonists, agonists, partial agonists or modulators with mixed agonist/antagonist activity can be identified.

The equipment required to grow T47D cells and perform the progesterone-induced AP assay are outlined below.

Equipment List

Plates:

| | | |
|---|---|---|
| 96-well v-bottom polypropylene plates | Greiner | 651201 |
| 384 well polypropylene plates | Matrix | 4314 |
| 384-well white, polypropylene lidded plates (tissue culture treated) | Greiner | 781080-PFI |

PlateMate Plus:

| | | |
|---|---|---|
| 0.5 μL to 30 μL DART Tips | Matrix | 5316 |

LJL Analyst:

| | |
|---|---|
| Multidrop: with sterile head | Thermolabsystems |
| Cedex: AS20 cell counter | Innovatis |

General Lab Equipment:
- Pipettes ranging from 2 μL to 5000 μL
- 50 mL and 15 mL centrifuge tubes
- Class II laminar flow hood
- −80° C. freezer The materials required to grow T47D cells and perform the progesterone-induced AP assay are outlined in Table 1.

TABLE 1

| Reagent | Supplier | Catalogue number |
|---|---|---|
| T47D human mammary carcinoma cells | American tissue culture collections; http://www.atcc.org/ | HTB-133 |
| Dimethyl sulphoxide (DMSO) | Sigma | D2650 |
| Dulbecco's modified Eagle's Medium (DMEM) | Gibco | 21969-035 |
| DMEM without phenol red | Gibco | 31053-028 |
| L-Glutamine, 200 mM | Gibco | |
| Charcoal stripped foetal calf serum (CS-FCS) | Globepharm | HYC-001-325B (lot. APD21146) |
| Phosphate buffered saline (PBS) | Gibco | 14190-094 |
| Foetal bovine serum (FBS) | PAA | A15-245 |
| TROPIX CSPD Ready-to-use Emerald II reagent | Applied Biosystems | CD100RY |
| Progesterone (P4) | Sigma | P-6149 |
| Pluronic-F127 | Molecular Probes | P6867 |
| RU486 (Mifepristone) | Sigma | M-8046 |

Growth medium: DMEM+Red (21969-035)
- 50 mL FCS (10%)
- 6 mL Glutamine (2 mM)

Assay medium: DMEM−Red (31053-028)
- 25 mL Charcoal Stripped FCS (5%)
- 6 mL Glutamine (2 mM)

Briefly, T47D cells are grown by propagating in DMEM with phenol red+10% FCS+2 mM Glutamine at 37° C./5% $CO_2$. At 70-80% confluence, the media is exchanged for phenol red free DMEM+5% CS-FCS (Assay media). Cells are incubated overnight in assay media then harvested and frozen in assay media containing 10% DMSO at 1.5e7 cells/mL in 2 mL aliquots using a Planer and immediately stored in liquid nitrogen. Vials are removed from liquid nitrogen storage and immediately thawed in a water bath at 37° C. The cell suspension is added dropwise to 20 mL of assay media, then the tube centrifuged at 1000 rpm for 4 minutes, the supernatant is discarded and the pellet re-suspended in 20 mL assay media. T47D cells are then plated at 8750 cells/well in 35 μL assay media in sufficient white solid 384 well TC plates for the assay. For the agonist format assay a further 10 μL of assay media is added to each well. These plates are then cultured for 3-6 hours at 37° C./5% $CO_2$ before compound addition.

Preparation of Test Substances

Test substances are prepared by in 100% DMSO, half log concentrations from 4 mM in 384 well plates 5 μL/well (referred to here as 'grandmother plates'). Progesterone is 100 μM made up in ethanol and PBS (i.e. add 1 mL ethanol to progesterone initially to help dissolving) and stored in 0.5-1 mL aliquots at −20° C.

| Buffer | Diluent |
|---|---|
| PBS + 0.05% Pluronic F1267 | PBS + 2.5% DMSO + 0.05% Pluronic F1267 |

Using a multidrop (Thermolabsystems), 60 μL/well of buffer is added to a 384 well plate—this will be the 'mother plate'. Add 45 μL well buffer to grandmother plate using the multidrop (=400 μM 10% DMSO dilution). Mixed and spun to remove air bubbles.

20 μL is taken from the grandmother plate (400 μM 10% DMSO) and added to the mother plate (=100 μM 2.5% DMSO). Mixed and spun to remove air bubbles.

Preparation of Max/Min:

The Max's & Min's are prepared as below in Falcon tubes and then 100 μL is transferred to the appropriate wells of a 384 well plate:

Agonist Max: (Solid Block on Plate Map) 10 μM Progesterone (FAC 1 μM)
- 500 μL of 100 μM progesterone
- 4.5 mL diluent Agonist Min: (Checker Pattern on Plate Map) Diluent
- Diluent Antagonist Max: (Solid Block on Plate Map) Diluent
- Diluent Antagonist Min: (Checker Pattern on Plate Map) 1 μM RU-486 (FAC 0.1 μM)
- 50 μL of 0.2 mM RU-486
- 10 mL Diluent Addition of Test Substance to Cell Plates
- The PlateMate Plus was used to add 5 μL MAX/MIN to cell plates
- Then 5 μL test substances are added from the mother plate (after removing max/min PlateMate tips: columns 1 and 24)
- See FIG. 1 below.

Addition of Agonist (5 nM Progesterone FAC) for Antagonist Format Only 25 nM progesterone in assay media is prepared from 100 μM stock (12.5 μL progesterone/50 mL media), from which 10 μL per well is transferred to the assay plate using the PlateMate Plus (already containing cells & compound).

The cell plates are incubated @ 37° C., 5% $CO_2$ overnight (at least 16 hours). Then:
- Tap out media from cell plates and drain on tissue
- Wash with PBS 40 μL/well
- Tap out PBS, drain on tissue
- Freeze for 15 minutes in a −80° C. freezer
- Thaw in a tissue culture incubator (15 minutes)
- Freeze 15 minutes in a −80° C. freezer (may be stored for at least one week without degradation of signal)

Thaw in tissue culture incubator for 5 minutes and wipe moisture from plates

Add 10 μL/well TROPIX CSPD Ready-to-use Emerald II reagent using the multidrop

Incubate 1 hour in foil at room temperature

Read on LJL Analyst luminescence counter.

In the agonist format, sigmoid fitting of the results expressed as alkaline phosphatase induction (% of maximal progesterone response) by the test substances is achieved and an $EC_{50}$ is determined. In the antagonist format, results are expressed as alkaline phosphatase inhibition by the test compounds and an $IC_{50}$ is determined % Inhibition The mean minimum is calculated and subtracted from all other readings The mean maximum is calculated and % inhibition calculated i.e. reading/X×100=% response (R) and 100−R=% inhibition The $EC_{50}$ value is defined as the drug concentration required to produce a 50% induction of AP activity compared with 5 nM progesterone alone. Test substances with full agonism achieve 100% of the response of progesterone whereas partial agonists induce AP activity to a level which is sub-maximal to that induced by progesterone. In the antagonist format, the $IC_{50}$ value is defined as the drug concentration required to produce a 50% inhibition of AP activity compared with 5 nM progesterone alone.

$K_i$ calculation was carried out on the resulting $IC_{50}$ data using the Cheng-Prusoff equation. In binding assays the concentration of antagonist required to displace 50% of a radiolabelled ligand from a receptor preparation is measured as $IC_{50}$. This is dependent on the concentration of radiolabelled ligand and as such is converted to Ki using the Cheng-Prusoff equation below. $K_i$ is an estimation of the concentration of antagonist at which 50% of the receptors are occupied.

$$K_i = IC_{50}/1+(L/K_d)$$

L=ligand concentration $K_d$=equilibrium dissociation constant for ligand

The Cheng-Prusoff equation used in binding assays is often used to calculate a $K_i$ derived from $IC_{50}$ for functional assays substituting agonist concentration (A) for L and the agonist $EC_{50}$ for $K_d$.

$$K_i = IC_{50}/1+(A/EC_{50})$$

A=agonist concentration $EC_{50}$=agonist $EC_{50}$

For the purposes of substances exemplified here, the Ki values are less than 5 μM. In a preferred embodiment, the Ki value is less than 500 nM. In a more preferred embodiment, the Ki value is less than 50 nM.

The routes below, including those mentioned in the Examples and Preparations, illustrate methods of synthesising compounds of formula (I) and certain derivatives thereof. The skilled person will appreciate that the compounds of formula (I) or derivatives as herein defined of the invention, and intermediates thereto, could be made by methods other than those specifically described herein, for example by adaptation of the methods described herein, for example by methods known in the art. Suitable guides to synthesis, functional group interconversions, use of protecting groups, etc., are for example:

"Comprehensive Organic Transformations" by R C Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by R K Mackie and D M Smith, Longman (1982); "Protective Groups in Organic Synthesis" by T W Greene and P G M Wuts, John Wiley and Sons, Inc. (1999); and "Protecting Groups" by P J, Kocienski, Georg Thieme Verlag (1994); and any updated versions of said standard works.

The present invention also encompasses any one or more of these processes for preparing the compounds of formula (I) or derivatives as herein defined, in addition to any novel intermediates used therein.

In the following general methods the substituents are as previously defined for a compound of formula (I) or derivative as herein defined unless otherwise stated.

Scheme 1

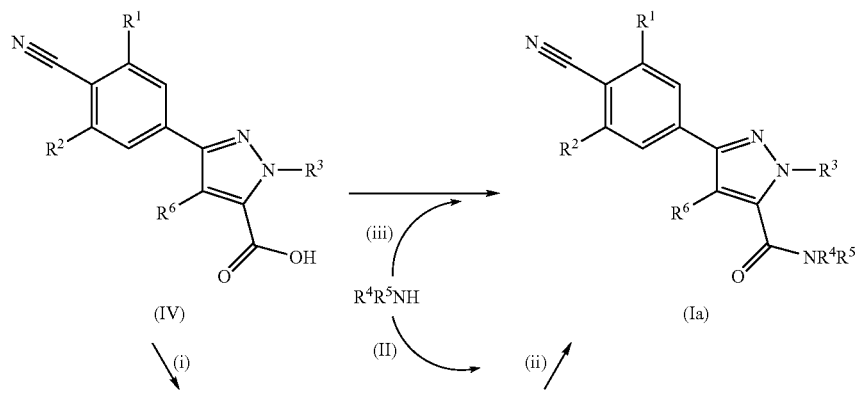

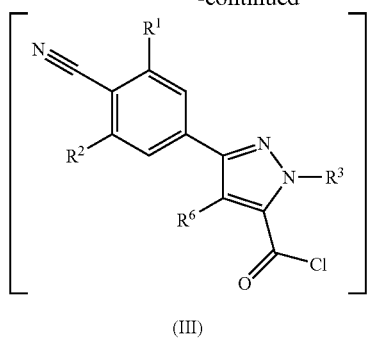

(III)

The compounds of formula (Ia) can be prepared from the compounds of formula (III) and formula (II) by in situ acylation in the presence of a suitable base, such as pyridine or triethylamine (step (ii)). Typical conditions comprise using from 1 to 2 molar equivalents of a compound of formula (II), from 1 to 5 molar equivalents of pyridine, in an organic solvent, at a temperature of from −20 to 80° C. Preferred conditions comprise 1.2 molar equivalents of a compound of formula (II) and 2 molar equivalents of triethylamine in 2-methyltetrahydrofuran, at ambient room temperature.

The compounds of formula (III) can be prepared from the compounds of formula (IV) by acid chloride formation with a suitable reagent, such as thionyl chloride or oxalyl chloride (step (i)). Typical conditions comprise an excess of thionyl chloride at a temperature of from 20 to 80° C. Preferred conditions comprise an excess of thionyl chloride at a temperature of 80° C.

Alternatively, the compounds of formula (Ia) can be prepared from the compounds of formula (IV) and formula (II) by amide coupling in the presence of a suitable coupling reagent, such as 1-propanephosphonic acid cyclic anhydride, 1-hydroxybenzotriazole hydrate, 1,1'-carbonyldiimidazole or O-benzotriazol-1-yl-N,N,N',N'-tetramethyluronium hexafluorophosphate, and a suitable base, such as triethylamine or pyridine, in an organic solvent (step (iii)). Typical conditions comprise using from 1 to 3 molar equivalents of a compound of formula (II), from 1 to 3 molar equivalents of O-benzotriazol-1-yl-N,N,N',N'-tetramethyluronium hexafluorophosphate and from 1 to 5 molar equivalents of pyridine, in 2-methyltetrahydrofuran, at a temperature of from 0° C. to 80° C. Preferred conditions comprise 1.3 molar equivalents of a compound of formula (II), 2 molar equivalents of O-benzotriazol-1-yl-N,N,N',N'-tetramethyluronium hexafluorophosphate and 3 molar equivalents of pyridine, in 2-methyltetrahydrofuran, at a temperature of 80° C.

Scheme 2

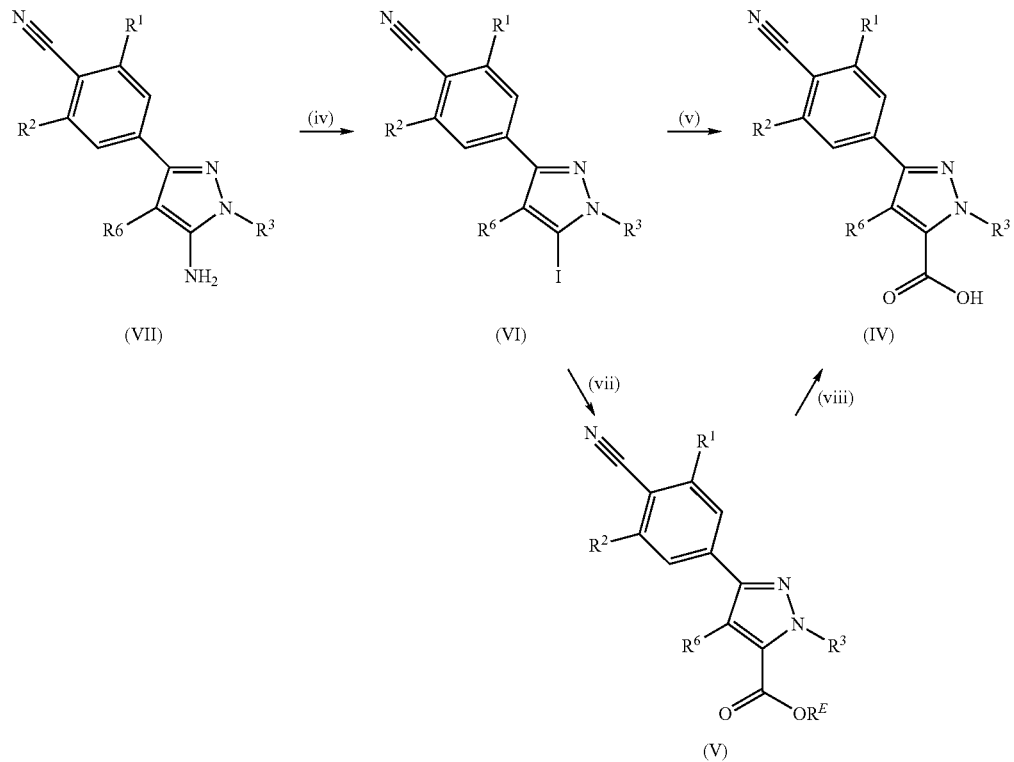

The compounds of formula (IV) can be prepared from the compounds of formula (VI) by carboxylation with carbon dioxide in the presence of a suitable base, such as n-butyl-lithium, sec-butyllithium or tert-butyllithium (step (v)). Typical conditions comprise using an excess of carbon dioxide in the presence of from 1 to 3 molar equivalents of n-butyl-lithium, in an organic solvent, at a temperature of from −100 to 20° C. Preferred conditions comprise using an excess of carbon dioxide in the presence of 1.5 molar equivalents of n-butyllithium, in tetrahydrofuran, at a temperature of −78° C.

Alternatively, the compounds of formula (IV) can be prepared from the compounds of formula (V) (where $R^E$ is a suitable ester-forming group, e.g. $C_{1-10}$ alkyl, phenyl optionally substituted by from 1 to 3 substituents each independently selected from $C_{1-6}$ alkyl, halo and nitro, or phenylmethyl optionally substituted in the phenyl ring by from 1 to 3 substituents each independently selected from $C_{1-6}$ alkyl, halo and nitro) by hydrolysis with a suitable base, such as sodium hydroxide or lithium hydroxide (step (viii)). Typical conditions comprise using from 1 to 5 molar equivalents of sodium hydroxide in a suitable protic solvent and water, at a temperature of from 20 to 100° C. Preferred conditions comprise 1.5 molar equivalents of sodium hydroxide in a water/methanol mix at a temperature of 100° C.

The compounds of formula (V) can be prepared from the compounds of formula (VI) by carbonylation with a carbon monoxide source in the presence of a suitable catalyst and base, using a suitable alcohol as solvent (step (vii)). Typical conditions comprise using from 0.01 to 0.20 molar equivalents of [1,1'-bis(diphenylphosphino)ferrocene] palladium (II) chloride and from 1 to 5 molar equivalents of triethylamine, in methanol, charged to between 15 and 300 psi (103 to 2070 kPa) with carbon monoxide, at a temperature of from 20 to 150° C. Preferred conditions comprise using 0.05 molar equivalents of [1,1'-bis(diphenylphosphino)ferrocene] palladium (II) chloride and 2 molar equivalents of triethylamine, in methanol, charged to 100 psi (690 kPa) with carbon monoxide, at a temperature of 100° C.

The compounds of formula (VI) can be prepared from the compounds of formula (VII) by a Sandmeyer reaction with a suitable reagent, such as ᵗbutyl nitrite, isoamyl nitrite or a sodium nitrite, in the presence of a suitable acid, such as acetic acid or concentrated sulphuric acid, and in the presence of a suitable iodide source, such as potassium iodide, copper iodide or diiodomethane. Typical conditions comprise using from 1 to 5 molar equivalents of ᵗbutyl nitrite in the presence of from 1 to 10 molar equivalents of acetic acid and from 1 to 5 molar equivalents of potassium iodide, in a suitable solvent, at a temperature of from −40 to 80° C. Preferred conditions comprise 2.5 molar equivalents of ᵗbutyl nitrite in the presence of 3 molar equivalents of acetic acid and 2.5 molar equivalents of potassium iodide, in acetonitrile and water, at ambient room temperature.

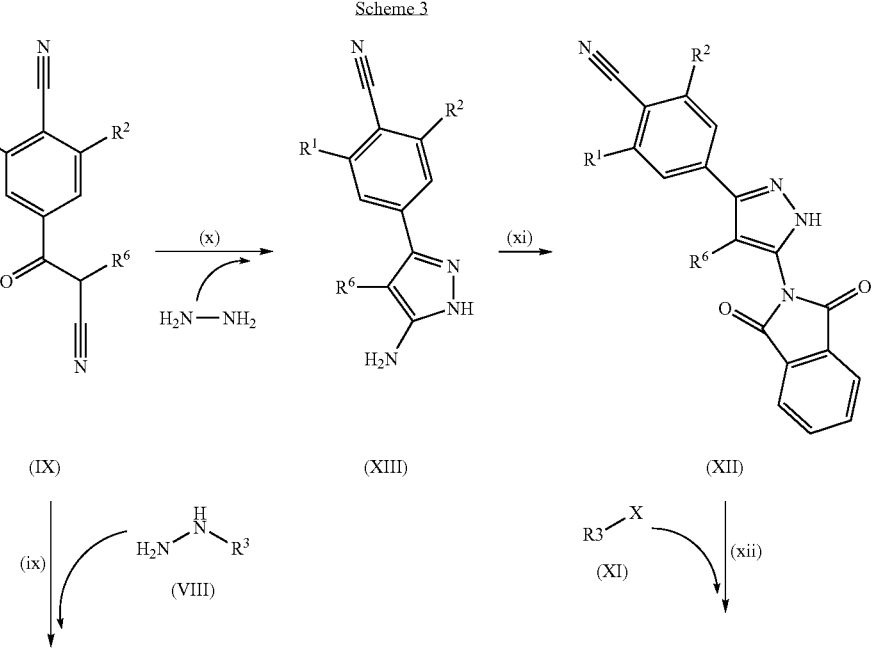

Scheme 3

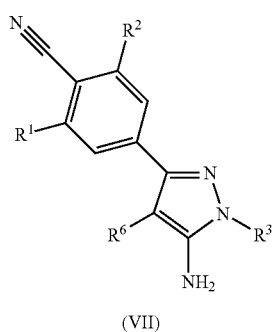 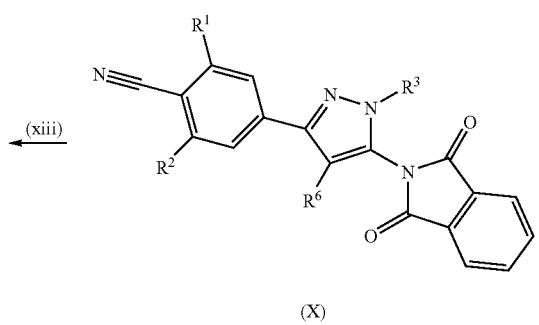

(where X is a suitable leaving group, such as chloro, iodo, bromo, methanesulphonyloxy or tosyl).

The compounds of formula (VII) can be prepared from the compounds of formula (VIII) and formula (IX) by pyrazole ring formation in the presence of a suitable base, such as triethylamine or diisopropylethylamine, and an acid, such as acetic acid, with or without a catalytic amount of a strong acid, such as trifluoroacetic acid, in a suitable organic solvent (step (ix)). Typical conditions comprise using from 1 to 10 molar equivalents of a compound of formula (VIII), from 1 to 20 molar equivalents of diisopropylethylamine, from 6 to 60 molar equivalents of acetic acid, in ethanol, at from 0° C. to 78° C. Preferred conditions comprise 1.1 molar equivalents of a compound of formula (VIII), 2 molar equivalents of diisopropylethylamine, and 6 molar equivalents of acetic acid, in ethanol at 60° C.

Alternatively, the compounds of formula (VII) can be prepared from the compounds of formula (X) by deprotection in the presence of a suitable hydrazine reagent, such as hydrazine hydrate or methylhydrazine, in a suitable organic solvent (step (xiii)). Typical conditions comprise using from 1 to 5 molar equivalents of methylhydrazine, in tetrahydrofuran, at from −20° C. to 67° C. Preferred conditions comprise 1 molar equivalent of methylhydrazine, in tetrahydrofuran, at ambient room temperature.

The compounds of formula (X) can be prepared from the compounds of formula (XI) and formula (XII) by alkylation in the presence of a suitable base (such as potassium carbonate, sodium carbonate, potassium tert butoxide or sodium hydride) in a suitable organic solvent (step (xii)). Typical conditions comprise using from 1 to 3 molar equivalents of a compound of formula (XI), and from 1 to 5 molar equivalents of potassium carbonate, in acetonitrile, at from 0 to 82° C. Preferred conditions comprise 1.1 molar equivalents of a compound of formula (XI), and 3 molar equivalents of potassium carbonate, in acetonitrile, at 80° C.

The compounds of formula (XII) can be prepared from the compounds of formula (XIII), by protection, using phthalic anhydride in a suitable organic solvent (step (xi)). Typical conditions comprise using from 1 to 3 molar equivalents of phthalic anhydride, in 1,4-dioxan, at from −20° C. to 100° C. Preferred conditions comprise 1.14 molar equivalents of phthalic anhydride, in 1,4-dioxan, at ambient room temperature.

The compounds of formula (XIII) can be prepared from the compounds of formula (IX) and hydrazine by pyrazole formation in the presence of an acid catalyst, such as acetic acid or trifluoroacetic acid, in an organic solvent (step (x)). Typical conditions comprise using from 1 to 3 molar equivalents of hydrazine hydrate, and from 0.01 to 0.2 molar equivalents of trifluoroacetic acid, in ethanol, at from −20° C. to 78° C. Preferred conditions comprise using 1.1 molar equivalents of hydrazine hydrate and 10% trifluoroacetic acid, in ethanol, at ambient room temperature.

Scheme 4

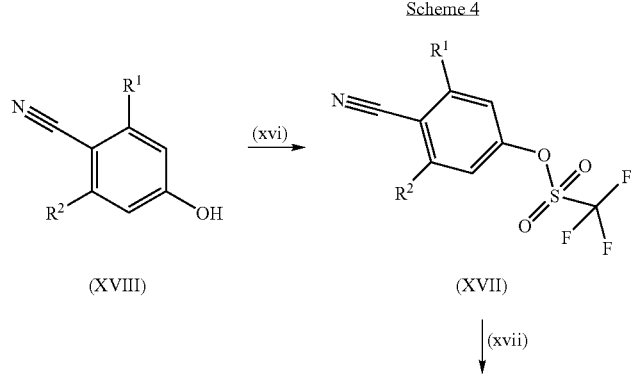

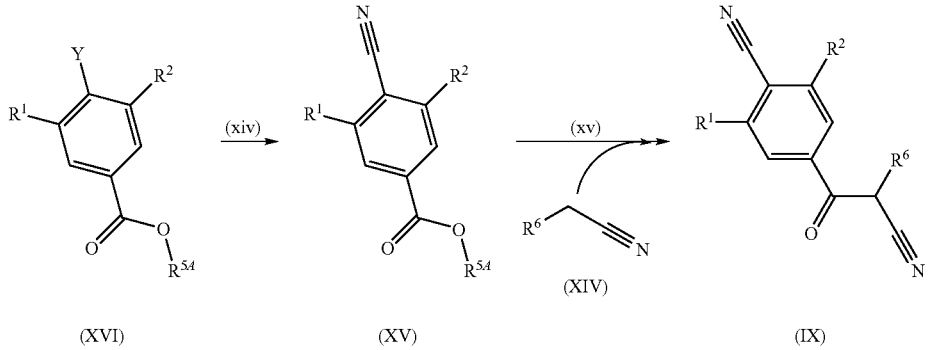

(where Y is a suitable halide or triflate and $R^{5A}$ is a suitable ester-forming group, e.g. $C_{1-10}$ alkyl, phenyl optionally substituted by from 1 to 3 substituents each independently selected from $C_{1-6}$ alkyl, halo and nitro, or phenylmethyl optionally substituted in the phenyl ring by from 1 to 3 substituents each independently selected from $C_{1-6}$ alkyl, halo and nitro).

The compounds of formulae (XVI) and (XVIII) are known compounds.

The compounds of formula (IX) can be prepared from the compounds of formula (XIV) and (XV) by α-cyano-ketone formation in the presence of a base, such as lithium diisopropylamide, potassium tert butoxide or sodium hydride, in an organic solvent (step (xv)). Typical conditions comprise using from 1 to 3 molar equivalents of a compound of formula (XIV) and from 1 to 3 molar equivalents of lithium diisopropylamide, in tetrahydrofuran, at from −100° C. to 25° C. Preferred conditions comprise 1 molar equivalent of a compound of formula (XIV) and 1.5 molar equivalents of lithium diisopropylamide, in tetrahydrofuran at −78° C.

The compounds of formula (XV) are known compounds and can be prepared from the compounds of formula (XVI) cyanation with a suitable cyanide source, such as zinc cyanide, in the presence of a suitable palladium catalyst, in a suitable organic solvent (step (xiv)). Typical conditions comprise using from 0.5 to 2 molar equivalents of zinc cyanide, from 0.01 to 0.2 molar equivalents of tris-(dibenzylideneacetone) dipalladium and from 0.02 to 0.3 molar equivalents of 1,1'bis(diphenylphosphino)ferrocene, in dimethylformamide, at from 25° C. to 153° C. Preferred conditions comprise 0.6 molar equivalents of zinc cyanide, 0.1 molar equivalents tris-(dibenzylideneacetone) dipalladium and 0.2 molar equivalents 1,1'bis(diphenylphosphino)ferrocene, in dimethylformamide, at 153° C.

Alternatively, the compounds of formula (XV) can be prepared from the compounds of formula (XVII) by carbonylation with a carbon monoxide source in the presence of a suitable catalyst and base, using a suitable alcohol as solvent (step (xvii)). Typical conditions comprise using from 0.01 to 0.20 molar equivalents of [1,1'-bis(diphenylphosphino)ferrocene] palladium (II) chloride and from 1 to 5 equivalents of triethylamine, in methanol, charged to between 15 and 300 psi (103 to 2070 kPa) with carbon monoxide, at a temperature of from 20 to 150° C. Preferred conditions comprise 0.05 molar equivalents of [1,1'-bis(diphenylphosphino)ferrocene] palladium (II) chloride and 2 molar equivalents of triethylamine, in methanol, charged to 100 psi (690 kPa) with carbon monoxide, at a temperature of 100° C.

The compounds of formula (XVII) can be prepared from the compounds of formula (XVIII) by triflation with a suitable agent, such as trifluoromethane sulfonic anhydride, in the presence of a suitable base, such as triethylamine or pyridine (step (xvi)). Typical conditions comprise using from 1 to 2 molar equivalents of trifluoromethane sulfonic anhydride and from 1 to 5 molar equivalents of base, in an organic solvent, at a temperature of from −78° C. to 0° C. Preferred conditions comprise 1.2 molar equivalents of trifluoromethane sulfonic anhydride and 2 molar equivalents of triethylamine, in dichloromethane at −15° C.

Scheme 5

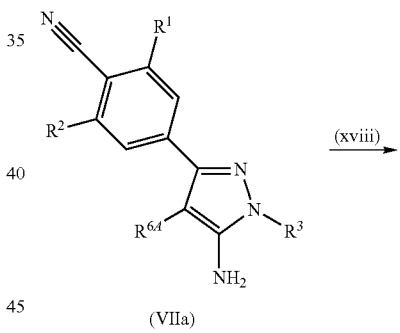

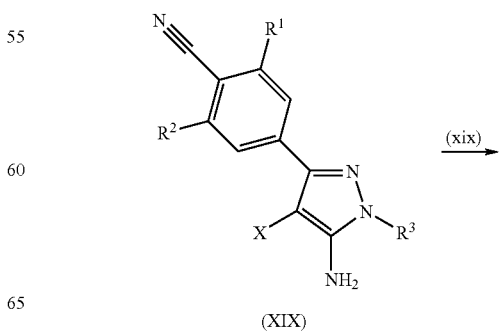

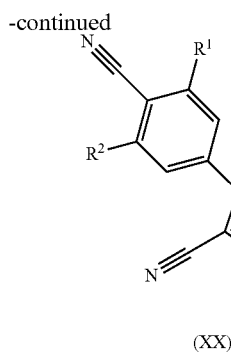

Where $R^{64}$ is hydrogen.
X is a suitable halide such as chlorine or iodine.

The compounds of formula (XX) can be prepared from the compounds of formula (XIX) by cyanation with a suitable cyanide source, such as zinc cyanide, in the presence of a suitable palladium catalyst, in a suitable organic solvent (step (xix)). Typical conditions comprise using from 0.5 to 2 molar equivalents of zinc cyanide, from 0.01 to 0.2 molar equivalents of tris-(dibenzylideneacetone) dipalladium and from 0.02 to 0.3 molar equivalents of 1,1'bis(diphenylphosphino) ferrocene, in dimethylformamide, at a temperature of from 25° C. to 153° C. Preferred conditions comprise 0.6 molar equivalents of zinc cyanide, 0.1 molar equivalents tris-(dibenzylideneacetone) dipalladium and 0.2 molar equivalents 1,1'bis(diphenylphosphino)ferrocene, in dimethylformamide, at 153° C.

The compounds of formula (XIX) can be prepared from the compounds of Formula (VIIa) by halogenation with a suitable reagent such as N-iodosuccimide (step (xviii)). Typical conditions comprise using from 1 to 2 molar equivalents of N-iodosuccimide in an organic solvent, at a temperature of from 20 to 100° C. Preferred conditions comprise 1.2 molar equivalents of N-iodosuccimide in acetonitrile at 82° C.

Alternatively, when X is chloride, the compounds of formula (XIX) can be prepared from the compounds of Formula (VIIa) by halogenation with a suitable reagent, such potassium chloride, in the presence of Oxone® (trade mark) (potassium peroxymonosulfate) Typical conditions comprise using from 1 to 2 molar equivalents of potassium chloride and from 1 to 2 molar equivalents of Oxone® in an organic solvent, at a temperature of from 0 to 80° C. Preferred conditions comprise 1.1 molar equivalents of potassium chloride and 1.1 molar equivalents of Oxone® in acetonitrile at 20° C.

The Preparations and Examples that follow illustrate the invention but do not limit the invention in any way. All starting materials are available commercially or are described in the literature. All temperatures are in ° C. Flash column chromatography was carried out using Merck silica gel 60 (9385). Thin layer chromatography (TLC) was carried out on Merck silica gel 60 plates (5729). "$R_f$" represents the distance traveled by a compound divided by the distance traveled by the solvent front on a TLC plate. Melting points were determined using a Gallenkamp MPD350 apparatus and are uncorrected. NMR was carried out using a Varian-Unity Inova 400 MHz NMR spectrometer or a Varian Mercury 400 MHz NMR spectrometer. Mass spectroscopy was carried out using a Finnigan Navigator single quadrupole electrospray mass spectrometer or a Finnigan aQa APCI mass spectrometer.

Where it is stated that compounds were prepared in the manner described for an earlier Preparation or Example, the skilled person will appreciate that reaction times, number of equivalents of reagents and reaction temperatures may be modified for each specific reaction, and that it may nevertheless be necessary or desirable to employ different work-up or purification conditions.

The invention is illustrated by the following non-limiting Examples in which the following abbreviations and definitions are used:
APCI atmospheric pressure chemical ionisation mass spectrum
$CDCl_3$ deuterated chloroform
$CD_3OD$ deuterated methanol
$(CD_3)_2SO$ deuterated dimethyl sulphoxide
δ chemical shift
d doublet
g grams
ESCI electrospray ionisation
HPLC high pressure liquid chromatography
LCMS low resolution mass spectrum
M molar
m multiplet
mg milligrams
MHz mega hertz
mins minutes
mL millilitres
μL microlitres
mm millimetres
mmol milli moles
mol moles
MS mass spectrometry
m/z mass spectrum peak
NMR nuclear magnetic resonance
q quartet
$R^t$ retention time
singlet
t triplet
TFA trifluoroacetic acid Where singleton compounds have been analysed by LCMS, there are six methods used. These are illustrated below.
System 1—6 Minute Basic Run:
A: 0.1% ammonium hydroxide in water
B: 0.1% ammonium hydroxide in acetonitrile
Column: C18 phase Fortis 50×4.6 mm with 5 micron particle size
Gradient: 95-5% A over 3 min, 1 min hold, 1 mL/min
UV: 210 nm-450 nm DAD
Temperature: 50° C.
System 2—2 Minute Acidic Run:
A: 0.1% formic acid in water
B: 0.1% formic acid in acetonitrile
Column: C18 phase Fortis Pace 20×2.1 mm with 3 micron particle size
Gradient: 70-2% A over 1.8 min, 0.2 min hold, 1.8 mL/min
UV: 210 nm-450 nm DAD
Temperature: 75° C.
System 3—Mass Spec:
ESCI: MS
Solvent 20 mM Ammonia 1 minute run
System 4—6 Minute Acidic Run:
A: 0.1% formic acid in water
B: 0.1% formic acid in acetonitrile
Column: C18 phase Phenomenex Luna 50×4.6 mm with 5 micron particle size
Gradient: 95-5% A over 3 min, 1 min hold, 1 mL/min
UV: 210 nm-450 nm DAD
Temperature: 50° C.

System 5—5 Minute Acidic Run:
A 0.0375% TFA in water
B 0.01875% TFA in acetonitrile
Column Ymc ODS-AQ 50 mm×2 mm with 5 micron particle size
Gradient: 90-10% A over 4.7 min, 1 min hold, 0.8 mL/min
Temperature: 50° C.
System 6—5 Minute Acidic Run:
A 0.0375% TFA in water
B 0.01875% TFA in acetonitrile
Column Ymc ODS-AQ 50 mm×2 mm with 5 micron particle size
Gradient: 99-0% A over 4.7 min, 1 min hold, 0.8 mL/min
Temperature: 50° C.
Mass Spectrometer Model: Agilent 1956A
Ionization Mode: API-ES
Polarity: Positive Where singleton compounds have been purified by High Performance Liquid Chromatography, unless otherwise stated, one of two methods were used, and these are shown below.

|  | Method a | Method b |
| --- | --- | --- |
| Column | Sunfire C18 4.6 × 50 mm id | Xterra 4.6 × 50 mm id |
| Temperature | Ambient | Ambient |
| Mobile Phase A | 0.05% formic acid in water | 0.05% ammonia in water |
| Mobile Phase B | 0.05% formic acid in acetonitrile | 0.05% ammonia in acetonitrile |
| Gradient - Initial | 5% B | 5% B |
| Time 0 mins | 5% B | 5% B |
| Time 3 mins | 98% B | 98% B |
| Time 4 mins | 98% B | 98% B |
| Time 4.1 mins | 5% B | 5% B |
| Time 5 mins | 5% B | 5% B |
| Flow rate | 1.5 mL/min | 1.5 mL/min |
| Injection volume | 5 μL | 5 μL |

EXAMPLE 1

3-(4-Cyano-phenyl)-4-cyclopropyl-N-(2-hydroxy-2-methylpropyl)-1-isopropyl-1H-pyrazole-5-carboxamide

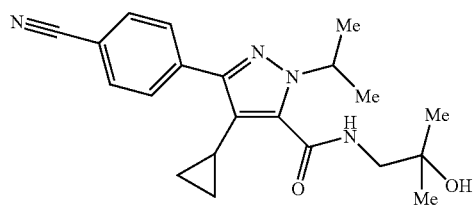

Thionyl Chloride (20 mL) was added to the compound described in Preparation 5 (2.50 g, 8.47 mmol). This mixture was refluxed for 16 hours. It was then evaporated under reduced pressure and azeotroped with toluene (3×50 mL) to give a gum. 2-methyltetrahydrofuran (20 mL) was added to the crude mixture, followed by triethylamine (2.36 mL, 17 mmol) and 1-amino-2-methyl-propan-2-ol (907 mg, 10.2 mmol). This mixture was then stirred at room temperature for 2 hours, after which time it was quenched onto a saturated aqueous solution of sodium hydrogen carbonate (20 mL), and extracted with ethyl acetate (2×20 mL). The combined organic layers were washed with a 10% w/v aqueous solution of citric acid (20 mL) and evaporated under reduced pressure to give a gum. This gum was triturated with diethyl ether to give the title compound as a white solid (2.32 g, 75%). $^1$H NMR (400 MHz, CDCl$_3$): δ 0.40 (m, 2H), 1.00 (m, 2H), 1.35 (s 6H), 1.55 (d, 6H), 1.80 (m, 1H), 3.50 (d, 2H), 5.40 (m, 1H), 7.00 (m, 1H), 7.65 (d, 2H), 7.80 (d, 1H). LCMS R$_t$=3.02 mins APCI MS m/z 367 [MH]$^+$.

EXAMPLE 1A 3-(4-Cyano-phenyl)-4-cyclopropyl-N-(2-hydroxy-2-methylpropyl)-1-isopropyl-1H-pyrazole-5-carboxamide

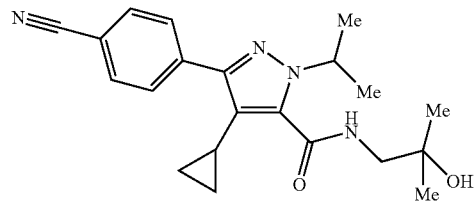

Thionyl Chloride (16.6 mL, 203 mmol) was added to the compound described in Preparation 72 (60 g, 203 mmol) in solution in isopropylacetate (600 mL). This mixture stirred at 70° C. for 3.5 hours and was then allowed to cool down to room temperature. Triethylamine (62.3 mL, 447 mmol) was then added slowly to this mixture followed by a solution of 1-amino-2-methyl-propan-2-ol (21.7 mg, 244 mmol) in iso-propylacetate (200 mL) over 20 minutes. The reaction mixture was stirred for 5 minutes at room temperature. It was then diluted with a saturated aqueous solution of sodium hydrogen carbonate (600 mL), water (500 mL) and was extracted with ethylacetate (1700 mL). The organic layer was washed with an aqueous solution of potassium hydroxide (1.0 M, 3×200 mL), dried with magnesium sulphate and evaporated under reduced to give a brown solid. This solid was recrystalised from acetonitrile:water (9:1, 660 mL) to afford a solid which was filtered off, rinsed with water (70 mL) and dried to give the title compound as white solid (42 g, 56%). (2.32 g, 75%). $^1$H NMR (400 MHz, CDCl$_3$): δ 0.40 (m, 2H), 1.00 (m, 2H), 1.35 (s 6H), 1.55 (d, 6H), 1.80 (m, 1H), 3.50 (d, 2H), 5.40 (m, 1H), 7.00 (m, 1H), 7.65 (d, 2H), 7.80 (d, 1H). LCMS R$_t$=3.02 mins APCI MS m/z 367 [MH]$^+$.

EXAMPLE 2

3-(4-Cyano-phenyl)-4-cyclopropyl-N-[(2S)-2-hydroxypropyl]-1-isopropyl-1H-pyrazole-5-carboxamide

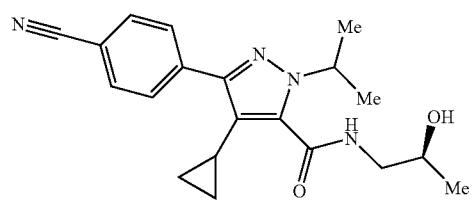

Using a procedure similar to that described for Example 1, but using (S)-(+)-1-amino-2-propanol, and purifying using column chromatography eluting with 50% ethyl acetate in pentane, the title compound was prepared as a solid (67 mg, 14%). $^1$H NMR (400 MHz, CDCl$_3$): δ 0.40 (m, 2H), 1.00 (m, 2H), 1.35 (d, 3H), 1.55 (d, 6H), 1.80 (m, 1H), 3.30 (m, 1H), 3.75 (m, 1H), 4.05 (m, 1H), 5.35 (m, 1H), 6.95 (m, 1H), 7.65 (d, 2H), 7.95 (d, 2H). ESCI MS m/z 353 [MH]$^+$.

EXAMPLE 3

3-(4-Cyano-phenyl)-4-cyclopropyl-N-[(2R)-2-hydroxypropyl]-1-isopropyl-1H-pyrazole-5-carboxamide

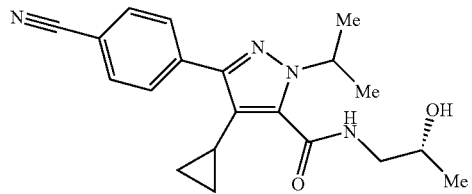

Using a procedure similar to that described for Example 1, but using (R)-(+)-1-amino-2-propanol, and purifying using column chromatography eluting with 50% ethyl acetate in pentane, the title compound was prepared as a solid (79 mg, 17%). $^1$H NMR (400 MHz, CDCl$_3$): δ 0.40 (m, 2H), 1.00 (m, 2H), 1.35 (d, 3H), 1.55 (d, 6H), 1.80 (m, 1H), 3.30 (m, 1H), 3.75 (m, 1H), 4.05 (m, 1H), 5.35 (m, 1H), 6.95 (m, 1H), 7.65 (d, 2H), 7.95 (d, 2H). APCI MS m/z 353 [MH]$^+$.

EXAMPLE 4

3-(4-Cyano-phenyl)-4-cyclopropyl-N,1-diisopropyl-1H-pyrazole-5-carboxamide

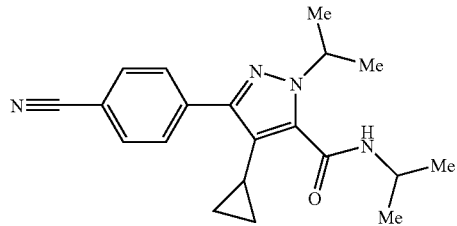

Using a procedure similar to that described for Example 1, but using isopropylamine, the title compound was prepared as a solid (186 mg, 41%). $^1$H NMR (400 MHz, CDCl$_3$): δ 0.40 (m, 2H), 1.00 (m, 2H), 1.30 (d, 6H), 1.50 (d, 6H), 1.80 (m, 1H), 4.30 (m, 1H), 5.30 (m, 1H), 6.25 (m, 1H), 7.65 (d, 2H), 7.95 (d, 2H). APCI MS m/z 337 [MH]$^+$.

EXAMPLE 5 tert-Butyl (3R)-3-({[3-(4-cyanophenyl)-4-cyclopropyl-1-isopropyl-1H-pyrazol-5-yl]carbonyl}amino)-pyrrolidine-1-carboxylate

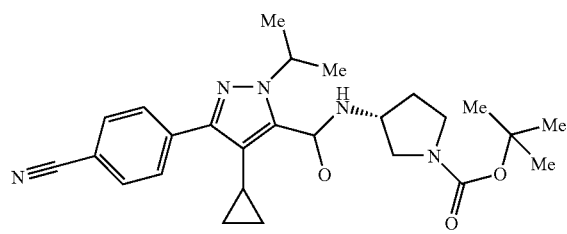

O-Benzotriazol-1-yl-N,N,N',N'-tetramethyluronium hexafluorophosphate (642 mg, 1.69 mmol) was added to a solution of the compound described in Preparation 5 (250 mg, 0.85 mmol) in 2-methyl tetrahydrofuran (5 mL), followed by pyridine (0.21 mL, 2.54 mmol) and (R)-(+)-N-Boc-3-aminopyrrolidine (0.19 mL, 1.10 mmol). This mixture was stirred at reflux for 1 hour and then allowed to stand at room temperature for 16 hours. The mixture was evaporated under reduced pressure to give a gum. This crude residue was partitioned between an aqueous saturated solution of sodium hydrogen carbonate (10 mL) and dichloromethane (5 mL). The organic layer was washed with an aqueous 10% w/v citric acid (10 mL), and evaporated under reduced pressure to give a solid (321 mg, 82%). $^1$H NMR (400 MHz, CDCl$_3$): δ 0.45 (m, 2H), 1.00 (m, 2H), 1.45 (s, 9H), 1.50 (d, 6H), 1.80 (m, 1H), 2.05-2.40 (m, 2H), 3.40-3.80 (m, 4H), 4.65 (m, 1H), 5.35 (m, 1H), 6.70 (d, 1H), 7.70 (d, 2H), 7.90 (m, 2H). APCI MS m/z 464 [MH]$^+$.

EXAMPLE 6

(tert-Butyl (3S)-3-({[3-(4-cyanophenyl)-4-cyclopropyl-1-isopropyl-1H-pyrazol-5-yl]carbonyl}amino)-pyrrolidine-1-carboxylate

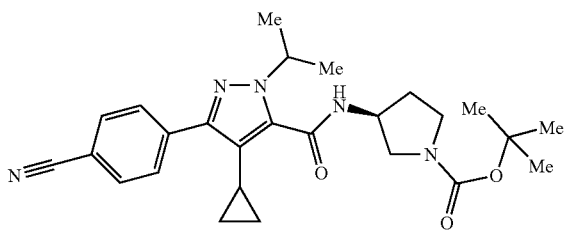

Using a procedure similar to that described for Example 5, but using (S)-(+)-N-Boc-3-aminopyrrolidine, the title compound was prepared as a solid (343 mg, 88%). $^1$H NMR (400 MHz, CDCl$_3$): δ 0.45 (m, 2H), 1.00 (m, 2H), 1.45 (s, 9H), 1.50 (d, 6H), 1.80 (m, 1H), 2.05-2.40 (m, 2H), 3.40-3.80 (m, 4H), 4.65 (m, 1H), 5.35 (m, 1H), 6.70 (d, 1H), 7.70 (d, 2H), 7.90 (m, 2H). APCI MS m/z 464 [MH]$^+$.

EXAMPLE 7 tert-Butyl 3-({[3-(4-cyanophenyl)-4-cyclopropyl-1-isopropyl-1H-pyrazol-5-yl]carbonyl}amino)azetidine-1-carboxylate

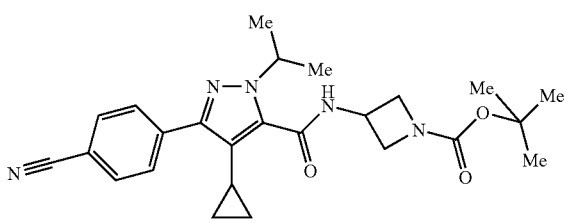

Using a procedure similar to that described for Example 5, but using 3-amino-1-N-boc-azetidine, the title compound was prepared as a solid (224 mg, 59%). $^1$H NMR (400 MHz, CDCl$_3$): δ 0.45 (m, 2H), 1.05 (m, 2H), 1.45 (s, 9H), 1.50 (d, 6H), 1.85 (m, 1H), 3.85 (m, 2H), 4.40 (m, 2H), 4.85 (m, 1H), 5.35 (m, 1H), 7.00 (d, 1H), 7.70 (d, 2H), 7.90 (m, 2H). APCI MS m/z 450 [MH]$^+$.

EXAMPLE 8

3-(4-Cyanophenyl)-4-cyclopropyl-1-isopropyl-N-[(3R)-pyrrolidin-3-yl]-1H-pyrazole-5-carboxamide hydrochloride

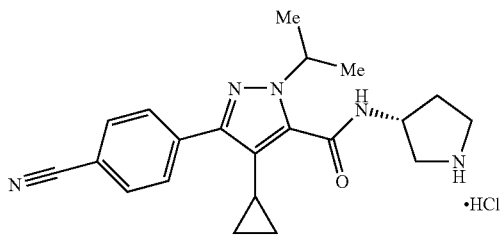

Using a procedure similar to that described for Preparation 19, but using the compound described in Example 5, the title compound was prepared as a solid (205 mg, 77%). $^1$H NMR (400 MHz, CD$_3$OD): δ 0.30 (m, 2H), 0.95 (m, 2H), 1.45 (d, 6H), 1.95 (m, 1H), 2.20 (m, 1H), 2.45 (m, 1H), 3.30 (m, 1H), 3.35 (m, 1H), 3.55 (m, 1H), 3.70 (m, 1H), 4.60 (m, 1H), 4.85 (m, 1H), 7.80 (d, 2H), 8.05 (d, 2H). APCI MS m/z 364 [MH]$^+$.

EXAMPLE 9

3-(4-Cyanophenyl)-4-cyclopropyl-1-isopropyl-N-[(3S)-pyrrolidin-3-yl]-1H-pyrazole-5-carboxamide hydrochloride

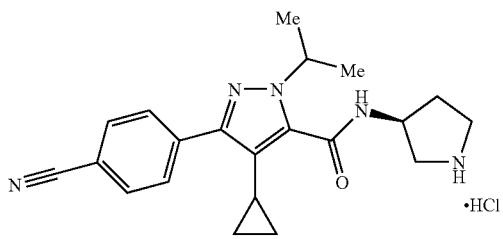

Using a procedure similar to that described for Preparation 19, but using the compound described in Example 6, the title compound was prepared as a solid (156 mg, 58%). $^1$H NMR (400 MHz, CD$_3$OD): δ 0.30 (m, 2H), 0.95 (m, 2H), 1.45 (d, 6H), 1.95 (m, 1H), 2.20 (m, 1H), 2.45 (m, 1H), 3.30 (m, 1H), 3.35 (m, 1H), 3.55 (m, 1H), 3.70 (m, 1H), 4.60 (m, 1H), 4.85 (m, 1H), 7.80 (d, 2H), 8.05 (d, 2H). APCI MS m/z 364 [MH]$^+$.

EXAMPLE 10

N-Azetidin-3-yl-3-(4-cyanophenyl)-4-cyclopropyl-1-isopropyl-1H-pyrazole-5-carboxamide

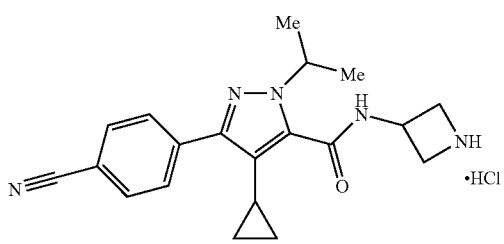

Using a procedure similar to that described for Preparation 19, but using the compound described in Example 7, the title compound was prepared as a solid (134 mg, 52%). $^1$H NMR (400 MHz, CD$_3$OD): δ 0.30 (m, 2H), 0.95 (m, 2H), 1.45 (d, 6H), 2.00 (m, 1H), 3.30 m, 1H), 4.40 (m, 4H), 4.90 (m, 1H), 7.80 (d, 2H), 8.05 (d, 2H). APCI MS m/z 350 [MH]$^+$.

EXAMPLE 11

3-(4-Cyanophenyl)-4-cyclopropyl-N-[(3R)-1-isobutyrylpyrrolidin-3-yl]-1-isopropyl-1H-pyrazole-5-carboxamide

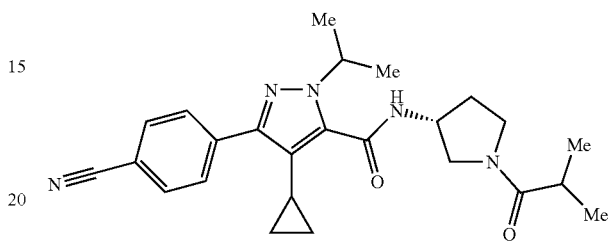

Isobutyryl chloride (18 μL, 0.17 mmol) was added to a solution of the compound described in Example 8 (46 mg, 0.12 mmol) and triethylamine (48 μL, 0.35 mmol) in dichloromethane (2 mL). This mixture was stirred at room temperature for 2 hours, After which time it was washed with an aqueous saturated solution of sodium hydrogen carbonate (5 mL) and a 10% w/v aqueous solution of citric acid (5 mL), then evaporated under reduced pressure to give a solid (40 mg, 80%). LCMS R$_t$=1.49 mins ESCI MS m/z 434 [MH]$^+$.

EXAMPLE 12

3-(4-Cyanophenyl)-4-cyclopropyl-1-isopropyl-N-[(3S)-1-propionylpyrrolidin-3-yl]-1H-pyrazole-5-carboxamide

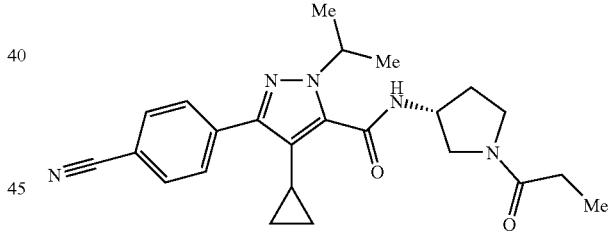

Using a procedure similar to that described for Example 11, but using propionyl chloride, the title compound was prepared as a solid (26 mg, 54%). LCMS R$_t$=1.43 mins ESCI MS m/z 420 [MH]$^+$.

EXAMPLE 13

3-(4-Cyanophenyl)-4-cyclopropyl-1-isopropyl-N-[(3R)-1-(methylsulfonyl)pyrrolin-3-yl]-1H-pyrazole-5-carboxamide

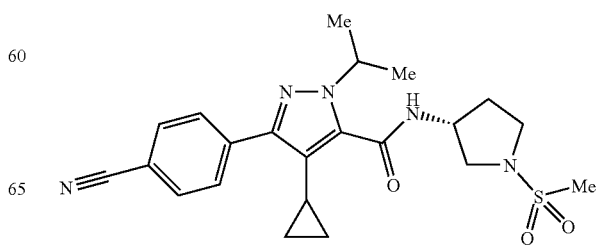

Using a procedure similar to that described for Example 11, but using methane sulphonyl chloride, the title compound was prepared as a solid (34 mg, 67%). LCMS R$_t$=1.49 mins ESCI MS m/z 442 [MH]$^+$.

EXAMPLE 14

3-(4-Cyanophenyl)-4-cyclopropyl-N-[(3S)-1-isobutyrylpyrrolidin-3-yl]-1-isopropyl-1H-pyrazole-5-carboxamide

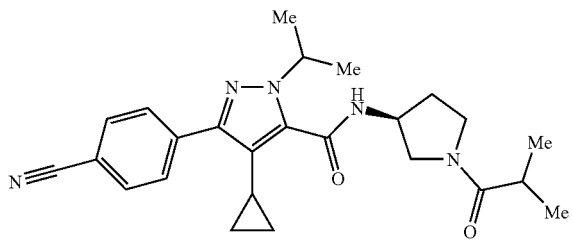

Using a procedure similar to that described for Example 11, but using the compound described in Example 9, the title compound was prepared as a solid (32 mg, 84%). LCMS R$_t$=1.49 mins ESCI MS m/z 434 [MH]$^+$.

EXAMPLE 15

3-(4-Cyanophenyl)-4-cyclopropyl-1-isopropyl-N-[(3S)-1-propionylpyrrolidin-3-yl]-1H-pyrazole-5-carboxamide

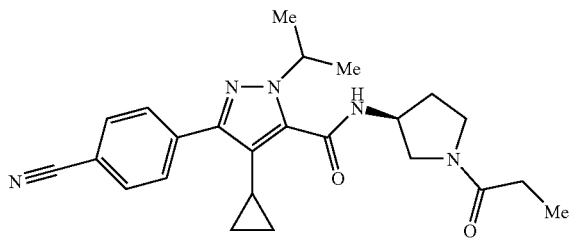

Using a procedure similar to that described for Example 11 but using the compound described in Example 9 and propionyl chloride, the title compound was prepared as a solid (24 mg, 65%). LCMS R$_t$=1.43 mins ESCI MS m/z 420 [MH]$^+$.

EXAMPLE 16

3-(4-Cyanophenyl)-4-cyclopropyl-N-(1-isobutyrylazetidin-3-yl)-1-isopropyl-1H-pyrazole-5-carboxamide

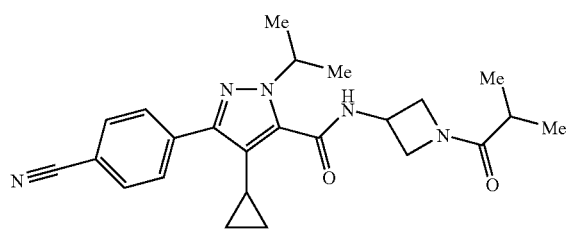

Using a procedure similar to that described for Example 11, but using the compound described in Example 10, the title compound was prepared as a solid (21 mg, 64%). LCMS R$_t$=1.49 mins ESCI MS m/z 420 [MH]$^+$.

EXAMPLE 17

3-(4-Cyanophenyl)-4-cyclopropyl-1-isopropyl-N-(1-propionyl azetidin-3-yl)-1H-pyrazole-5-carboxamide

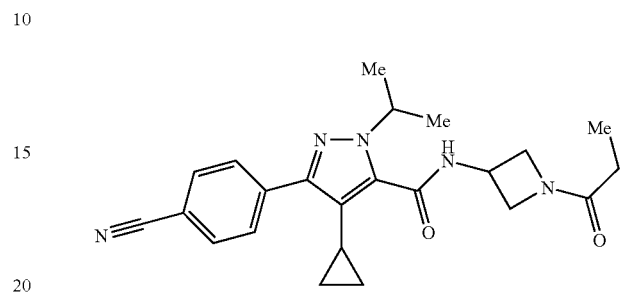

Using a procedure similar to that described for Example 11 but using the compound described in Example 10 and propionyl chloride, the title compound was prepared as a solid (24 mg, 76%). LCMS R$_t$=1.42 mins ESCI MS m/z 406 [MH]$^+$.

EXAMPLE 18

3-(4-Cyanophenyl)-4-cyclopropyl-1-isopropyl-N-[1-(methyl sulfonyl) azetidin-3-yl]-1H-pyrazole-5-carboxamide

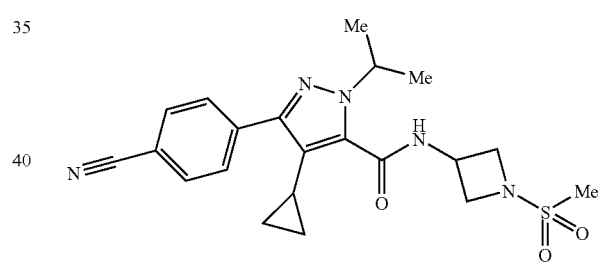

Using a procedure similar to that described for Example 11 but using the compound described in Example 10 and methane sulphonyl chloride, the title compound was prepared as a solid (15 mg, 45%). LCMS R$_t$=1.50 mins ESCI MS m/z 428 [MH]$^+$.

EXAMPLE 19

N-(1-Acetylazetidin-3-yl)-3-(4-cyanophenyl)-4-cyclopropyl-1-isopropyl-1H-pyrazole-5-carboxamide

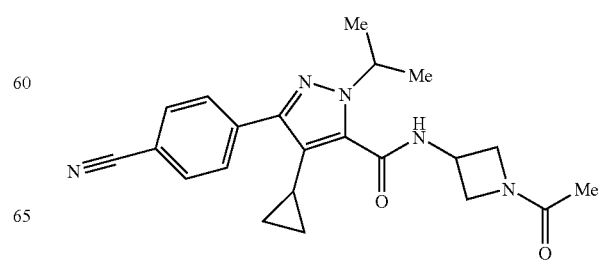

Using a procedure similar to that described for Example 11 but using the compound described in Example 10 and acetyl chloride, the title compound was prepared as a solid (28 mg, 92%). LCMS $R_t$=1.35 mins ESCI MS m/z 392 [MH]$^+$.

EXAMPLE 20

3-(4-Cyanophenyl)-4-cyclopropyl-1-isopropyl-N-propyl-1H-pyrazole-5-carboxamide

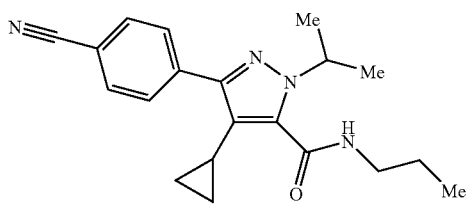

Prepared using a procedure similar to that described for Example 1, but using N-propylamine, the title compound was purified by high performance liquid chromatography. LCMS $R_t$=3.65 mins ESCI MS m/z 337 [MH]$^+$.

EXAMPLE 21

3-(4-Cyanophenyl)-4-cyclopropyl-1-isopropyl-N-(3-methoxy propyl)-1H-pyrazole-5-carboxamide

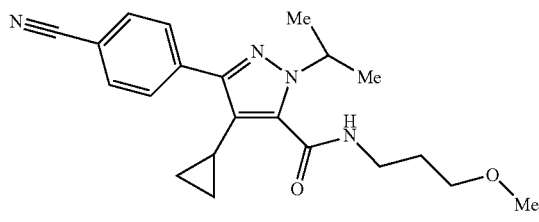

Prepared using a procedure similar to that described for Example 1, but using 3-methoxypropylamine, the title compound was purified by high performance liquid chromatography. LCMS $R_t$=2.50 mins ESCI MS m/z 367 [MH]$^+$.

EXAMPLE 22

3-(4-Cyanophenyl)-4-cyclopropyl-1-isopropyl-N-(3,3,3-trifluoro propyl)-1H-pyrazole-5-carboxamide

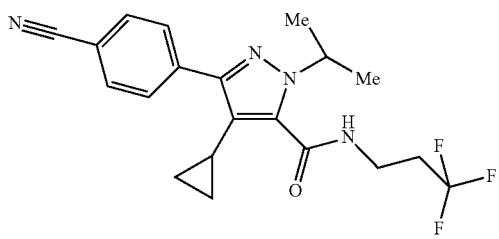

Prepared using a procedure similar to that described for Example 1, but using 3,3,3-trifluoropropyl amine hydrochloride, the title compound was purified by high performance liquid chromatography. LCMS $R_t$=3.88 mins ESCI MS m/z 391 [MH]$^+$.

EXAMPLE 23

3-(4-Cyanophenyl)-4-cyclopropyl-1-isopropyl-N-(pyrimidin-4-yl methyl)-1H-pyrazole-5-carboxamide

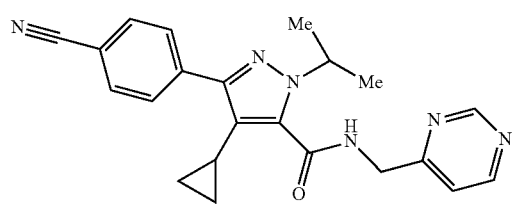

Prepared using a procedure similar to that described for Example 1, but using 4-(aminomethyl)-pyrimidine hydrochloride, the title compound was purified by high performance liquid chromatography. LCMS $R_t$=3.29 mins ESCI MS m/z 387 [MH]$^+$.

EXAMPLE 24

3-(4-Cyanophenyl)-4-cyclopropyl-1-isopropyl-N-[(3S)-2-oxo tetrahydrofuran-3-yl]-1H-pyrazole-5-carboxamide

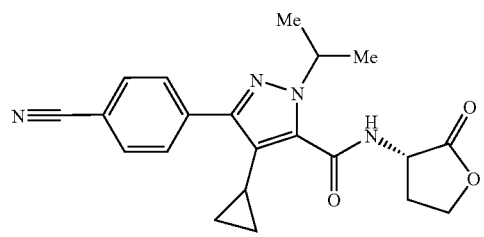

Prepared using a procedure similar to that described for Example 1, but using (S)-(−)-α-amino-γ-butyrloactone hydrobromide, the title compound was purified by high performance liquid chromatography. LCMS $R_t$=3.23 mins ESCI MS m/z 379 [MH]$^+$.

EXAMPLE 25

3-(4-Cyanophenyl)-4-cyclopropyl-1-isopropyl-N-[2-(methyl amino)-2-oxoethyl]-1H-pyrazole-5-carboxamide

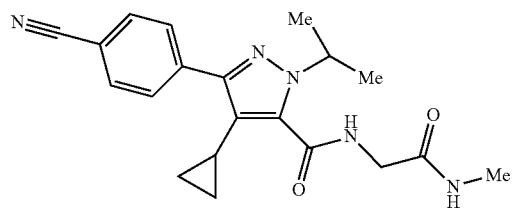

Prepared using a procedure similar to that described for Example 1, but using H-Gly-NHMe hydrochloride, the title compound was purified by high performance liquid chromatography. LCMS $R_t$=3.07 mins ESCI MS m/z 366 [MH]$^+$.

EXAMPLE 26

3-(4-Cyanophenyl)-4-cyclopropyl-1-isopropyl-N-[3-(2-oxopyrrolidin-1-yl)propyl]-1H-pyrazole-5-carboxamide

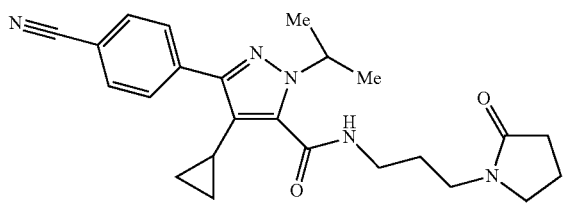

Prepared using a procedure similar to that described for Example 1, but using N-(3-aminopropyl)-2-pyrrolidinone, the title compound was purified by high performance liquid chromatography. LCMS $R_t$=3.20 mins ESCI MS m/z 420 [MH]$^+$.

EXAMPLE 27

Methyl N-{[3-(4-cyanophenyl)-4-cyclopropyl-1-isopropyl-1H-pyrazol-5-ylcarbonyl}-2-methyl-alaninate

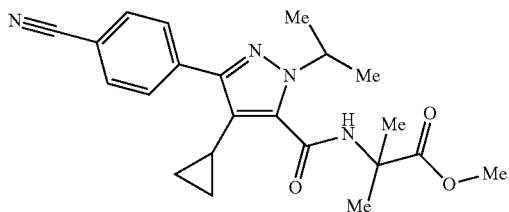

Prepared using a procedure similar to that described for Example 1, but using α-aminoisobutyric acid methyl ester hydrochloride, the title compound was purified by high performance liquid chromatography. LCMS $R_t$=3.66 mins ESCI MS m/z 395 [MH]$^+$.

EXAMPLE 28

N-(2-Aminoethyl)-3-(4-cyanophenyl)-4-cyclopropyl-1-isopropyl-1H-pyrazole-5-carboxamide

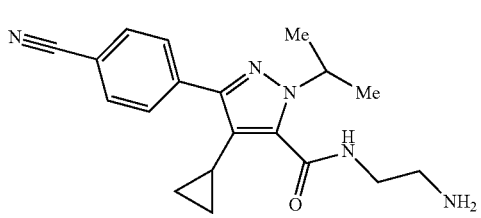

Prepared using a procedure similar to that described for Example 1, but using ethylenediamine, the title compound was purified by high performance liquid chromatography. LCMS $R_t$=2.30 mins ESCI MS m/z 338 [MH]$^+$.

EXAMPLE 29

N-(2-amino-2-methylpropyl)-3-(4-cyanophenyl)-4-cyclopropyl-1-isopropyl-1H-pyrazole-5-carboxamide

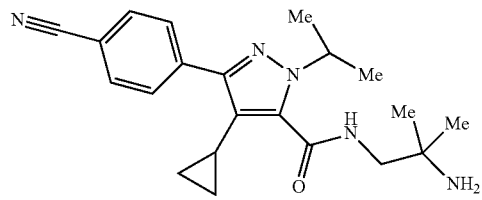

Prepared using a procedure similar to that described for Example 1, but using 1,2-diamino-2-methylpropane, the title compound was purified by high performance liquid chromatography. LCMS $R_t$=2.33 mins ESCI MS m/z 366 [MH]$^+$.

EXAMPLE 30

3-(4-Cyanophenyl)-4-cyclopropyl-1-isopropyl-N-[(1-methyl-1H-pyrazol-4-yl)methyl]-1H-pyrazole-5-carboxamide

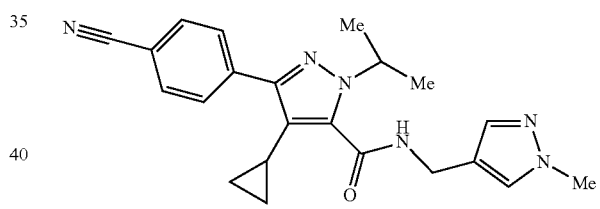

Prepared using a procedure similar to that described for Example 1, but using C-(1-Methyl-1H-pyrazol-4-yl)-methylamine, the title compound was purified by high performance liquid chromatography. LCMS $R_t$=1.43 mins ESCI MS m/z 389 [MH]$^+$.

EXAMPLE 31

3-(4-Cyanophenyl)-4-cyclopropyl-N-[(1R,3S)-3-hydroxy cyclopentyl]-1-isopropyl-1H-pyrazole-5-carboxamide

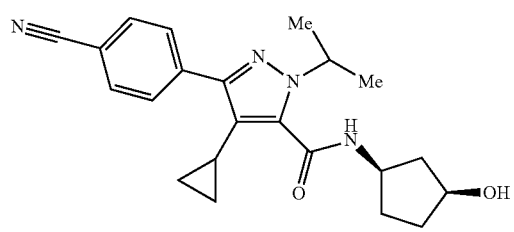

Prepared using a procedure similar to that described for Example 1, but using (1S,3R)-3-Amino-cyclopentanol, the title compound was purified by high performance liquid chromatography. LCMS R$_t$=1.43 mins ESCI MS m/z 379 [MH]$^+$.

EXAMPLE 32

3-(4-Cyanophenyl)-4-cyclopropyl-N-(cis-3-hydroxy-cyclobutyl)-1-isopropyl-1H-pyrazole-5-carboxamide

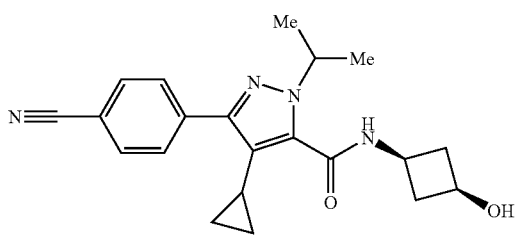

Prepared using a procedure similar to that described for Example 1, but using the compound described in Preparation 65, the title compound was purified by high performance liquid chromatography. LCMS R$_t$=1.37 mins ESCI MS m/z 365 [MH]$^+$.

EXAMPLE 33

3-(4-Cyanophenyl)-4-cyclopropyl-1-isopropyl-N-[(1S)-1-methyl propyl]-1H-pyrazole-5-carboxamide

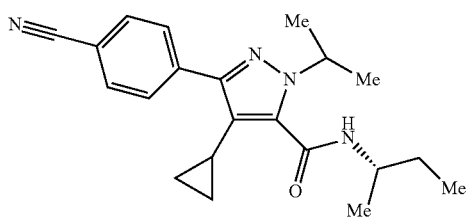

Prepared using a procedure similar to that described for Example 1, but using (+)-2-aminobutane, the title compound was purified by high performance liquid chromatography. LCMS R$_t$=2.38 mins ESCI MS m/z 351 [MH]$^+$.

EXAMPLE 34

3-(4-Cyanophenyl)-4-cyclopropyl-N-(2,2-dimethyl-propyl)-1-isopropyl-1H-pyrazole-5-carboxamide

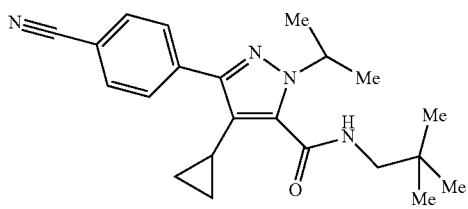

Prepared using a procedure similar to that described for Example 1, but using neopentylamine, the title compound was purified by high performance liquid chromatography. LCMS R$_t$=3.54 mins ESCI MS m/z 365 [MH]$^+$.

EXAMPLE 35

3-(4-Cyanophenyl)-4-cyclopropyl-1-isopropyl-N-[(1R)-1-methyl propyl]-1H-pyrazole-5-carboxamide

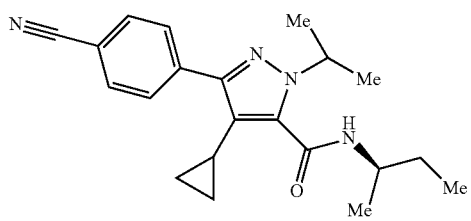

Prepared using a procedure similar to that described for Example 1, but using (R)-(−)-2-aminobutane, the title compound was purified by high performance liquid chromatography. LCMS R$_t$=2.38 mins ESCI MS m/z 351 [MH]$^+$.

EXAMPLE 36

(+/−)-3-(4-Cyanophenyl)-4-cyclopropyl-1-isopropyl-N-(tetrahydrofuran-2-ylmethyl)-1H-pyrazole-5-carboxamide

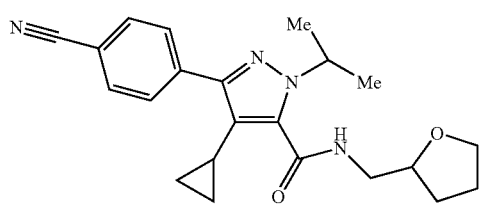

Prepared using a procedure similar to that described for Example 1, but using (+/−)-tetrahydrofurfurylamine, the title compound was purified by high performance liquid chromatography. LCMS R$_t$=3.18 mins ESCI MS m/z 379 [MH]$^+$.

EXAMPLE 37

3-(4-Cyanophenyl)-4-cyclopropyl-N-[(6S)-6,7-dihydro-5H-pyrrolo[1,2-a]imidazol-6-yl]-1-isopropyl-1H-pyrazole-5-carboxamide

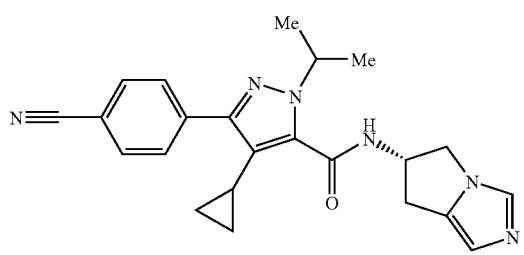

Prepared using a procedure similar to that described for Example 1, but using the compound described in Preparation 68, the title compound was purified by high performance liquid chromatography. LCMS $R_t$=2.29 mins ESCI MS m/z 401 [MH]+.

EXAMPLE 38

3-(4-Cyanophenyl)-4-cyclopropyl-N-[(6R)-6,7-dihydro-5H-pyrrolo[1,2-a]imidazol-6-yl]-1-isopropyl-1H-pyrazole-5-carboxamide

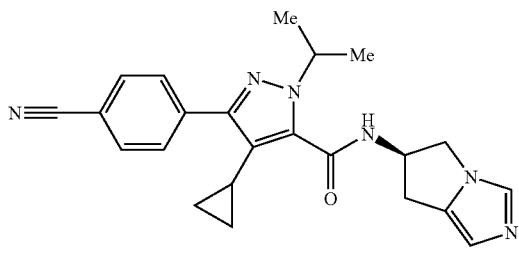

Prepared using a procedure similar to that described for Example 1, but using the compound described in Preparation 67, the title compound was purified by high performance liquid chromatography. LCMS $R_t$=2.30 mins ESCI MS m/z 401 [MH]+.

EXAMPLE 39

(+/−)-3-(4-Cyanophenyl)-4-cyclopropyl-1-isopropyl-N-[1-(1-methyl-1H-pyrazol-4-yl)ethyl-1H-pyrazole-5-carboxamide

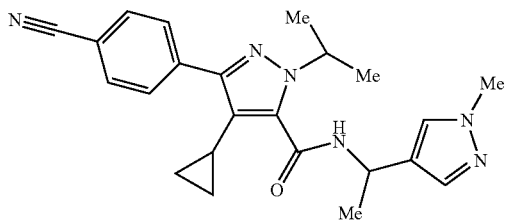

Prepared using a procedure similar to that described for Example 1, but using (+/−)-1-(1-methyl-1H-pyrazol-4-yl)-ethylamine, the title compound was purified by high performance liquid chromatography. LCMS $R_t$=3.01 mins ESCI MS m/z 403 [MH]+.

EXAMPLE 40

(+/−)-3-(4-Cyanophenyl)-4-cyclopropyl-1-isopropyl-N-(tetrahydro-2H-pyran-3-yl)-1H-pyrazole-5-carboxamide

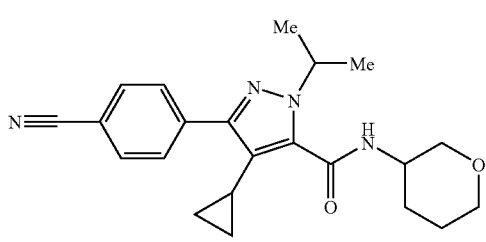

Prepared using a procedure similar to that described for Example 1, but using (+/−)-tetrahydro-pyran-3-ylamine, the title compound was purified by high performance liquid chromatography. LCMS $R_t$=3.10 mins ESCI MS m/z 379 [MH]+.

EXAMPLE 41

(+/−)-3-(4-Cyanophenyl)-4-cyclopropyl-1-isopropyl-N-(1-methyl-6-oxopiperidin-3-yl)-1H-pyrazole-5-carboxamide

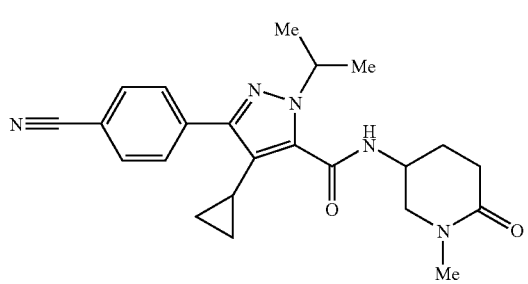

Prepared using a procedure similar to that described for Example 1, but using 5-amino-1-methyl-piperidin-2-one (prepared according to J. Antibiot. Ser. A. 17, 1964, 172) the title compound was purified by high performance liquid chromatography. LCMS $R_t$=2.80 mins ESCI MS m/z 406 [MH]+.

EXAMPLE 42

3-(4-Cyanophenyl)-4-cyclopropyl-N-[2-(ethylamino)-2-oxoethyl]-1-isopropyl-1H-pyrazole-5-carboxamide

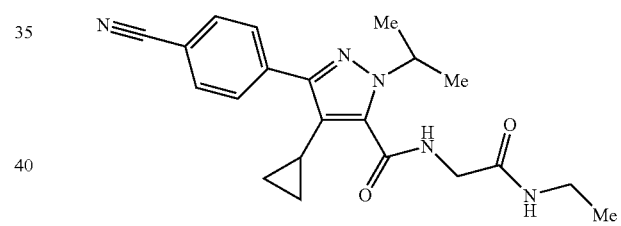

Prepared using a procedure similar to that described for Example 1, but using 2-amino-N-ethyl-acetamide, the title compound was purified by high performance liquid chromatography. LCMS $R_t$=2.89 mins ESCI MS m/z 380 [MH]+.

EXAMPLE 43

3-(4-Cyanophenyl)-4-cyclopropyl-1-isopropyl-N-(tetrahydro-2H-pyran-4-yl-1H-pyrazole-5-carboxamide

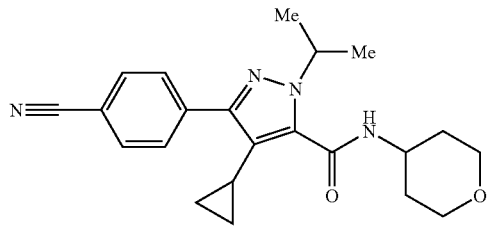

Prepared using a procedure similar to that described for Example 1, but using tetrahydro-pyran-4-ylamine, the title compound was purified by high performance liquid chromatography. LCMS $R_t$=3.00 mins ESCI MS m/z 379 [MH]+.

EXAMPLE 44

(+/−)-3-(4-Cyanophenyl)-4-cyclopropyl-1-isopropyl-N-[1-methyl-2-(1H-pyrazol-1-yl)ethyl]-1H-pyrazole-5-carboxamide

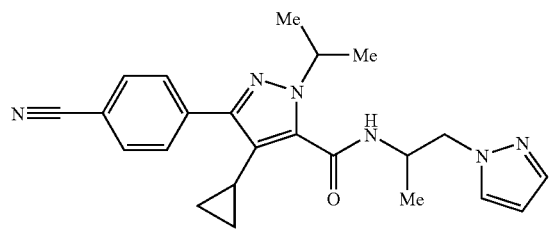

Prepared using a procedure similar to that described for Example 1, but using (+/−)-1-methyl-2-pyrazol-1-yl-ethylamine, the title compound was purified by high performance liquid chromatography. LCMS $R_t$=3.09 mins ESCI MS m/z 403 [MH]$^+$.

EXAMPLE 45

(+/−)-3-(4-Cyanophenyl)-4-cyclopropyl-1-isopropyl-N-[(3R)-5-oxopyrrolidin-3-yl]-1H-pyrazole-5-carboxamide

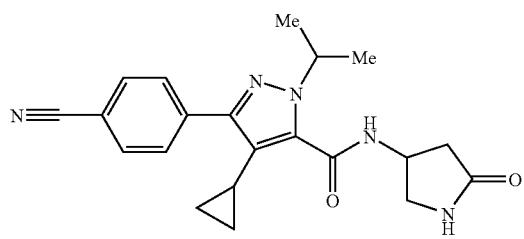

Prepared using a procedure similar to that described for Example 1, but using (+/−)-4-amino-pyrrolidin-2-one, the title compound was purified by high performance liquid chromatography. LCMS $R_t$=2.67 mins ESCI MS m/z 378 [MH]$^+$.

EXAMPLE 46

3-(4-Cyanophenyl)-4-cyclopropyl-1-isopropyl-N-methyl-1H-pyrazole-5-carboxamide

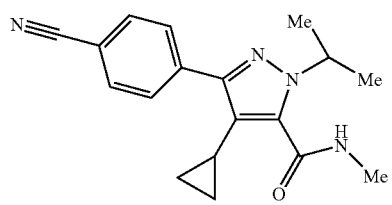

Prepared using a procedure similar to that described for Example 1, but using methylamine hydrochloride, the title compound was prepared as a white solid (44 mg, 85%). $^1$H NMR (400 MHz, CDCl$_3$): δ 0.40 (m, 2H), 0.95 (m, 2H), 1.50 (d, 6H), 1.75 (m, 1H), 3.05 (d, 3H), 5.30 (m, 1H), 6.45 (m, 1H), 7.65 (d, 2H), 7.95 (d, 2H). LCMS $R_t$=2.91 mins ESCI MS m/z 309 [MH]$^+$.

EXAMPLE 47

3-(4-Cyanophenyl)-4-cyclopropyl-N-ethyl-1-isopropyl-1H-pyrazole-5-carboxamide

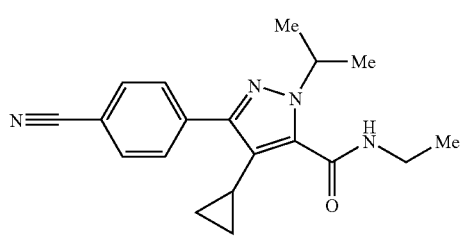

Prepared using a procedure similar to that described for Example 1, but using ethylamine hydrochloride, the title compound was isolated as a white solid (14 mg, 26%). LCMS $R_t$=3.04 mins ESCI MS m/z 323 [MH]$^+$.

EXAMPLE 48

3-(4-Cyanophenyl)-4-cyclopropyl-1-isopropyl-N-(2,2,2-trifluoro ethyl)-1H-pyrazole-5-carboxamide

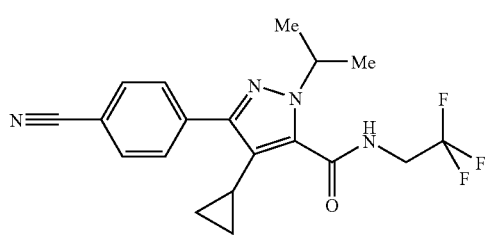

Prepared using a procedure similar to that described for Example 1, but using 2,2,2-trifluoroethylamine, the title compound was purified by high performance liquid chromatography. LCMS $R_t$=3.31 mins ESCI MS m/z 377 [MH]$^+$.

EXAMPLE 49

3-(4-Cyanophenyl)-4-cyclopropyl-N-(cyclopropylmethyl)-1-isopropyl-1H-pyrazole-5-carboxamide

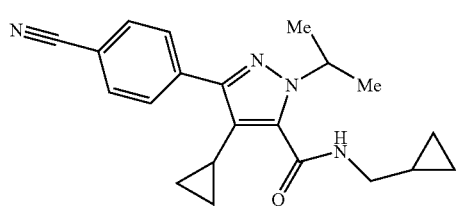

Prepared using a procedure similar to that described for Example 1, but using cyclopropylmethylamine, the title compound was purified by high performance liquid chromatography. LCMS $R_t$=3.30 mins ESCI MS m/z 349 [MH]$^+$.

EXAMPLE 50

3-(4-Cyanophenyl)-N-cyclobutyl-4-cyclopropyl-1-isopropyl-1H-pyrazole-5-carboxamide

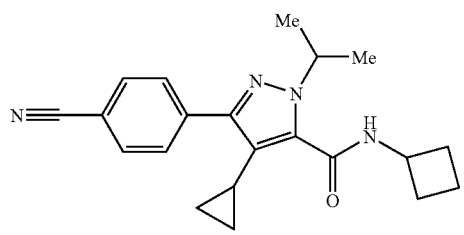

Prepared using a procedure similar to that described for Example 1, but using cyclobutylamine, the title compound was purified by high performance liquid chromatography. LCMS $R_t$=3.27 mins ESCI MS m/z 349 [MH]$^+$.

EXAMPLE 51

3-(4-Cyanophenyl)-4-cyclopropyl-N-(cyclopropylmethyl)-1-isopropyl-N-methyl-1H-pyrazole-5-carboxamide

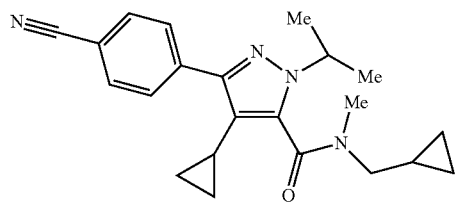

Prepared using a procedure similar to that described for Example 1, but using cyclopropylmethyl-methyl-amine (prepared according to J. Heterocyclic Chem., 20, 1031 (1983)), the title compound was purified by high performance liquid chromatography. LCMS $R_t$=3.38 mins ESCI MS m/z 363 [MH]$^+$.

EXAMPLE 52

3-(4-Cyanophenyl)-4-cyclopropyl-1-isopropyl-N-(tetrahydrofuran-3-yl)-1H-pyrazole-5-carboxamide

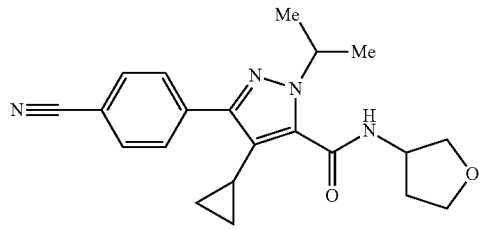

Prepared using a procedure similar to that described for Example 1, but using (+/−)-tetrahydrofuran-3-ylamine hydrochloride, the title compound was purified by high performance liquid chromatography. LCMS $R_t$=2.93 mins ESCI MS m/z 365 [MH]$^+$.

EXAMPLE 53

3-(4-Cyanophenyl)-4-cyclopropyl-1-isopropyl-N-[(2R)-tetrahydrofuran-2-ylmethyl]-1H-pyrazole-5-carboxamide

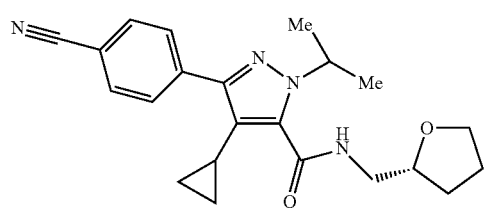

Prepared using a procedure similar to that described for Example 1, but using (R)-(−)-tetrahydrofurfurylamine, the title compound was purified by high performance liquid chromatography. LCMS $R_t$=3.12 mins ESCI MS m/z 379 [MH]$^+$.

EXAMPLE 54

3-(4-Cyanophenyl)-4-cyclopropyl-N-(2-cyclopropylethyl)-1-isopropyl-1H-pyrazole-5-carboxamide

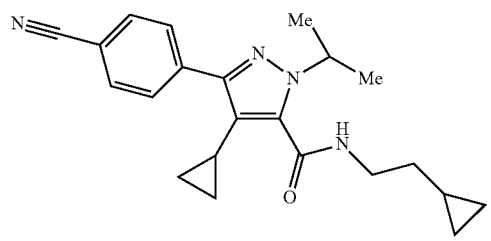

Prepared using a procedure similar to that described for Example 1, but using 2-cyclopropyl-ethylamine hydrochloride (prepared according to Bioorganic & Medicinal Chemistry Letters 14 (2004) 3147-3149), the title compound was purified by high performance liquid chromatography. LCMS $R_t$=3.36 mins ESCI MS m/z 363 [MH]$^+$.

EXAMPLE 55

3-(4-Cyanophenyl)-4-cyclopropyl-1-isopropyl-N-[(2S)-tetrahydrofuran-2-yl methyl]-1H-pyrazole-5-carboxamide

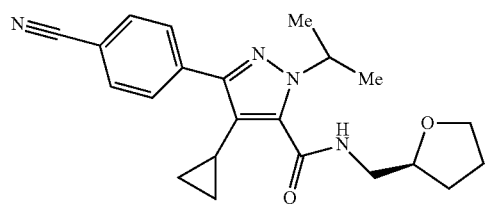

Prepared using a procedure similar to that described for Example 1, but using (S)-(−)-tetrahydrofurfurylamine, the title compound was purified by high performance liquid chromatography. LCMS $R_t$=3.12 mins ESCI MS m/z 379 [MH]$^+$.

EXAMPLE 56

3-(4-Cyanophenyl)-4-cyclopropyl-N-(2-hydroxy-1,1-dimethylethyl)-1-isopropyl-1H-pyrazole-5-carboxamide

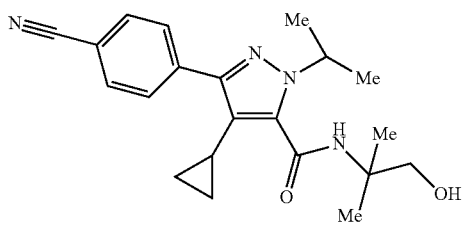

Prepared using a procedure similar to that described for Example 1, but using 2-amino-2-methyl-1-propanol, the title compound was purified by high performance liquid chromatography. LCMS $R_t$=3.02 mins ESCI MS m/z 367 [MH]$^+$.

EXAMPLE 57

(+/−)-3-(4-Cyanophenyl)-4-cyclopropyl-N-(1,1-dioxidotetrahydro-3-thienyl)-1-isopropyl-1H-pyrazole-5-carboxamide

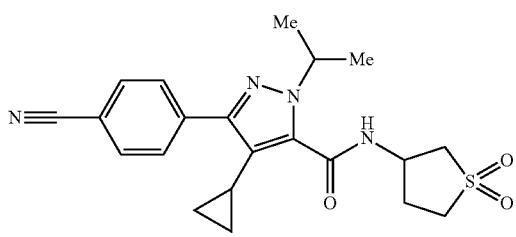

Prepared using a procedure similar to that described for Example 1, but using tetrahydro-3-thiophenamine 1,1-dioxide, the title compound was purified by high performance liquid chromatography. LCMS $R_t$=2.90 mins ESCI MS m/z 413 [MH]$^+$.

EXAMPLE 58

3-(4-Cyanophenyl)-N,4-dicyclopropyl-1-isopropyl-1H-pyrazole-5-carboxamide

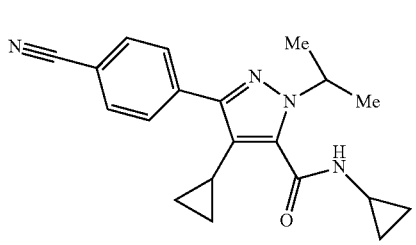

Diisopropylethylamine (13.80 mL, 39.5 mmol) and cyclopropylamine (2.77 mL, 39.5 mmol) were added to a solution of the compound described in Preparation 5 (2.92 g, 9.89 mmol) in 2-methyltetrahydrofuran (115 mL). This mixture was heated to 70° C. and 1-propanephosphonic acid cyclic anhydride (50% weight solution in dichloroethane) (17.30 mL, 59.3 mmol) was added. The mixture was heated at 70° C. for 16 hours, and then diluted with ethyl acetate (200 mL). It was washed with saturated sodium carbonate (100 mL), 10% w/v aqueous solution of citric acid (100 mL) and sodium carbonate (100 mL). The combined organic extracts were dried over magnesium sulphate, filtered, and evaporated under reduced pressure to give an oil. The crude residue was purified by column chromatography, eluting with 50% ethyl acetate in heptane, to give a solid. This solid was recrystallized with 2-propanol to give the title compound as a white solid (2.46 g, 74%). $^1$H NMR (400 MHz, CDCl$_3$): δ 0.40 (m, 2H), 0.65 (m, 2H), 0.95 (m, 4H), 1.50 (d, 6H), 1.75 (m, 1H), 2.95 (m, 1H), 5.35 (m, 1H), 6.60 (m, 1H), 7.65 (d, 2H), 7.90 (d, 2H). ESCI MS m/z 335 [MH]$^+$.

EXAMPLE 59

3-(4-Cyanophenyl)-4-cyclopropyl-1-isopropyl-N-(2-methoxy ethyl)-1H-pyrazole-5-carboxamide

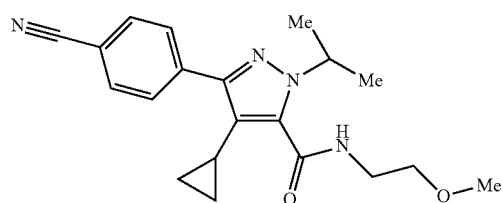

Prepared using a procedure similar to that described for Example 1, but using 2-methoxyethylamine, the title compound was purified by high performance liquid chromatography. LCMS $R_t$=3.05 mins ESCI MS m/z 353 [MH]$^+$.

EXAMPLE 60

N-tert-Butyl-3-(4-cyanophenyl)-4-cyclopropyl-1-isopropyl-1H-pyrazole-5-carboxamide

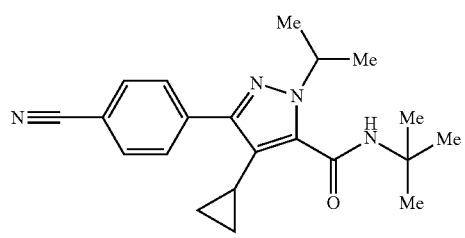

Prepared using a procedure similar to that described for Example 1, but using tert-butylamine, the title compound was purified by high performance liquid chromatography. LCMS $R_t$=3.40 mins ESCI MS m/z 351 [MH]⁺.

EXAMPLE 61

3-(4-Cyanophenyl)-4-cyclopropyl-1-isopropyl-N-(2-oxopropyl)-1H-pyrazole-5-carboxamide

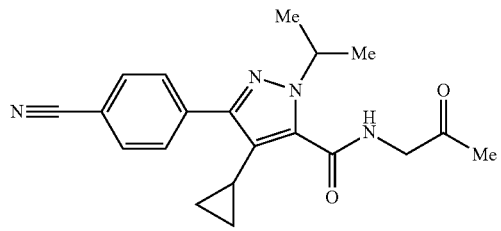

Triethylamine (0.16 mL, 1.22 mmol) was added to a solution of either the compound described in Example 2, or Example 3, or a mixture thereof (215 mg, 0.61 mmol), in dimethyl sulphoxide (10 mL) followed by a solution of sulphur trioxide pyridine complex (0.19 g, 1.22 mmol) in dimethyl sulphoxide (5 mL). This mixture was stirred at room temperature for 16 hours and then partitioned between water (50 mL) and ethyl acetate (50 mL, 20 mL). The combined organic extracts were washed with brine (30 mL) dried over magnesium sulphate, filtered, and evaporated under reduced pressure to give an oil. This crude residue was purified by column chromatography eluting with 50% ethyl acetate in heptane to give a solid (0.085 g, 40%). ¹H NMR (400 MHz, CDCl₃): δ 0.00 (m, 2H), 0.65 (m, 2H), 1.15 (d, 6H), 1.55 (m, 1H), 1.90 (s, 3H), 4.05 (d, 2H), 5.00 (m, 1H), 7.05 (m, 1H), 7.30 (d, 1H), 7.55 (d, 1H). ESCI MS m/z 351 [MH]⁺.

EXAMPLE 62

3-(4-Cyano-3-methylphenyl)-N-(cyclopropylmethyl)-1-isopropyl-4-methyl-1H-pyrazole-5-carboxamide

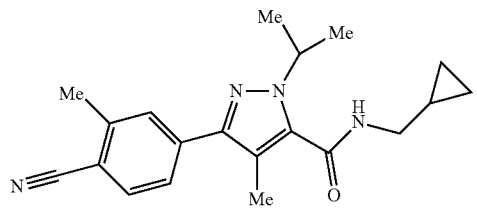

Using a procedure similar to that described for Example 1, but using the compound described in Preparation 11 and cyclopropylmethylamine, the title compound was prepared as a solid (0.21 g, 64%). LCMS $R_t$=2.49 mins ESCI MS m/z 335 [MH]⁻.

EXAMPLE 63

3-(4-Cyano-3-methylphenyl)-N-[(2S)-2-hydroxypropyl]-1-isopropyl-4-methyl-1H-pyrazole-5-carboxamide

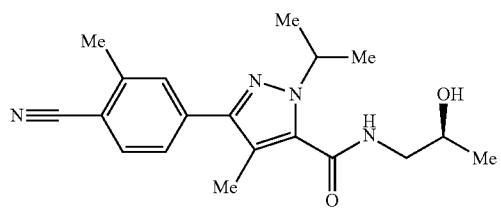

Using a procedure similar to that described for Example 1, but using the compound described in Preparation 11 and (S)-(+)-1-amino-2-propanol, the title compound was prepared as a solid (0.055 g, 54%). ¹H NMR (400 MHz, CDCl₃): δ 1.30 (d, 3H), 1.50 (d, 6H), 2.30 (s, 3H), 2.60 (s, 3H), 3.30 (m, 1H), 3.70 (m, 1H), 4.05 (m, 1H), 5.05 (m, 1H), 6.25 (m, 1H), 7.50 (m, 1H), 7.60 (d, 1H), 7.65 (d, 1H). LCMS $R_t$=1.79 mins ESCI MS m/z 341 [MH]⁺.

EXAMPLE 64

3-(4-Cyano-3-methylphenyl)-N-[(2R)-2-hydroxypropyl]-1-isopropyl-4-methyl-1H-pyrazole-5-carboxamide

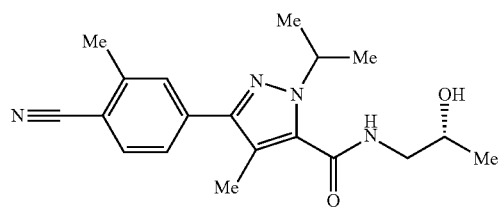

Using a procedure similar to that described for Example 1, but using the compound described in Preparation 11 and (R)-(+)-1-amino-2-propanol, the title compound was prepared as a solid (0.05 g, 49%). ¹H NMR (400 MHz, CDCl₃): δ 1.30 (d, 3H), 1.50 (d, 6H), 2.30 (s, 3H), 2.60 (s, 3H), 3.30 (m, 1H), 3.70 (m, 1H), 4.05 (m, 1H), 5.05 (m, 1H), 6.25 (m, 1H), 7.50 (m, 1H), 7.60 (d, 1H), 7.65 (d, 1H). LCMS $R_t$=1.79 mins ESCI MS m/z 341 [MH]⁺.

EXAMPLE 65

3-(4-Cyano-3-methylphenyl)-N-ethyl-1-isopropyl-4-methyl-1H-pyrazole-5-carboxamide

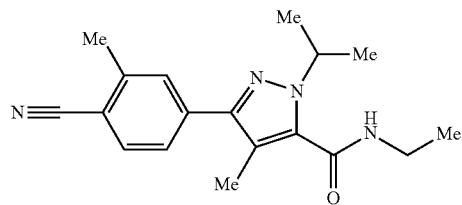

Using a procedure similar to that described for Example 1, but using the compound described in Preparation 11 and ethylamine hydrochloride, the title compound was prepared as a solid (0.06 g, 49%). LCMS $R_t$=2.18 mins ESCI MS m/z 311 [MH]⁺.

EXAMPLE 66

3-(4-Cyano-3-methylphenyl)-N,1-diisopropyl-4-methyl-1H-pyrazole-5-carboxamide

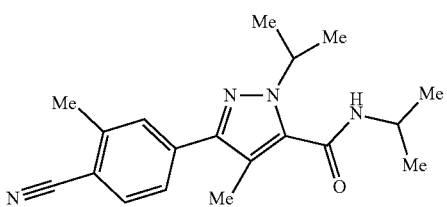

Using a procedure similar to that described for Example 1, but using the compound described in Preparation 11 and isopropylamine, the title compound was prepared as a solid (0.065 g, 40%). LCMS $R_t$=2.40 mins ESCI MS m/z 325 [MH]$^+$.

EXAMPLE 67

3-(4-Cyano-3-methylphenyl)-N-cyclopropyl-1-isopropyl-4-methyl-1H-pyrazole-5-carboxamide

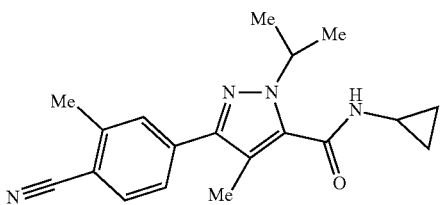

Using a procedure similar to that described for Example 1, but using the compound described in Preparation 11 and cyclopropylamine, the title compound was prepared as a solid (0.12 g, 49%). LCMS $R_t$=2.18 mins ESCI MS m/z 323 [MH]$^+$.

EXAMPLE 68

3-(4-Cyano-3-methylphenyl)-N-(2-hydroxy-2-methylpropyl)-1-isopropyl-4-methyl-1H-pyrazole-5-carboxamide

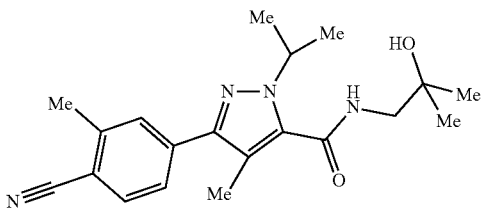

Using a procedure similar to that described for Example 1, but using the compound described in Preparation 11 and 1-amino-2-methyl-propan-2-ol hydrochloride, the title compound was prepared as a solid (0.063 g, 56%). $^1$H NMR (400 MHz, CDCl$_3$): δ 1.30 (s, 6H), 1.50 (d, 6H), 2.30 (s, 3H), 2.60 (s, 3H), 3.50 (d, 2H), 5.10 (m, 1H), 6.25 (m, 1H), 7.50 (m, 1H), 7.60 (d, 1H), 7.65 (d, 1H). LCMS $R_t$=1.93 mins ESCI MS m/z 355 [MH]$^+$.

EXAMPLE 69

3-(4-Cyanophenyl)-1-cyclobutyl-N-(cyclopropylmethyl)-4-methyl-1H-pyrazole-5-carboxamide

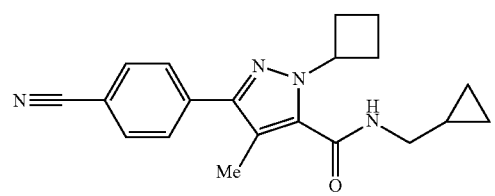

Using a procedure similar to that described for Example 1 but using the compound described in Preparation 16 and cyclopropylmethylamine, the title compound was prepared as a solid (0.034 g, 11%). LCMS $R_t$=2.45 mins ESCI MS m/z 335 [MH]$^+$.

EXAMPLE 70

3-(4-Cyanophenyl)-1-cyclobutyl-N,4-dimethyl-1H-pyrazole-5-carboxamide

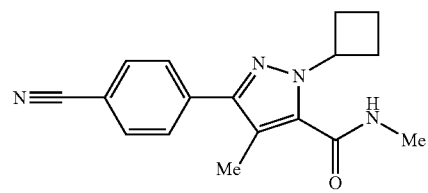

Using a procedure similar to that described for Example 1 but using the compound described in Preparation 16 and methylamine hydrochloride, the title compound was prepared as a solid (0.033 g, 46%). LCMS $R_t$=1.93 mins ESCI MS m/z 295 [MH]$^+$.

EXAMPLE 71

3-(4-Cyanophenyl)-1-cyclobutyl-N-cyclopropyl-4-methyl-1H-pyrazole-5-carboxamide

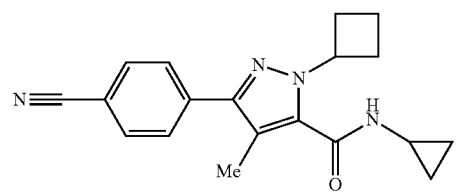

Using a procedure similar to that described for Example 1 but using the compound described in Preparation 16 and cyclopropylamine, the title compound was prepared as a solid (0.034 g, 44%). LCMS $R_t$=2.14 mins ESCI MS m/z 321 [MH]$^+$.

EXAMPLE 72

3-(4-Cyanophenyl)-1-cyclobutyl-N-[(2S)-2-hydroxypropyl]-4-methyl-1H-pyrazole-5-carboxamide

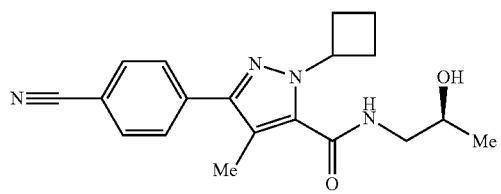

Using a procedure similar to that described for Example 1, but using the compound described in Preparation 16 and (S)-(+)-1-amino-2-propanol, the title compound was prepared as a solid (0.055 g, 56%). LCMS $R_t$=1.79 mins ESCI MS m/z 339 [MH]$^+$.

EXAMPLE 73

3-(4-Cyanophenyl)-1-cyclobutyl-N-[(2R)-2-hydroxypropyl]-4-methyl-1H-pyrazole-5-carboxamide

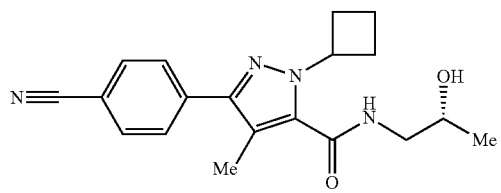

Using a procedure similar to that described for Example 1, but using the compound described in Preparation 16 and (R)-(+)-1-amino-2-propanol, the title compound was prepared as a solid (0.057 g, 58%). LCMS $R_t$=1.78 mins ESCI MS m/z 339 [MH]$^+$.

EXAMPLE 74

3-(4-Cyanophenyl)-1-cyclobutyl-N-(2-hydroxy-2-methylpropyl)-4-methyl-1H-pyrazole-5-carboxamide

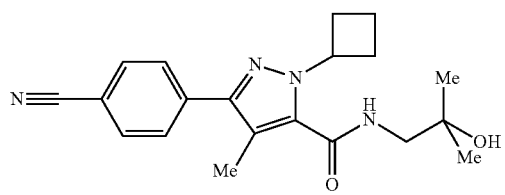

Using a procedure similar to that described for Example 1, but using the compound described in Preparation 16 and 1-amino-2-methyl-propan-2-ol hydrochloride, the title compound was prepared as a solid (0.05 g, 49%). LCMS $R_t$=1.91 mins ESCI MS m/z 353 [MH]$^+$.

EXAMPLE 75

3-(4-Cyanophenyl)-1-cyclobutyl-4-methyl-N-[2-(methylamino)-2-oxoethyl]-1H-pyrazole-5-carboxamide

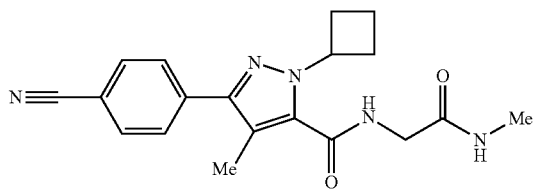

Using a procedure similar to that described for Example 1, but using the compound described in Preparation 16 and H-Gly-NHMe hydrochloride, the title compound was prepared as a solid (0.017 g, 17%). LCMS $R_t$=1.65 mins ESCI MS m/z 352 [MH]$^+$.

EXAMPLE 76

3-(4-Cyanophenyl)-N-ethyl-4-methyl-1-(tetrahydrofuran-3-yl)-1H-pyrazole-5-carboxamide

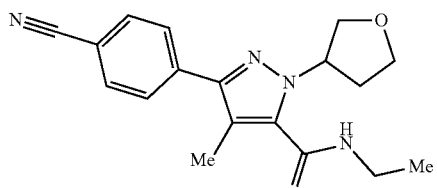

Using a procedure similar to that described for Example 1 but using the compound described in Preparation 23 and ethylamine hydrochloride, the title compound was prepared as a solid (0.084 g, 68%). LCMS $R_t$=1.72 mins ESCI MS m/z 325 [MH]$^+$.

This racemic mixture was separated by chiral preparative high performance liquid chromatography using a Chiralpak AS-H (250×20 mm id) eluting with 20% ethanol in heptane to give:
Enantiomer 1: LC $R_t$=10.45 mins
Enantiomer 2: LC $R_t$=11.98 mins

EXAMPLE 77

3-(4-Cyanophenyl)-N-isopropyl-4-methyl-1-(tetrahydrofuran-3-yl)-1H-pyrazole-5-carboxamide

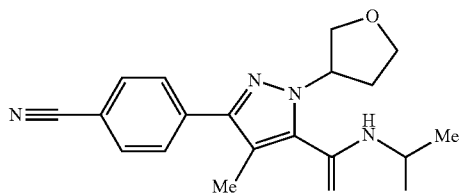

Using a procedure similar to that described for Example 1 but using the compound described in Preparation 23 and isopropylamine, the title compound was prepared as a solid (0.12 g, 70%). LCMS $R_t$=1.87 mins ESCI MS m/z 339 [MH]$^+$.

This racemic mixture was separated by chiral preparative high performance liquid chromatography using a Chiralpak AS-H (250×20 mm id) eluting with 10% ethanol in heptane to give:
Enantiomer 1: LC $R_t$=11.00 mins
Enantiomer 2: LC $R_t$=12.36 mins

EXAMPLE 78

3-(4-Cyanophenyl)-N-[(2S)-2-hydroxypropyl]-4-methyl-1-(tetrahydrofuran-3-yl)-1H-pyrazole-5-carboxamide

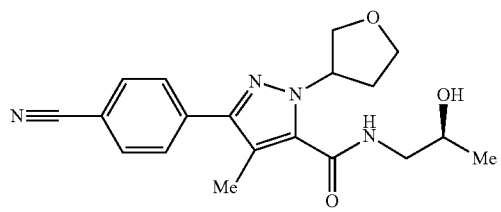

Using a procedure similar to that described for Example 1 but using the compound described in Preparation 23 and (S)-(+)-1-amino-2-propanol, the title compound was prepared as a solid (0.053 g, 36%). LCMS $R_t$=1.46 mins ESCI MS m/z 355 [MH]$^+$.

This mixture of diastereoisomers was separated by chiral preparative high performance liquid chromatography using a Chiralpak AD-H (250×21.2 mm id) eluting with 50% ethanol in methanol to give:
Diastereomer 1: LC $R_t$=4.22 mins
Diastereomer 2: LC $R_t$=5.19 mins

EXAMPLE 79

3-(4-Cyanophenyl)-N-[(2R)-2-hydroxypropyl]-4-methyl-1-(tetrahydrofuran-3-yl)-1H-pyrazole-5-carboxamide

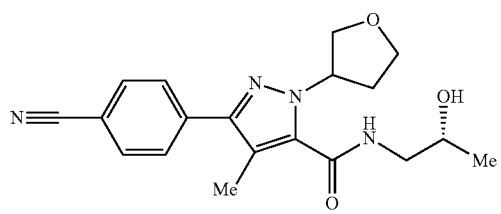

Using a procedure similar to that described for Example 1, but using the compound described in Preparation 23 and (R)-(+)-1-amino-2-propanol, the title compound was prepared as a solid (0.052 g, 36%). LCMS $R_t$=1.46 mins ESCI MS m/z 355 [MH]$^+$.

This mixture of diastereoisomers was separated by chiral preparative high performance liquid chromatography using a Chiralpak AS-H (250×20 mm id) eluting with 10% ethanol in heptane to give:
Diasteromer 1: LC $R_t$=4.40 mins
Diasteromer 2: LC $R_t$=5.44 mins

EXAMPLE 80

3-(4-Cyanophenyl)-N-(2-hydroxy-2-methylpropyl)-4-methyl-1-(tetrahydrofuran-3-yl)-1H-pyrazole-5-carboxamide

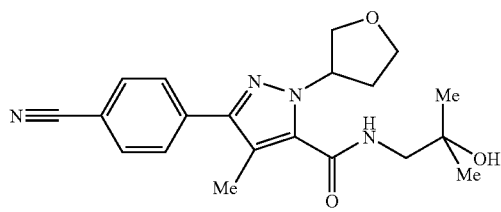

Using a procedure similar to that described for Example 1 but using the compound described in Preparation 23 and 1-amino-2-methyl-propan-2-ol hydrochloride, the title compound was prepared as a solid (0.05 g, 33%). LCMS $R_t$=1.57 mins ESCI MS m/z 369 [MH]$^+$.

This racemic mixture was separated by chiral preparative high performance liquid chromatography using a Chiralpak AS-H (250×20 mm id) eluting with 10% ethanol in heptane to give:
Enantiomer 1: LC $R_t$=3.94 mins
Enantiomer 2: LC $R_t$=4.57 mins

EXAMPLE 81

3-(4-Cyanophenyl)-1-cyclopropyl-N,4-dimethyl-1H-pyrazole-5-carboxamide

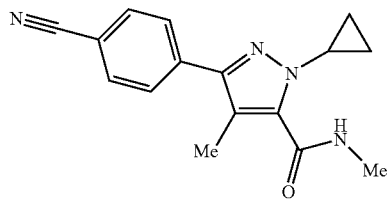

Using a procedure similar to that described for Example 1 but using the compound described in Preparation 29 and methylamine hydrochloride, the title compound was prepared as a solid (0.048 g, 35%). LCMS $R_t$=1.57 mins ESCI MS m/z 281 [MH]$^+$.

EXAMPLE 82

3-(4-Cyanophenyl)-1-cyclopropyl-N-(cyclopropylmethyl)-4-methyl-1H-pyrazole-5-carboxamide

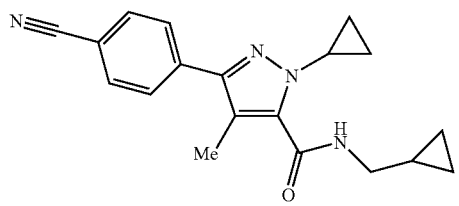

Using a procedure similar to that described for Example 1 but using the compound described in Preparation 29 and cyclopropylmethylamine, the title compound was prepared as a solid (0.096 g, 61%). LCMS $R_t$=1.98 mins ESCI MS m/z 321 [MH]$^+$.

EXAMPLE 83

3-(4-Cyanophenyl)-1-cyclopropyl-N-ethyl-4-methyl-1H-pyrazole-5-carboxamide

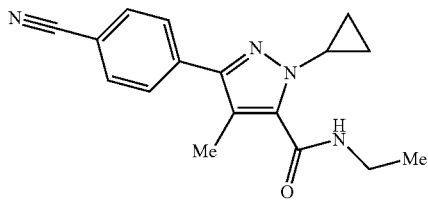

Using a procedure similar to that described for Example 1 but using the compound described in Preparation 29 and ethylamine hydrochloride, the title compound was prepared as a solid (0.074 g, 51%). LCMS $R_t$=1.72 mins ESCI MS m/z 295 [MH]$^+$.

EXAMPLE 84

3-(4-Cyanophenyl)-N,1-dicyclopropyl-4-methyl-1H-pyrazole-5-carboxamide

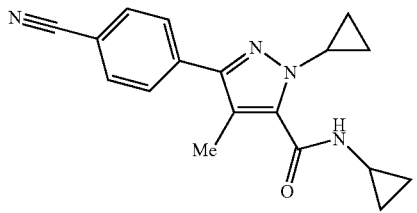

Using a procedure similar to that described for Example 1 but using the compound described in Preparation 29 and cyclopropylamine, the title compound was prepared as a solid (0.081 g, 54%). LCMS $R_t$=1.72 mins ESCI MS m/z 307 [MH]$^+$.

EXAMPLE 85

3-(4-Cyanophenyl)-1-cyclopropyl-N-isopropyl-4-methyl-1H-pyrazole-5-carboxamide

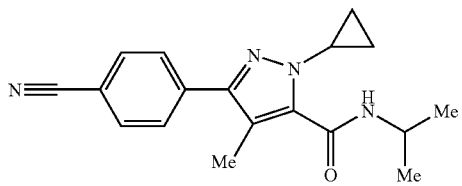

Using a procedure similar to that described for Example 1, but using the compound described in Preparation 29 and isopropylamine, the title compound was prepared as a solid (0.06 g, 40%). LCMS $R_t$=1.91 mins ESCI MS m/z 309 [MH]$^+$.

EXAMPLE 86

3-(4-Cyanophenyl)-1-cyclopropyl-N-[(2S)-2-hydroxypropyl]-4-methyl-1H-pyrazole-5-carboxamide

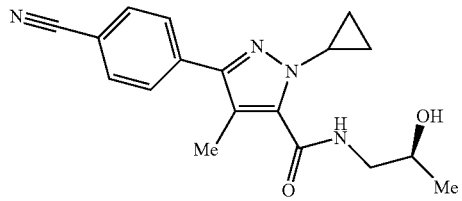

Using a procedure similar to that described for Example 1, but using the compound described in Preparation 29 and (S)-(+)-1-amino-2-propanol, the title compound was prepared as a solid (0.05 g, 44%). LCMS $R_t$=1.46 mins ESCI MS m/z 325 [MH]$^+$.

EXAMPLE 87

3-(4-Cyanophenyl)-1-cyclopropyl-N-[(2R)-2-hydroxypropyl]-4-methyl-1H-pyrazole-5-carboxamide

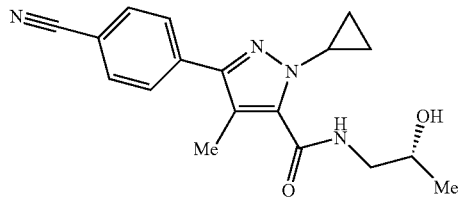

Using a procedure similar to that described for Example 1, but using the compound described in Preparation 29 and (R)-(+)-1-amino-2-propanol, the title compound was prepared as a solid (0.05 g, 44%). LCMS $R_t$=1.46 mins ESCI MS m/z 325 [MH]$^+$.

EXAMPLE 88

3-(4-Cyanophenyl)-1-cyclopropyl-N-(2-hydroxy-2-methylpropyl)-4-methyl-1H-pyrazole-5-carboxamide

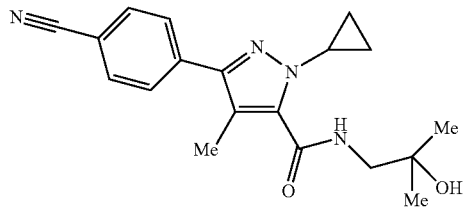

Using a procedure similar to that described for Example 1, but using the compound described in Preparation 29 and 1-amino-2-methyl-propan-2-ol hydrochloride, the title compound was prepared as a solid (0.05 g, 42%). LCMS $R_t$=1.51 mins ESCI MS m/z 339 [MH]$^+$.

EXAMPLE 89

4-Cyano-3-(4-cyanophenyl)-N-ethyl-1-isopropyl-1H-pyrazole-5-carboxamide

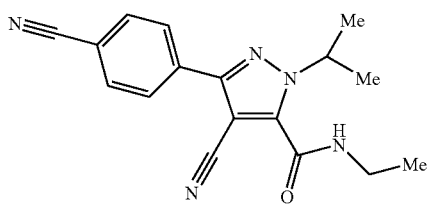

Using a procedure similar to that described for Example 58, but using the compound described in Preparation 36 and ethylamine hydrochloride, the title compound was prepared as a solid (0.025 g, 46%). $^1$H NMR (400 MHz, CDCl$_3$): δ 1.30 (t, 3H), 1.55 (d, 6H), 3.55 (q, 2H), 5.45 (m, 1H), 6.45 (m, 1H), 7.75 (d, 2H), 8.10 (d, 2H). LCMS $R_t$=2.13 mins ESCI MS m/z 308 [MH]$^+$.

EXAMPLE 90

3-(4-Cyano-3-methylphenyl)-1-isopropyl-N,4-dimethyl-1H-pyrazole-5-carboxamide

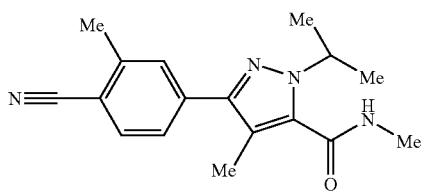

Using a procedure similar to that described for Example 1, but using the compound described in Preparation 11 and a solution of methylamine in tetrahydrofuran (2M), the title compound was prepared as a solid (0.20 g, 70%). LCMS $R_t$=1.94 mins ESCI MS m/z 297 [MH]$^+$.

EXAMPLE 91

4-Cyano-3-(4-cyanophenyl)-N,1-diisopropyl-1H-pyrazole-5-carboxamide

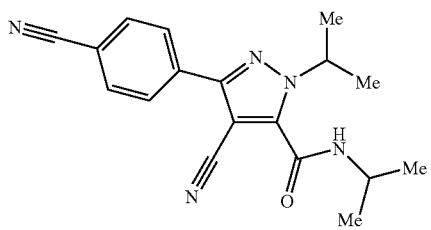

Using a procedure similar to that described for Example 58, but using the compound described in Preparation 36 and isopropylamine, the title compound was prepared as a solid (0.026 g, 45%). $^1$H NMR (400 MHz, CDCl$_3$): δ 1.30 (d, 6H), 1.55 (d, 6H), 4.30 (m, 1H), 5.45 (m, 1H), 6.30 (m, 1H), 7.75 (d, 2H), 8.10 (d, 2H). LCMS $R_t$=2.31 mins ESCI MS m/z 322 [MH]$^+$.

EXAMPLE 92

4-Cyano-3-(4-cyanophenyl)-1-isopropyl-N-methyl-1H-pyrazole-5-carboxamide

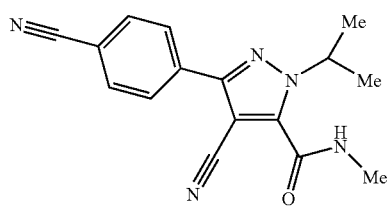

Using a procedure similar to that described for Example 58, but using the compound described in Preparation 36 and a solution of methylamine in tetrahydrofuran (2M), the title compound was prepared as a solid (0.024 g, 46%). LCMS $R_t$=1.94 mins ESCI MS m/z 294 [MH]$^+$.

EXAMPLE 93

4-Cyano-3-(4-cyanophenyl)-N-(cyclopropylmethyl)-1-isopropyl-1H-pyrazole-5-carboxamide

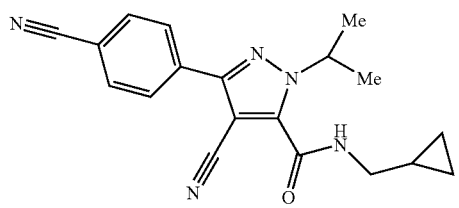

Using a procedure similar to that described for Example 58, but using the compound described in Preparation 36 and cyclopropylmethylamine, the title compound was prepared as a solid (0.024 g, 40%). LCMS $R_t$=2.43 mins ESCI MS m/z 334 [MH]$^+$.

EXAMPLE 94

4-Cyano-3-(4-cyanophenyl)-N-cyclopropyl-1-isopropyl-1H-pyrazole-5-carboxamide

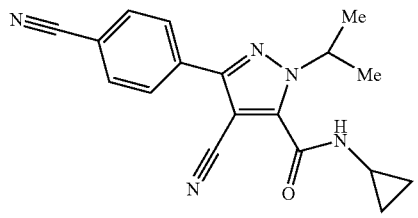

Using a procedure similar to that described for Example 58, but using the compound described in Preparation 36 and cyclopropylamine, the title compound was prepared as a solid (0.26 g, 46%). $^1$H NMR (400 MHz, CDCl$_3$): δ 0.75 (m, 2H), 0.95 (m, 2H), 1.55 (d, 6H), 2.95 (m, 1H), 5.45 (m, 1H), 6.60 (m, 1H), 7.75 (d, 2H), 8.10 (d, 2H). LCMS R$_t$=2.17 mins ESCI MS m/z 320 [MH]$^+$.

EXAMPLE 95

4-Benzyl-3-(4-cyanophenyl)-N,1-diisopropyl-1H-pyrazole-5-carboxamide

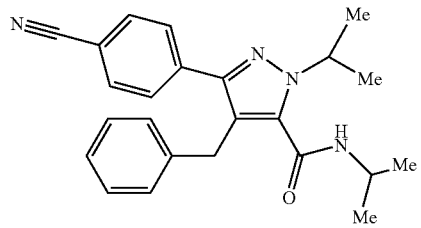

Using a procedure similar to that described for Example 1, but using the compound described in Preparation 41 and isopropylamine, the title compound was prepared as a solid (0.049 g, 35%). LCMS R$_t$=1.66 mins ESCI MS m/z 387 [MH]$^+$.

EXAMPLE 96

4-Benzyl-3-(4-cyanophenyl)-N-cyclopropyl-1-isopropyl-1H-pyrazole-5-carboxamide

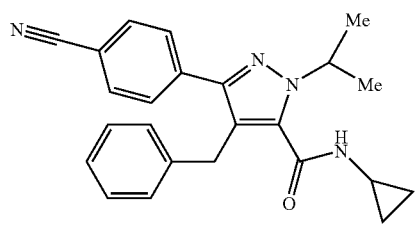

Using a procedure similar to that described for Example 1, but using the compound described in Preparation 41 and cyclopropylamine, the title compound was prepared as a solid (0.026 g, 19%). $^1$H NMR (400 MHz, CDCl$_3$): δ 0.00 (m, 2H), 0.60 (m, 2H), 0.95 (m, 1H), 1.45 (d, 6H), 2.45 (m, 1H), 4.00 (s, 2H), 5.15 (m, 1H), 5.50 (m, 1H), 7.05 (m, 2H), 7.25 (m, 3H), 7.55 (d, 2H), 7.60 (d, 2H). ESCI MS m/z 385 [MH]$^+$.

EXAMPLE 97

4-Benzyl-3-(4-cyanophenyl)-N-ethyl-1-isopropyl-1H-pyrazole-5-carboxamide

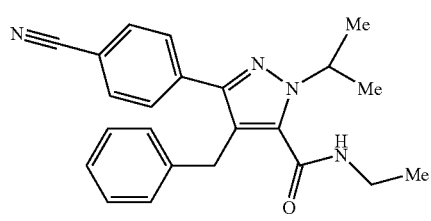

Using a procedure similar to that described for Example 1, but using the compound described in Preparation 41 and ethylamine hydrochloride, the title compound was prepared as a solid (0.055 g, 41%). LCMS R$_t$=1.57 mins ESCI MS m/z 373 [MH]$^+$.

EXAMPLE 98

3-(4-Cyanophenyl)-N-cyclopropyl-4-(3,3-difluorocyclobutyl)-1-isopropyl-1H-pyrazole-5-carboxamide

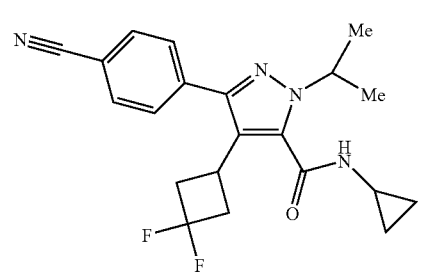

Using a procedure similar to that described for Example 5, but using the compound described in Preparation 50 and cyclopropylamine, the title compound was prepared as a solid (0.031 g, 62%). LCMS R$_t$=1.56 mins ESCI MS m/z 385 [MH]$^+$.

EXAMPLE 99

3-(4-Cyanophenyl)-4-(3,3-difluorocyclobutyl)-1-isopropyl-N-methyl-1H-pyrazole-5-carboxamide

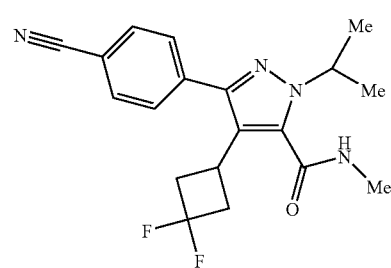

Prepared using a procedure similar to that described for Example 5, but using the compound described in Preparation 50 and methylamine hydrochloride, the title compound was purified by high performance liquid chromatography. LCMS R$_t$=3.50 mins ESCI MS m/z 359 [MH]$^+$.

EXAMPLE 100

3-(4-Cyanophenyl)-4-(3,3-difluorocyclobutyl)-N-ethyl-1-isopropyl-1H-pyrazole-5-carboxamide

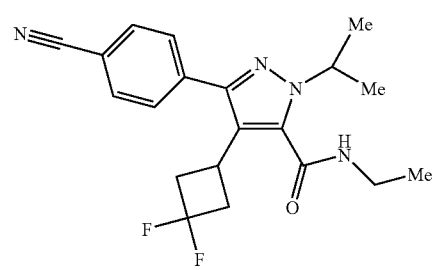

Prepared using a procedure similar to that described for Example 5, but using the compound described in Preparation 50 and ethylamine hydrochloride, the title compound was purified by high performance liquid chromatography. LCMS $R_t$=3.51 mins ESCI MS m/z 373 [MH]$^+$.

EXAMPLE 101

(+/−)-1-sec-Butyl-3-(4-cyanophenyl)-N-(cyclopropylmethyl)-4-ethyl-1H-pyrazole-5-carboxamide

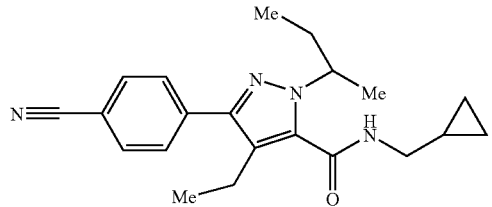

Using a procedure similar to that described for Example 1, but using the compound described in Preparation 59 and cyclopropylmethylamine, the title compound was prepared as a solid (0.026 g, 39%). LCMS $R_t$=2.59 mins ESCI MS m/z 351 [MH]$^+$.

EXAMPLE 102

(+/−)-1-sec-Butyl-3-(4-cyanophenyl)-4-ethyl-N-isopropyl-1H-pyrazole-5-carboxamide

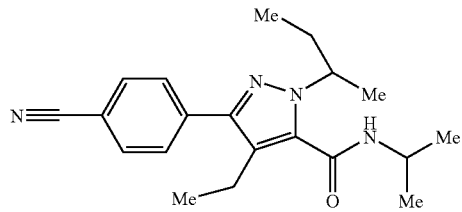

Using a procedure similar to that described for Example 1, but using the compound described in Preparation 59 and isopropylamine, the title compound was prepared as a solid (0.027 g, 42%). LCMS $R_t$=2.49 mins ESCI MS m/z 339 [MH]$^+$.

EXAMPLE 103

(+/−)-1-sec-Butyl-3-(4-cyanophenyl)-N,4-diethyl-1H-pyrazole-5-carboxamide

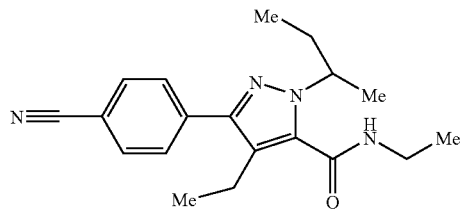

Using a procedure similar to that described for Example 1, but using the compound described in Preparation 59 and ethylamine hydrochloride, the title compound was prepared as a solid (0.02 g, 33%). LCMS $R_t$=2.29 mins ESCI MS m/z 325 [MH]$^+$.

EXAMPLE 104

(+/−)-1-sec-Butyl-3-(4-cyanophenyl)-N-cyclopropyl-4-ethyl-1H-pyrazole-5-carboxamide

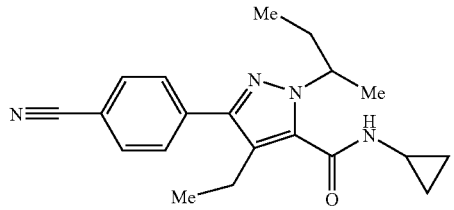

Using a procedure similar to that described for Example 1, but using the compound described in Preparation 59 and cyclopropylamine, the title compound was prepared as a solid (0.024 g, 38%). LCMS $R_t$=2.29 mins ESCI MS m/z 337 [MH]$^+$.

EXAMPLE 105

(+/−)-1-sec-Butyl-3-(4-cyanophenyl)-4-ethyl-N-methyl-1H-pyrazole-5-carboxamide

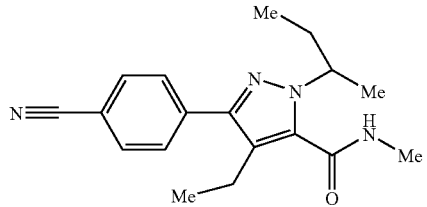

Using a procedure similar to that described for Example 1, but using the compound described in Preparation 59 and a solution of methylamine in tetrahydrofuran (2M), the title compound was prepared as a solid (0.017 g, 29%). LCMS $R_t$=2.07 mins ESCI MS m/z 311 [MH]$^+$.

EXAMPLE 106

1-sec-Butyl-3-(4-cyanophenyl)-4-ethyl-N-(2-hydroxy-2-methylpropyl)-1H-pyrazole-5-carboxamide

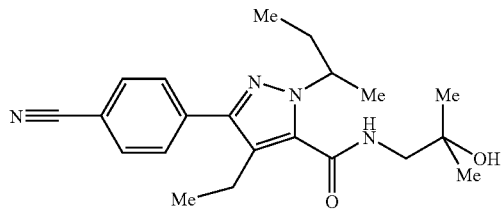

Using a procedure similar to that described for Example 1, but using the compound described in Preparation 59 and 1-amino-2-methyl-propan-2-ol hydrochloride, the title compound was prepared as a solid (0.07 g, 55%). LCMS $R_t$=2.09 mins ESCI MS m/z 369 [MH]$^+$.

This racemic mixture was separated by chiral preparative high performance liquid chromatography using a Chiralpak AD-H (250×21.2 mm id) eluting with 10% 2-propanol in heptane to give:

Enantiomer 1 LCMS $R_t$=2.24 mins APCI MS m/z 369 [MH]$^+$
Enantiomer 2 LCMS $R_t$=2.24 mins APCI MS m/z 369 [MH]$^+$

EXAMPLE 107

1-sec-Butyl-3-(4-cyanophenyl)-4-ethyl-N-[(2R)-2-hydroxypropyl]-1H-pyrazole-5-carboxamide

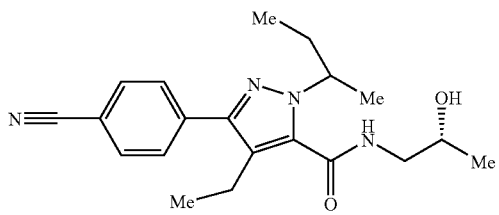

Using a procedure similar to that described for Example 1, but using the compound described in Preparation 59 and (R)-(+)-1-amino-2-propanol, the title compound was prepared as a solid (0.076 g, 62%). LCMS $R_t$=1.87 mins ESCI MS m/z 355 [MH]$^+$.

This mixture of diastereoisomers was separated by chiral preparative high performance liquid chromatography using a Chiralpak AD-H (250×21.2 mm id) eluting with 10% 2-propanol in heptane to give:

Diastereomer 1 LCMS $R_t$=1.87 mins APCI MS m/z 355 [MH]$^+$
Diastereomer 2 LCMS $R_t$=1.87 mins APCI MS m/z 355 [MH]$^+$

EXAMPLE 108

1-sec-Butyl-3-(4-cyanophenyl)-4-ethyl-N-[(2S)-2-hydroxypropyl]-1H-pyrazole-5-carboxamide

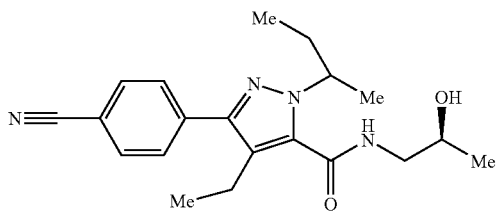

Using a procedure similar to that described for Example 1, but using the compound described in Preparation 59 and (S)-(+)-1-amino-2-propanol, the title compound was prepared as a solid (0.075 g, 61%). LCMS $R_t$=1.87 mins ESCI MS m/z 355 [MH]$^+$.

EXAMPLE 109

1-sec-Butyl-3-(4-cyanophenyl)-4-ethyl-N-[2-(methylamino)-2-oxoethyl]-1H-pyrazole-5-carboxamide

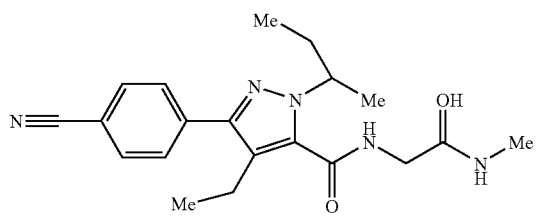

Using a procedure similar to that described for Example 1, but using the compound described in Preparation 59 and H-Gly-NHMe hydrochloride. The title compound was prepared as a solid (0.06 g, 47%). LCMS $R_t$=1.77 mins ESCI MS m/z 368 [MH]$^+$.

This racemic mixture was separated by chiral preparative high performance liquid chromatography using a Chiralpak AD-H (250×20 mm id) eluting with 10% 2-propanol in heptane to give:

Enantiomer 1 LCMS $R_t$=1.76 mins APCI MS m/z 368 [MH]$^+$
Enantiomer 2 LCMS $R_t$=1.76 mins APCI MS m/z 368 [MH]$^+$

EXAMPLE 110

3-(4-Cyanophenyl)-N-(cyclopropylmethyl)-4-ethyl-1-isopropyl-1H-pyrazole-5-carboxamide

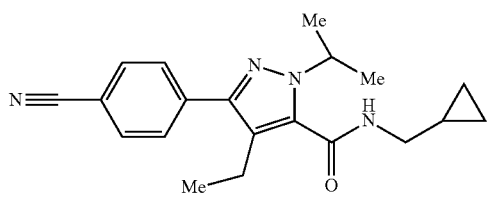

Using a procedure similar to that described for Example 1, but using the compound described in Preparation 55 and cyclopropylmethylamine, the title compound was prepared as a solid (0.088 g, 44%). LCMS $R_t$=2.40 mins ESCI MS m/z 337 [MH]$^+$.

EXAMPLE 111

3-(4-Cyanophenyl)-N-cyclopropyl-4-ethyl-1-isopropyl-1H-pyrazole-5-carboxamide

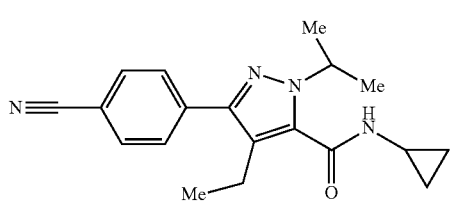

Using a procedure similar to that described for Example 1, but using the compound described in Preparation 55 and cyclopropylamine, the title compound was prepared as a solid (0.11 g, 58%). LCMS $R_t$=2.10 mins ESCI MS m/z 323 [MH]$^+$.

EXAMPLE 112

3-(4-Cyanophenyl)-4-ethyl-1-isopropyl-N-methyl-1H-pyrazole-5-carboxamide

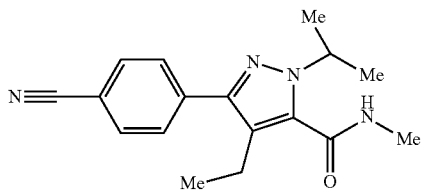

Using a procedure similar to that described for Example 1, but using the compound described in Preparation 55 and a solution of methylamine in tetrahydrofuran (2M), the title compound was prepared as a solid (0.103 g, 58%). LCMS $R_t$=1.99 mins ESCI MS m/z 297 [MH]$^+$.

EXAMPLE 113

3-(4-Cyano-3-methylphenyl)-1-isopropyl-4-methyl-N-[2-(methylamino)-2-oxoethyl]-1H-pyrazole-5-carboxamide

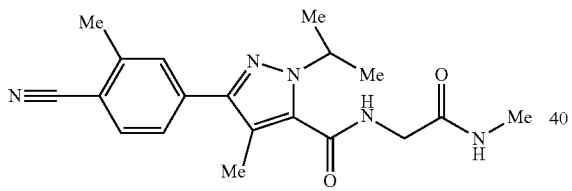

Using a procedure similar to that described for Example 1, but using the compound described in Preparation 11 and H-Gly-NHMe hydrochloride, the title compound was prepared as a solid (0.056 g, 50%). LCMS $R_t$=1.65 mins ESCI MS m/z 354 [MH]$^+$.

EXAMPLE 114

3-(4-Cyanophenyl)-4-ethyl-N-[(2S)-2-hydroxypropyl]-1-isopropyl-1H-pyrazole-5-carboxamide

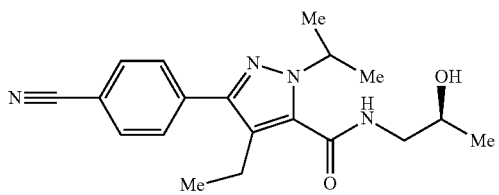

Using a procedure similar to that described for Example 1, but using the compound described in Preparation 55 and (S)-(+)-1-amino-2-propanol, the title compound was prepared as a solid (0.060 g, 53%). LCMS $R_t$=1.68 mins ESCI MS m/z 341 [MH]$^+$.

EXAMPLE 115

3-(4-Cyanophenyl)-4-ethyl-N-[(2R)-2-hydroxypropyl]-1-isopropyl-1H-pyrazole-5-carboxamide

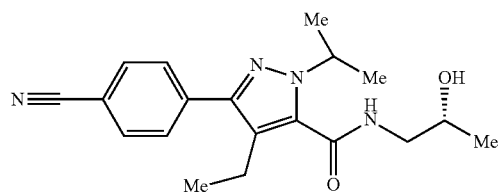

Using a procedure similar to that described for Example 1, but using the compound described in Preparation 55 and (R)-(+)-1-amino-2-propanol, the title compound was prepared as a solid (0.067 g, 59%). LCMS $R_t$=1.68 mins ESCI MS m/z 341 [MH]$^+$.

EXAMPLE 116

3-(4-Cyanophenyl)-N,4-diethyl-1-isopropyl-1H-pyrazole-5-carboxamide

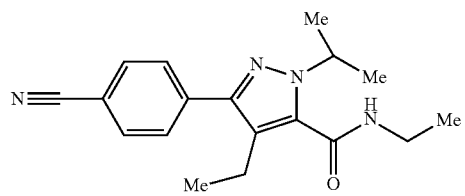

Using a procedure similar to that described for Example 1, but using the compound described in Preparation 55 and ethylamine hydrochloride, the title compound was prepared as a solid (0.086 g, 46%). LCMS $R_t$=2.06 mins ESCI MS m/z 311 [MH]$^+$.

EXAMPLE 117

3-(4-Cyanophenyl)-4-ethyl-N,1-diisopropyl-1H-pyrazole-5-carboxamide

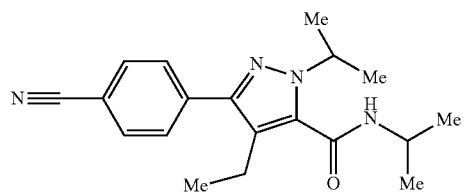

Using a procedure similar to that described for Example 1, but using the compound described in Preparation 55 and isopropylamine, the title compound was prepared as a solid (0.114 g, 59%). LCMS R$_t$=2.28 mins ESCI MS m/z 325 [MH]$^+$.

EXAMPLE 118

3-(4-Cyanophenyl)-4-ethyl-N-(2-hydroxy-2-methyl-propyl)-1-isopropyl-1H-pyrazole-5-carboxamide

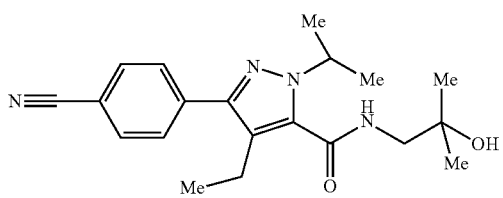

Using a procedure similar to that described for Example 1, but using the compound described in Preparation 55 and 1-amino-2-methyl-propan-2-ol hydrochloride, the title compound was prepared as a solid (0.061 g, 52%). LCMS R$_t$=1.77 mins ESCI MS m/z 355 [MH]$^+$.

EXAMPLE 119

3-(4-Cyanophenyl)-4-ethyl-1-isopropyl-N-[2-(methylamino)-2-oxoethyl]-1H-pyrazole-5-carboxamide

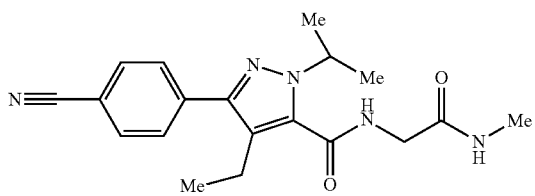

Using a procedure similar to that described for Example 1, but using the compound described in Preparation 55 and H-Gly-NHMe hydrochloride, the title compound was prepared as a solid (0.05 g, 43%). LCMS R$_t$=1.57 mins ESCI MS m/z 354 [MH]$^+$.

EXAMPLE 120

3-(4-Cyano-3-methylphenyl)-4-cyclopropyl-1-isopropyl-N-[2-(methylamino)-2-oxoethyl]-1H-pyrazole-5-carboxamide

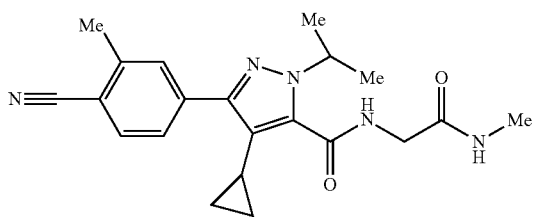

Benzotriazol-1-yloxy-tris(dimethylamino)phosphonium hexafluorophosphate (86 mg, 0.19 mmol) was added to a solution of the compound described in Preparation 64 (50 mg, 0.16 mmol) and H-Gly-NHMe hydrochloride (24 mg, 0.19 mmol) in N,N-dimethylformamide (1 mL), cooled to 5° C., followed by diisopropylethylamine (0.23 mL, 0.65 mmol). This mixture was stirred at room temperature for 16 hours. The reaction mixture was then diluted with ethyl acetate (25 mL), and washed with a 10% w/v aqueous solution of citric acid (10 mL), followed by a saturated aqueous solution of sodium hydrogen carbonate (10 mL) and brine (10 mL). The organic extracts were dried over magnesium sulphate, filtered, and evaporated under reduced pressure to give a gum. This crude residue was purified by column chromatography eluting with 30% dichloromethane in ethyl acetate to give the title compound as a solid (0.042 g, 68%). $^1$H NMR (400 MHz, CDCl$_3$): δ 0.35 (m, 2H), 1.05 (m, 2H), 1.50 (d, 6H), 1.85 (m, 1H), 2.60 (s, 3H), 2.90 (d, 3H), 4.15 (d, 2H), 5.40 (m, 1H), 5.85 (m, 1H), 7.45 (m, 1H), 7.65 (m, 1H), 7.70 (m, 1H), 7.75 (d, 1H). LCMS R$_t$=1.87 mins ESCI MS m/z 380 [MH]$^+$.

The following Examples 121-134 were prepared using similar procedures to those described in Examples 1, 77 and 89 using intermediates prepared in Preparations 5, 23, 36, 59 and 72-78.

EXAMPLE 121

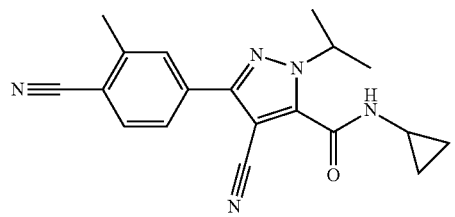

$^1$H NMR (400 MHz, CDCl$_3$): δ 0.70-0.78 (m, 2H), 0.90-1.00 (m, 2H), 1.56 (d, 6H), 2.60 (s, 3H), 2.90-2.95 (m, 1H), 5.49 (septet, 1H), 6.60 (br s, 1H), 7.70 (d, 1H), 7.90-7.95 (m, 2H).

EXAMPLE 122

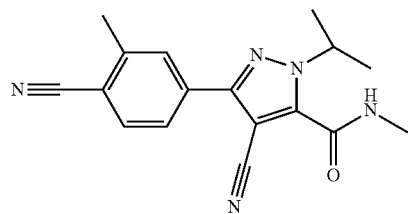

$^1$H NMR (400 MHz, CDCl$_3$): δ 1.54 (d, 6H), 2.63 (s, 3H), 3.08 (d, 3H), 5.45-5.50 (m, 1H), 6.50 (br s, 1H), 7.69 (d, 1H), 7.91 (d, 1H), 7.94 (s, 1H).

EXAMPLE 123

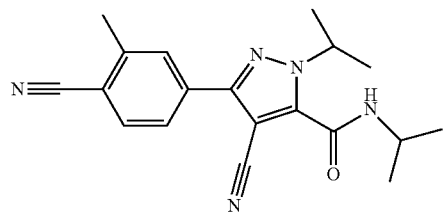

$^1$H NMR (400 MHz, CDCl$_3$): δ 1.31 (d, 6H), 1.58 (d, 6H), 2.63 (s, 3H), 4.26 (septet, 1H), 5.43 (septet, 1H), 6.28 (br s, 1H), 7.69 (d, 1H), 7.91 (d, 1H), 7.94 (s, 1H).

EXAMPLE 124

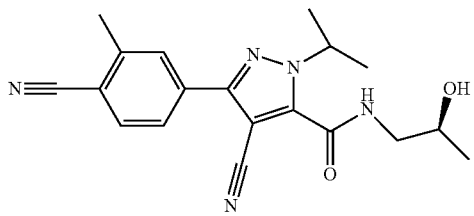

$^1$H NMR (400 MHz, CDCl$_3$): δ 1.32 (d, 3H), 1.59 (dd, 6H), 2.05 (d, 1H), 2.63 (s, 3H), 3.30-3.40 (m, 1H), 3.70-3.78 (m, 1H), 4.08-4.16 (m, 1H), 5.40 (septet, 1H), 6.90 (br s, 1H), 7.68 (d, 1H), 7.91 (d, 1H), 7.94 (s, 1H). LCMS R$_t$=2.24 mins ESCI MS m/z 350 [M−H$^+$].

EXAMPLE 125

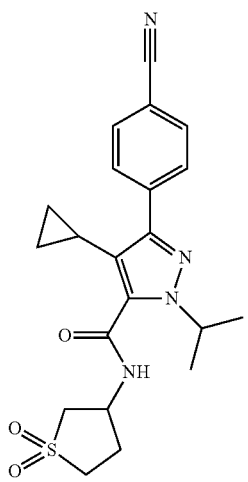

$^1$H NMR (400 MHz, CDCl$_3$): δ 0.46-0.51 (m, 2H), 1.00-1.04 (m, 2H), 1.46 (d, 6H), 1.80-1.90 (m, 1H), 2.37-2.50 (m, 1H), 2.60-2.70 (m, 1H), 3.00-3.30 (m, 3H), 3.42 (dd, 1H), 5.00-5.10 (m, 1H), 5.30-5.40 (m, 1H), 7.64 (d, 2H), 7.91 (d, 2H). LCMS R$_t$=2.92 mins ESCI MS m/z 413 [MH]$^+$.

EXAMPLE 126

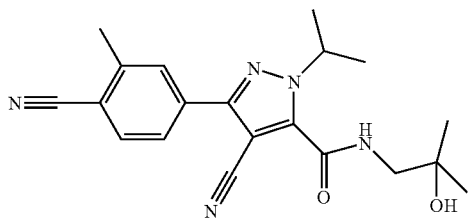

$^1$H NMR (400 MHz, CDCl$_3$): δ 1.38 (s, 6H), 1.55 (d, 6H), 2.60 (s, 3H), 3.50 (d, 2H), 5.49 (septet, 1H), 6.93 (br s, 1H), 7.65 (d, 1H), 7.89 (d, 1H), 7.96 (s, 1H).

EXAMPLE 127

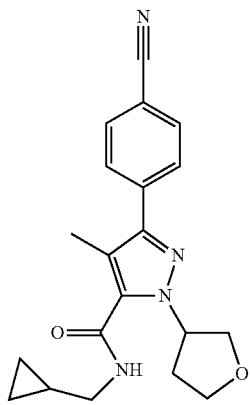

LCMS R$_t$=2.02 mins ESCI MS m/z 351 [MH]$^+$.

EXAMPLE 128

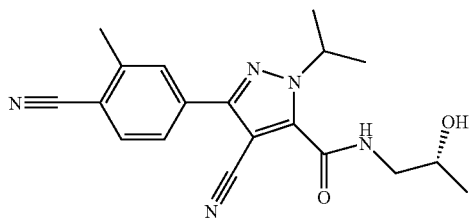

$^1$H NMR (400 MHz, CDCl$_3$): δ 1.31 (d, 3H), 1.57 (d, 6H), 2.03 (d, 1H), 2.62 (s, 3H), 3.30-3.38 (m, 1H), 3.70-3.76 (m, 1H), 4.06-4.16 (m, 1H), 5.40 (septet, 1H), 6.85 (br s, 1H), 7.70 (d, 1H), 7.91 (d, 1H), 7.95 (s, 1H). LCMS R$_t$=2.51 mins ESCI MS m/z 350 [M−H$^+$].

EXAMPLE 129

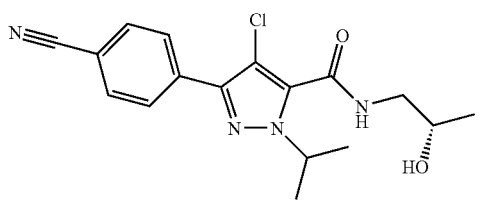

$^1$H NMR (400 MHz, CDCl$_3$): δ 1.30 (d, 3H), 1.57 (d, 6H), 2.05 (d, 1H), 3.30-3.39 (m, 1H), 3.65-3.72 (m, 1H), 4.02-4.16

(m, 1H), 5.45 (septet, 1H), 7.01 (br s, 1H), 7.72 (d, 2H), 8.02 (d, 2H). LCMS $R_t$=2.76 mins ESCI MS m/z 347, 349 [MH]$^+$.

EXAMPLE 130

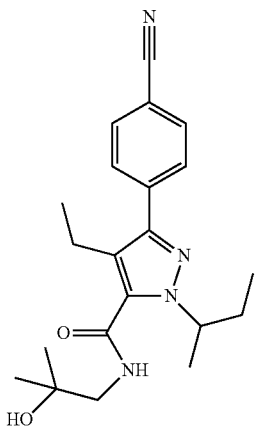

$^1$H NMR (400 MHz, CDCl$_3$): δ 0.80 (t, 3H), 1.25 (t, 3H), 1.32 (s, 6H), 1.50 (d, 3H), 1.60 (br s, 1H), 1.75-1.85 (m, 1H), 1.96-2.08 (m, 1H), 2.75 (q, 2H), 3.45-3.55 (m, 2H), 4.63-4.75 (m, 1H), 6.33 (br s, 1H), 7.68 (d, 2H), 7.77 (d, 2H). LCMS $R_t$=2.14 mins ESCI MS m/z 369 [MH]$^+$.

EXAMPLE 131

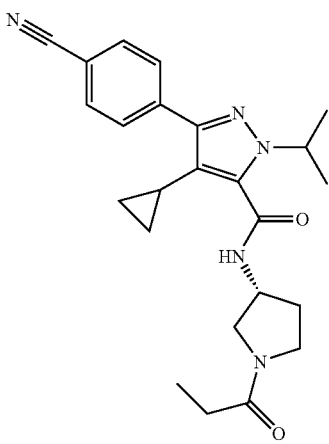

LCMS $R_t$=1.48 mins ESCI MS m/z 420 [MH]$^+$.

EXAMPLE 132

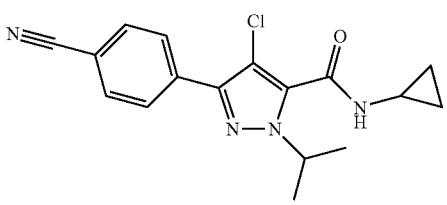

$^1$H NMR (400 MHz, CDCl$_3$): δ 0.62-0.70 (m, 2H), 0.90-0.98 (m, 2H), 1.50 (d, 6H), 2.90-2.95 (m, 1H), 5.50 (septet, 1H), 6.68 (br s, 1H), 7.71 (d, 2H), 8.01 (d, 2H). LCMS $R_t$=3.41 mins ESCI MS m/z 329, 331 [MH]$^+$.

EXAMPLE 133

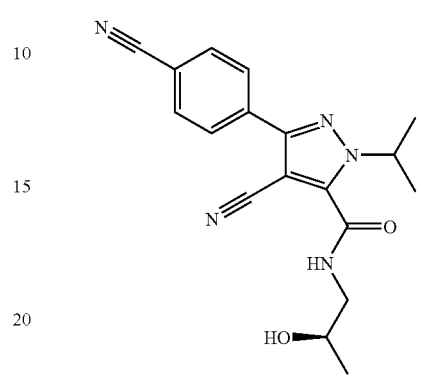

$^1$H NMR (400 MHz, CDCl$_3$): δ 1.31 (d, 3H), 1.58 (d, 6H), 2.01 (d, 1H), 3.30-3.40 (m, 1H), 3.70-3.80 (m, 1H), 4.06-4.16 (m, 1H), 5.40 (septet, 1H), 6.0 (br s, 1H), 7.78 (d, 2H), 8.13 (d, 2H). LCMS $R_t$=2.18 mins ESCI MS m/z 338

EXAMPLE 134

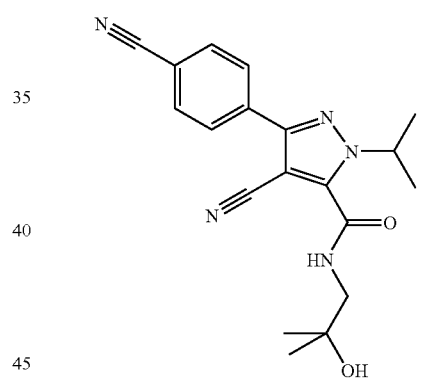

$^1$H NMR (400 MHz, CDCl$_3$): δ 1.95 (s, 6H), 1.58 (d, 6H), 1.98 (s, 1H), 3.50 (d, 2H), 5.39 (septet, 1H), 6.92 (br s, 1H), 7.77 (d, 2H), 8.10 (d, 2H). LCMS $R_t$=2.44 mins ESCI MS m/z 350 [M−H$^+$].

The following Preparations illustrate the synthesis of certain starting materials and intermediates used in the above Examples.

Preparation 1:
4-[Cyano(cyclopropyl)acetyl]benzonitrile

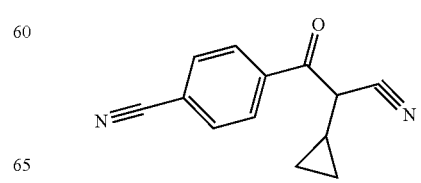

A 2.5 molar solution of n-butyl lithium (114 mL, 285 mmol) in hexane was added to a cooled (−78° C.) solution of diisopropylamine (38.3 mL, 273 mmol) in tetrahydrofuran (300 mL). This cooled reaction mixture was then allowed to stir for 1 hour, after which time cyclopropylacetonitrile (20.8 mL, 261 mmol) was added at such a rate as to keep the temperature below −60° C. This mixture was then allowed to stir at −78° C. for 1 hour, after which time a solution of 4-cyano-benzoic acid methyl ester (40 g, 248 mmol) in tetrahydrofuran (100 mL) was added at such a rate as to keep the temperature below −60° C. This mixture was then slowly warmed to room temperature and stirred for 18 hours after which time it was quenched onto an aqueous 10% solution (weight/volume) citric acid (600 mL) and extracted with ethyl acetate (2×2500 mL). The organic extracts were washed with brine (600 mL), dried over magnesium sulphate, filtered, and evaporated under reduced pressure to give a brown oil (52.7 g, 100%). This material was used for subsequent steps without further purification. $^1$H NMR (400 MHz, CDCl$_3$): δ 0.60 (m, 2H), 0.80 (m, 2H), 1.40 (m, 1H), 4.10 (d, 1H), 7.85 (d, 2H), 8.10 (d, 2H). ESCI MS m/z 243 [M−H]$^-$ Preparation 2: 4-(5-Amino-4-cyclopropyl-1-isopropyl-1H-pyrazol-3-yl)benzonitrile

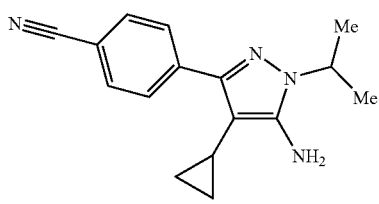

Isopropylhydrazine hydrochloride (31.4 g, 284 mmol) and diisopropylethylamine (90 mL, 517 mmol) were added to a solution of the compound described in Preparation 1 (54.3 g, 258 mmol) in ethanol (550 mL) followed by acetic acid (88.7 mL, 1550 mmol). This mixture was stirred at 60° C. for 16 hours. It was then cooled to room temperature and concentrated under reduced pressure. The crude material was partitioned between ethyl acetate (500 mL) and a saturated aqueous solution of sodium hydrogen carbonate (2×300 mL). The combined aqueous layers were extracted with ethyl acetate (500 mL). The combined organic extracts were dried over magnesium sulphate, filtered, and evaporated under reduced pressure to give a solid. This solid was triturated with tert-butyl methyl ether to give the title compound as a solid (53.41 g, 78%). $^1$H NMR (400 MHz, CDCl$_3$): δ 0.35 (m, 2H), 0.85 (m, 2H), 1.45 (d, 6H), 1.60 (m, 1H), 3.60 (m, 2H), 4.35 (m, 1H), 7.65 (d, 2H), 8.00 (d, 2H).

Preparation 3: 4-(4-Cyclopropyl-5-iodo-1-isopropyl-1H-pyrazol-3-yl)benzonitrile

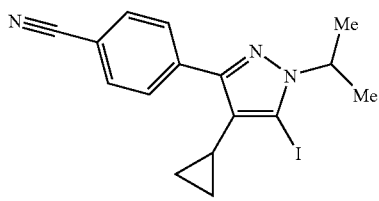

Acetic acid (6.45 mL, 113 mmol) was added to a cooled (0° C.) solution of the compound described in Preparation 2 (10 g, 37.5 mmol) in acetonitrile (150 mL). This cooled solution was allowed to stir for 15 minutes after which time a solution of potassium iodide (15.6 g, 93.9 mmol) in water (50 mL) was added followed by a solution of tert-$^t$butyl nitrite (11.2 mL, 93.9 mmol) in acetonitrile (50 mL). This mixture was stirred at 0° C. for 10 minutes, then warmed to room temperature and allowed to stir for 2.5 hours. It was quenched onto an aqueous solution of sodium metabisulphite (2 M, 300 mL), and basified with a saturated aqueous solution of sodium hydrogen carbonate. This aqueous mixture was extracted with ethyl acetate (3×100 mL), and the organic extracts were washed with brine (100 mL), dried over magnesium sulphate, filtered, and evaporated under reduced pressure to give a yellow solid. This solid was triturated with diethyl ether to give a yellow solid (11.5 g, 81%). $^1$H NMR (400 MHz, CDCl$_3$): δ 0.40 (m, 2H), 0.95 (m, 2H), 1.50 (d, 6H), 1.70 (m, 1H), 4.70 (m, 1H), 7.65 (d, 2H), 7.95 (d, 2H).

Preparation 4: Methyl 3-(4-cyanophenyl)-4-cyclopropyl-1-isopropyl-1H-pyrazole-5-carboxylate

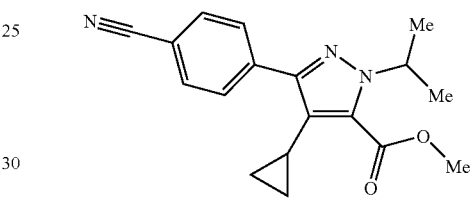

Using a procedure similar to that described for Preparation 10, but using the compound described in Preparation 3, the title compound was prepared as a solid (1.16 g, 77%). $^1$H NMR (400 MHz, CDCl$_3$): δ 0.20 (m, 2H), 0.90 (m, 2H), 1.50 (d, 6H), 1.85 (m, 1H), 3.95 (s, 3H), 5.25 (m, 1H), 7.65 (d, 2H), 7.95 (d, 2H).

Preparation 5: 3-(4-Cyanophenyl)-4-cyclopropyl-1-isopropyl-1H-pyrazole-5-carboxylic acid

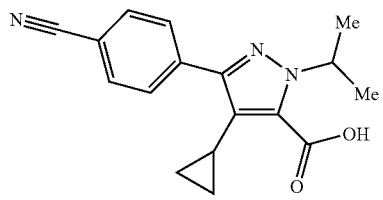

Method A

A 2.5 molar solution of n-butyl lithium (7.95 mL, 19.9 mmol) in hexane was added to a cooled (−78° C.) solution of the compound described in Preparation 3 (5 g, 13.26 mmol) in tetrahydrofuran (50 mL). This mixture was stirred at −78° C. for 1 hour, after which time carbon dioxide was bubbled through the solution for 1.5 hours. The reaction mixture was then quenched onto an aqueous solution of sodium hydroxide (2.5 M, 250 mL), and extracted with diethyl ether (2×100 mL). The combined organic extracts were back extracted with an aqueous solution of sodium hydroxide (2.5 M, 50 mL). The combined basic aqueous layers were then acidified with an aqueous solution of hydrochloric acid (2 M) and extracted with ethyl acetate (2×150 mL). The combined ethyl acetate layers were dried over magnesium sulphate, filtered, and evaporated under reduced pressure to give a yellow solid. This solid was triturated with pentane to give an off-white solid (2.45 g, 63%). $^1$H NMR (400 MHz, CDCl$_3$): δ 0.30 (m, 2H), 0.95 (m, 2H), 1.50 (d, 6H), 1.90 (m, 1H), 5.40 (m, 1H), 7.65 (d, 2H), 7.95 (d, 2H).
Method B Using a procedure similar to that described for Preparation 11, but using the compound described in Preparation 4, the title compound was prepared as a solid (0.408 g, 94%). $^1$H NMR (400 MHz, CD$_3$OD): δ 0.20 (m, 2H), 0.85 (m, 2H), 1.45 (d, 6H), 1.85 (m, 1H), 5.30 (m, 1H), 7.75 (d, 2H), 7.95 (d, 2H).

Preparation 6: Methyl 4-cyano-3-methylbenzoate

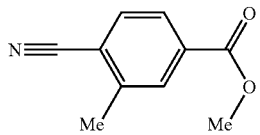

Method A 1,1'Bis(diphenylphosphino)ferrocene (8 g, 14.43 mmol) and zinc cyanide (5.08 g, 43.3 mmol), followed by tris-(dibenzylideneacetone) dipalladium (6.61 g, 7.22 mmol), were added to a solution of 4-bromo-3-methyl-benzoic acid methyl ester (16.53 g, 72 mmol) in dimethylformamide (20 mL). This mixture was stirred at reflux for 16 hours, after which time it was cooled to room temperature and concentrated under reduced pressure. Ethyl acetate (1000 mL) was added to the crude mixture and the resultant suspension was filtered. The filtrate was washed with water (1000 mL) and the aqueous layer was extracted with ethyl acetate (2×1000 mL). The combined organic extracts were washed brine (1000 mL), dried over magnesium sulphate, filtered, and evaporated under reduced pressure. The resulting material was purified by column chromatography eluting with 5% ethyl acetate in pentane to give the title compound as a solid (13.7 g, 88%). $^1$H NMR (400 MHz, CDCl$_3$): δ 2.60 (s, 3H), 3.95 (s, 3H), 7.65 (d, 1H), 7.95 (m, 1H), 8.00 (d, 1 H).
Method B Potassium Ferrocyanide trihydrate (3.70 g, 17.5 mmol) was added to a solution of 4-bromo-3-methyl-benzoic acid methyl ester (4.00 g, 17.46 mmol) in dimethylacetamide (10 mL), followed by sodium carbonate (1.85 g, 17.5 mmol) and palladium acetate (78 mg, 0.35 mmol). This mixture was heated at 120° C. for 15 hours, after which time it was quenched onto water (150 mL) and extracted with tert-butylmethylether (3×50 mL). The combined organic extracts were washed with water (150 mL), dried over magnesium sulphate, filtered and evaporated under reduced pressure to give a solid (2.53 g, 83%). $^1$H NMR (400 MHz, CDCl$_3$): δ 2.60 (s, 3H), 3.95 (s, 3H), 7.65 (d, 1H), 7.95 (m, 1H), 8.00 (d, 1 H).

Preparation 7: 4-(2-Cyanopropanoyl)-2-methylbenzonitrile

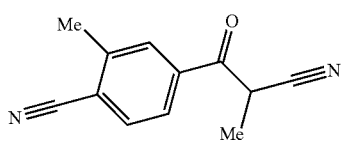

A solution of propionitrile (97 μL, 1.37 mmol) in tetrahydrofuran (5 mL) was added to sodium hydride (60% dispersion in mineral oil) (55 mg, 1.37 mmol). This mixture was stirred at 60° C. for 30 minutes, then a solution of the compound described in Preparation 6 (200 mg, 1.10 mmol) in tetrahydrofuran (5 mL) was added. This mixture was stirred at 60° C. for 16 hours and then concentrated under reduced pressure. The crude residue was quenched onto an aqueous 10% solution (weight/volume) citric acid (10 mL) and extracted with ethyl acetate (3×10 mL). The combined organic extracts were washed with an aqueous saturated solution of sodium hydrogen carbonate (3×10 mL), dried over magnesium sulphate, filtered, and evaporated under reduced pressure. This crude material was purified by column chromatography eluting with 20% ethyl acetate in heptane to give the title compound as a solid (60 mg, 27%). $^1$H NMR (400 MHz, CDCl$_3$): δ 1.65 (d, 3H), 2.65 (m, 3H), 4.35 (m, 1H), 7.75 (d, 1H), 7.85 (m, 1H), 7.95 (d, 1H).

Preparation 8: 4-(5-Amino-1-isopropyl-4-methyl-1H-pyrazol-3-yl)-2-methylbenzonitrile

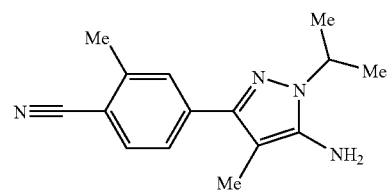

Using a procedure similar to that described for Preparation 2, but using the compound described in Preparation 7, the title compound was prepared as a solid (458 mg, 89%). $^1$H-NMR (400 MHz, CDCl$_3$): δ 1.49 (d, 6H), 2.05 (s, 3H), 2.58 (s, 3H), 3.22 (s, 2H), 4.45 (m, 1H), 7.55 (d, 1H), 7.59 (m, 1H), 7.65 (d, 1H).

Preparation 9: 4-(5-Iodo-1-isopropyl-4-methyl-1H-pyrazol-3-yl)-2-methylbenzonitrile

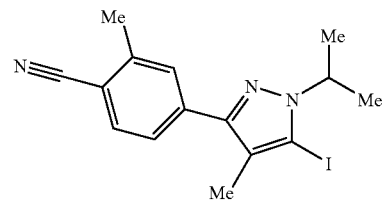

Isoamyl nitrite (21.4 mL, 160 mmol) was added to a solution of the compound described in Preparation 8 (10.19 g, 40 mmol) in diiodomethane (110 mL). This mixture was stirred at 50° C. for 1 hour. The reaction mixture was evaporated under reduced pressure to give a red solid. This solid was triturated with methanol to give an orange solid (7.8 g, 53%).

¹H-NMR (400 MHz, CDCl₃): δ 1.50 (d, 6H), 2.20 (s, 3H), 2.60 (s, 3H), 4.70 (m, 1H), 7.55 (m, 1H), 7.65 (d, 2H).

Preparation 10: Methyl 3-(4-cyano-3-methylphenyl)-1-isopropyl-4-methyl-1H-pyrazole-5-carboxylate

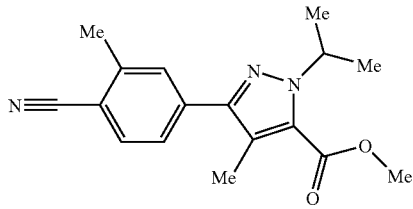

1,1'-Bis(diphenylphospino)ferrocene dichloropalladium (II) complex with dichloromethane (1:1) (1.05 g, 1.28 mmol) and triethylamine (1.43 mL, 10.2 mmol) was added to a solution of the compound described in Preparation 9 (3.12 g, 8.54 mmol), in methanol (150 mL), in a pressure reactor. This mixture was pressurised to 100 pounds per square inch with carbon monoxide, and heated at 100° C. for 8 hours. It was then filtered through Arbocel®. The filtrate was evaporated under reduced pressure to give a brown solid, which was purified by column chromatography eluting with 10% ethyl acetate in heptane to give the title compound as a yellow solid (2.31 g, 91%). ¹H NMR (400 MHz, CDCl₃): δ 1.50 (d, 6H), 2.40 (s, 3H), 2.60 (s, 3H), 3.95 (s, 3H), 5.45 (m, 1H), 7.50 (m, 1H), 7.60 (d, 1H), 7.65 (m, 1 H).

Preparation 11: 3-(4-Cyano-3-methylphenyl)-1-isopropyl-4-methyl-1H-pyrazole-5-carboxylic acid

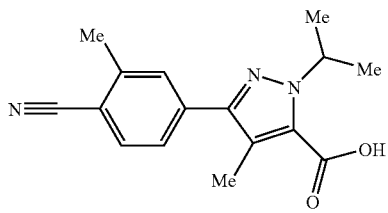

Sodium hydroxide (0.46 g, 11.7 mmol) was added to a solution of the compound described in Preparation 10 (2.31 g, 7.77 mmol) in methanol (50 mL) and water (2.8 mL). This mixture was heated to reflux for 16 hours, then cooled and evaporated under reduced pressure. The residue was diluted with water (100 mL) and acidified with an aqueous solution of hydrochloric acid (2 M). This aqueous mixture was extracted with ethyl acetate (2×200 mL) and the combined organic extracts were washed with brine (400 mL), dried over magnesium sulphate, filtered, and evaporated under reduced pressure to give a yellow solid (2.2 g 100%). ¹H NMR (400 MHz, CDCl₃): δ 1.55 (d, 6H), 2.45 (s, 3H), 2.60 (s, 3H), 5.50 (m, 1H), 7.55 (m, 1H), 7.60 (d, 1H), 7.65 (m, 1 H).

Preparation 12: 4-(2-Cyanopropanoyl)benzonitrile

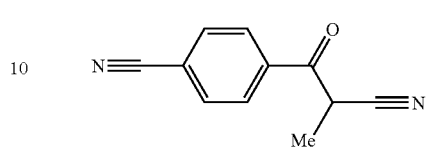

Potassium-tert-butoxide (7.76 g, 69.2 mmol) and propionitrile (4.84 mL, 69.2 mmol) was added to a solution of 4-cyano-benzoic acid methyl ester (11.15 g, 69.2 mmol) in tetrahydrofuran (100 mL). This mixture was stirred at room temperature for 16 hours, and then quenched onto an aqueous 10% solution (weight/volume) citric acid (100 mL). The organic layer was separated and the aqueous layer was extracted with ethyl acetate (3×100 mL). The combined organic extracts were dried over magnesium sulphate, filtered, and evaporated under reduced pressure. This crude residue was triturated with tert-butyl methyl ether to give the title compound as a solid (7.00 g, 55%). ¹H NMR (400 MHz, CDCl₃): δ 1.65 (d, 3H), 4.35 (m, 1H), 7.85 (d, 2H), 8.10 (d, 2H).

Preparation 13: 4-(5-Amino-1-cyclobutyl-4-methyl-1H-pyrazol-3-yl)benzonitrile

Using a procedure similar to that described for Preparation 2, but using the compound described in Preparation 12, and cyclobutyl-hydrazine hydrochloride, the title compound was prepared as a gum (110 mg, 27%). ¹H NMR (400 MHz, CDCl₃): δ 1.85 (m, 2H), 2.05 (s, 3H), 2.40 (m, 2H), 2.65 (m, 2H), 3.25 (m, 2H), 4.65 (m, 1H), 7.65 (d, 2H), 7.75 (d, 2H).

Preparation 14: 4-(1-Cyclobutyl-5-iodo-4-methyl-1H-pyrazol-3-yl)benzonitrile

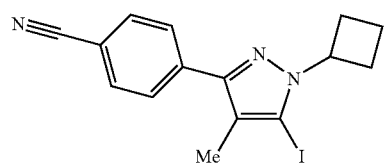

Using a procedure similar to that described for Preparation 9, but using the compound described in Preparation 13, the title compound was prepared as a solid (7.38 g, 58%). ¹H NMR (400 MHz, CDCl₃): δ 1.85 (m, 2H), 2.20 (s, 3H), 2.45 (m, 2H), 2.70 (m, 2H), 4.90 (m, 1H), 7.70 (d, 2H), 7.85 (d, 2H).

Preparation 15: Methyl 3-(4-cyanophenyl)-1-cyclobutyl-4-methyl-1H-pyrazole-5-carboxylate

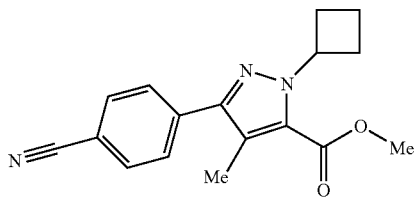

Using a procedure similar to that described for Preparation 10, but using the compound described in Preparation 14, the title compound was prepared as a solid (1.75 g, 62%). ¹H NMR (400 MHz, CDCl₃): δ 1.85 (m, 2H), 2.35 (s, 3H), 2.45 (m, 2H), 2.70 (m, 2H), 3.95 (s, 3H), 5.55 (m, 1H), 7.70 (d, 2H), 7.80 (d, 2H).

Preparation 16: 3-(4-cyanophenyl)-1-cyclobutyl-4-methyl-1H-pyrazole-5-carboxylic acid

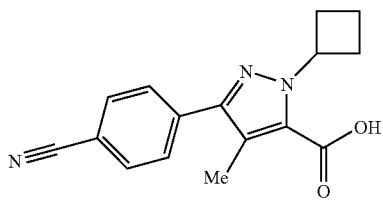

Using a procedure similar to that described for Preparation 11, but using the compound described in Preparation 15, the title compound was prepared as a solid (0.54 g, 32%). ¹H NMR (400 MHz, CDCl₃): δ 1.85 (m, 2H), 2.45 (m, 5H), 2.75 (m, 2H), 5.60 (m, 1H), 7.70 (d, 2H), 7.80 (d, 2H).

Preparation 17: tert-Butyl (2E)-2-(dihydrofuran-3(2H)-ylidene)hydrazinecarboxylate

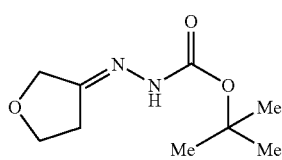

A solution of hydrazinecarboxylic acid tert-butyl ester (8.85 g, 67 mmol) in ethanol (30 mL) was added to a solution of dihydro-furan-3-one (5.78 g, 67 mmol) in ethanol (100 mL). This mixture was heated at reflux for 19 hours, then cooled to room temperature and concentrated under reduced pressure. The resulting crude mixture was partitioned between water (100 mL) and dichloromethane (100 mL). The aqueous layer was basified and extracted with dichloromethane (50 mL). The combined organic extracts were dried over magnesium sulphate, filtered, and evaporated under reduced pressure to give an oil (10.56 g, 79%). APCI MS m/z 201 [MH]⁺

Preparation 18: (+/−)-tert-Butyl 2-(tetrahydrofuran-3-yl)hydrazinecarboxylate

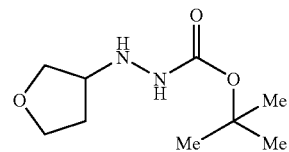

Sodium cyanoborohydride (10 g, 160 mmol) was added to a mixture of the compound described in Preparation 17 (10.56 g, 53 mmol) and acetic acid (150 mL). This mixture was stirred at room temperature for 16 hours and then neutralised with aqueous sodium hydroxide (1 M), before being extracted with dichloromethane (3×100 mL). The combined organic extracts were washed with an aqueous saturated solution of sodium hydrogen carbonate (100 mL), dried over magnesium sulphate, filtered, and evaporated under reduced pressure to give a solid (8.14 g, 76%). APCI MS m/z 203 [MH]⁺

Preparation 19: (+/−)-Tetrahydrofuran-3-ylhydrazine hydrochloride

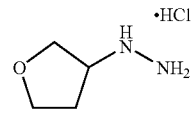

The compound described in Preparation 18 (8.14 g, 40 mmol) was stirred in a solution of hydrogen chloride in 1,4-dioxane (4 M, 60 mL), at room temperature for 16 hours. A solution of hydrogen chloride in 1,4-dioxane (4 M, 20 mL) was then added and the mixture was stirred at room temperature for a further 64 hours, After which time it was evaporated under reduced pressure to give a solid (5.60 g, 100%). APCI MS m/z 103 [MH]⁺

Preparation 20: (+/−)-4-[5-Amino-4-methyl-1-(tetrahydrofuran-3-yl)-1H-pyrazol-3-yl]benzonitrile

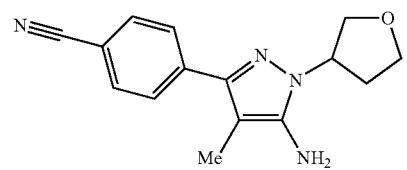

Using a procedure similar to that described for Preparation 2, but using the compound described in Preparation 12, and the compound described in Preparation 19, the title compound was prepared as a white solid (9.00 g, 70%). ¹H NMR (400 MHz, CDCl₃): δ 2.05 (s, 3H), 2.45 (m, 2H), 3.75 (m, 2H), 3.85 (m, 1H), 4.00 (m, 1H), 4.15 (m, 1H), 4.25 (m, 1H), 5.05 (m, 1H), 7.65 (d, 2H), 7.75 (d, 2H).

Preparation 21: (+/−)-4-[5-Iodo-4-methyl-1-(tetrahydrofuran-3-yl)-1H-pyrazol-3-yl]benzonitrile

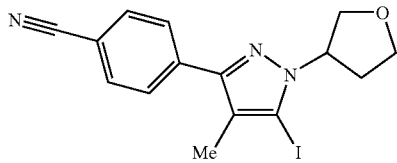

Using a procedure similar to that described for Preparation 9, but using the compound described in Preparation 20, the title compound was prepared as a solid (7.78 g, 68%). ESCI MS m/z 380 [MH]⁺

Preparation 22: (+/−)-Methyl 3-(4-cyanophenyl)-4-methyl-1-(tetrahydrofuran-3-yl)-1H-pyrazole-5-carboxylate

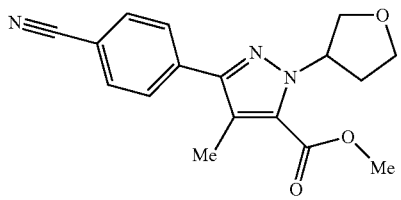

Using a procedure similar to that described for Preparation 10, but using the compound described in Preparation 21, the title compound was prepared as a solid (4.16 g, 93%). $^1$H NMR (400 MHz, CDCl$_3$): δ 2.40 (m, 4H), 2.60 (m, 1H), 3.95 (s, 3H), 4.00 (m, 2H), 4.20 (m, 2H), 5.80 (m, 1H), 7.70 (d, 2H), 7.75 (d, 2H).

Preparation 23: (+/−)-3-(4-Cyanophenyl)-4-methyl-1-(tetrahydrofuran-3-yl)-1H-pyrazole-5-carboxylic acid

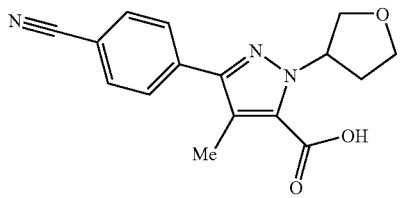

Using a procedure similar to that described for Preparation 11, but using the compound described in Preparation 22, the title compound was prepared as a solid (1.29 g, 37%). $^1$H NMR (400 MHz, CDCl$_3$): δ 2.40 (m, 2H), 2.45 (s, 3H), 2.65 (m, 1H), 4.05 (m, 2H), 4.20 (m, 2H), 5.85 (m, 1H), 7.70 (d, 2H), 7.75 (d, 2H).

Preparation 24: Di-tert-butyl-1-cyclopropylhydrazine-1,2-dicarboxylate

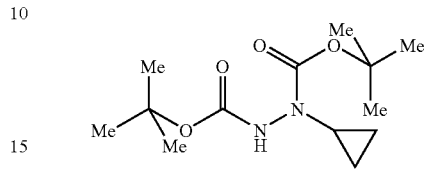

A solution of di-tert-butyl azodicarboxylate (115 g, 500 mmol) in tetrahydrofuran (1000 mL) was added to a cooled (−78° C.) solution of cyclopropylmagnesium bromide (2 M, 1000 mL, 500 mmol) in tetrahydrofuran. The reaction mixture was stirred at −78° C. for 10 minutes, After which time it was quenched onto acetic acid (30 mL) and allowed to warm to room temperature. This mixture was partitioned between water (2000 mL) and ethyl acetate (1500 mL). The organic extract was dried over sodium sulphate, filtered, and evaporated under reduced pressure to give a solid, which was purified by column chromatography eluting with 3.33% ethyl acetate in pentane to give the title compound as a white solid (45 g, 33%). $^1$H-NMR (400 MHz, CDCl$_3$): δ 0.65 (m, 4H), 1.30-1.50 (m, 18H), 2.70 (m, 1H).

Preparation 25: Cyclopropylhydrazine Hydrochloride

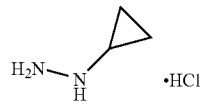

Using a procedure similar to that described for Preparation 19, but using the compound described in Preparation 24, the title compound was prepared as a white solid (35 g, 73%). $^1$H-NMR (400 MHz, (CD$_3$)$_2$SO): δ 0.50 (m, 4H), 2.55 (m, 1H).

Preparation 26: 4-(5-Amino-1-cyclopropyl-4-methyl-1H-pyrazol-3-yl)-benzonitrile

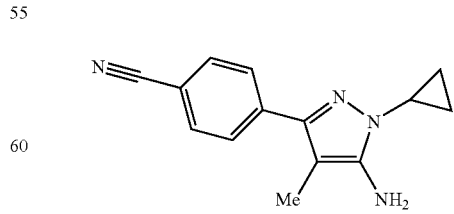

Using a procedure similar to that described for Preparation 2, but using the compounds obtained from Preparation 12, and Preparation 25, the title compound was prepared as a solid (1.24 g, 71%). ¹H-NMR (400 MHz, CDCl₃): δ 1.05 (m, 2H), 1.20 (m, 2H), 2.05 (s, 3H), 3.25 (m, 1H), 3.75 (m, 2H), 7.65 (d, 2H), 7.75 (d, 2H).

Preparation 27: 4-(1-Cyclopropyl-5-iodo-4-methyl-1H-pyrazol-3-yl)-benzonitrile

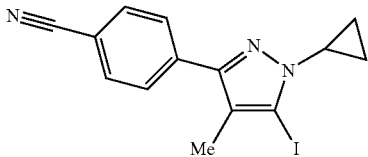

Using a procedure similar to that described for Preparation 9, but using the compound described in Preparation 26, the title compound was prepared as a solid (4.9 g, 54%). ¹H-NMR (400 MHz, CDCl₃): δ 1.05 (m, 2H), 1.15 (m, 2H), 2.20 (s, 3H), 3.45 (m, 1H), 7.65 (d, 2H), 7.75 (d, 2H).

Preparation 28: Methyl 3-(4-cyanophenyl)-1-cyclopropyl-4-methyl-1H-pyrazole-5-carboxylate

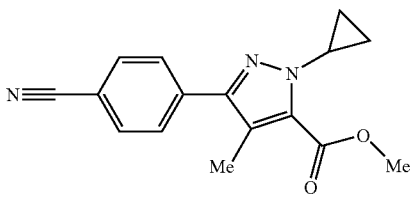

Using a procedure similar to that described for Preparation 10, but using the compound described in Preparation 27, the title compound was prepared as a solid (1.39 g, 85%). ¹H-NMR (400 MHz, CDCl₃): δ 1.05 (m, 2H), 1.15 (m, 2H), 2.40 (s, 3H), 3.95 (s, 3H), 4.25 (m, 1H), 7.70 (m, 4H).

Preparation 29: 3-(4-Cyanophenyl)-1-cyclopropyl-4-methyl-1H-pyrazole-5-carboxylic acid

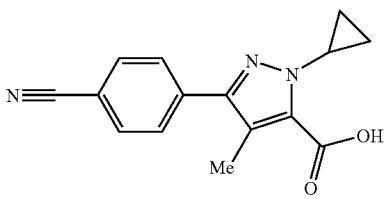

Using a procedure similar to that described for Preparation 11, but using the compound described in Preparation 28, the title compound was prepared as a solid (76 mg, 80%). ¹H-NMR (400 MHz, CDCl₃): δ 1.10 (m, 2H), 1.15 (m, 2H), 2.45 (s, 3H), 4.30 (m, 1H), 7.75 (m, 4H).

Preparation 30: 4-(Cyanoacetyl)benzonitrile

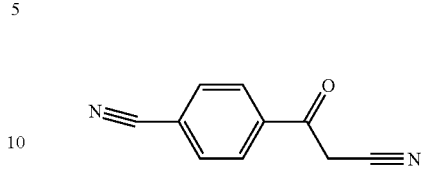

A solution of acetonitrile (9.22 mL, 176 mmol) in tetrahydrofuran (320 mL) was added to sodium hydride (60% dispersion in mineral oil) (11.80 g, 294 mmol). This mixture was stirred at room temperature for 15 minutes, and then 4-Cyano-benzoic acid methyl ester (23.70 g, 147 mmol) was added. The reaction mixture was stirred at 60° C. for 2 hours, And then quenched onto an aqueous solution of hydrochloric acid (2M, 500 mL), and extracted with ethyl acetate (3×500 mL). The combined organic extracts were washed with brine (500 mL), dried over magnesium sulphate, filtered and evaporated under reduced pressure. This residue was triturated with 20% ethyl acetate in heptane to give the title compound as a solid (23.17 g, 93%). ESCI MS m/z 169 [M−H]⁻

Preparation 31: 4-(5-Amino-1-isopropyl-1H-pyrazol-3-yl)benzonitrile

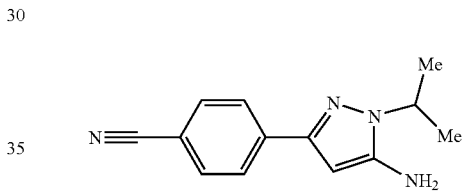

Using a procedure similar to that described for Preparation 2, but using the compound described in Preparation 30, the title compound was prepared as a solid (4.40 g, 78%). ¹H-NMR (400 MHz, CDCl₃): δ 1.50 (d, 6H), 4.40 (m, 1H), 5.90 (s, 1H), 7.60 (d, 2H), 7.80 (d, 2H).

Preparation 32: 4-(5-Amino-4-iodo-1-isopropyl-1H-pyrazol-3-yl)benzonitrile

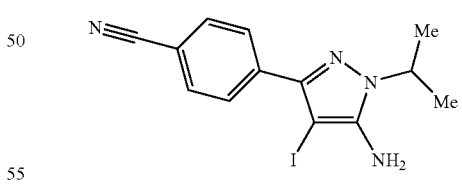

N-Iodosuccinimide (1.73 g, 7.69 mmol) was added to a solution of the compound described in Preparation 31 (1.45 g, 6.41 mmol) in acetonitrile (25.6 mL). This mixture was refluxed for 4 hours and then allowed to stand at room temperature for 16 hours. It was then concentrated under reduced pressure and the crude residue was partitioned between water (50 mL) and ethyl acetate (3×50 mL). The combined organic extracts were dried over magnesium sulphate, filtered, and evaporated under reduced pressure to give a solid. This crude mixture was purified by column chromatography eluting with 30% ethyl acetate in pentane to give the title compound as a solid (1.91 g, 85%). ¹H-NMR (400 MHz, CD₃OD): δ 1.40 (d, 6H), 4.55 (m, 1H), 7.75 (d, 2H), 8.00 (d, 2H).

Preparation 33: 5-Amino-3-(4-cyanophenyl)-1-isopropyl-1H-pyrazole-4-carbonitrile

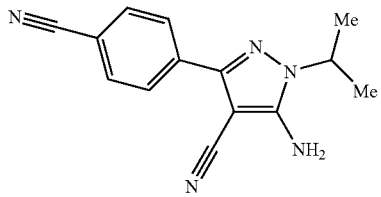

Using a procedure similar to Preparation 6, but using the compound described in to Preparation 32, the title compound was prepared as a solid (920 mg, 86%). ¹H-NMR (400 MHz, CDCl₃): δ 1.50 (d, 6H), 4.25 (m, 1H), 4.35 (m, 2H), 7.70 (d, 2H), 8.05 (d, 2H).

Preparation 34: 3-(4-Cyanophenyl)-5-iodo-1-isopropyl-1H-pyrazole-4-carbonitrile

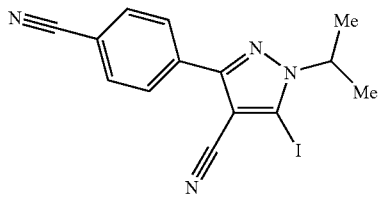

Using a procedure similar to that described for Preparation 9, but using the compound described in Preparation 33, the title compound was prepared as a solid (6.1 g, 85%). ¹H-NMR (400 MHz, CDCl₃): δ 1.55 (d, 6H), 4.75 (m, 1H), 7.75 (d, 2H), 8.10 (d, 2H).

Preparation 35: Methyl 4-cyano-3-(4-cyanophenyl)-1-isopropyl-1H-pyrazole-5-carboxylate

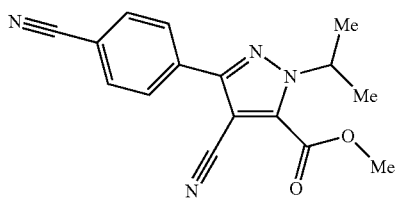

Using a procedure similar to that described for Preparation 10, but using the compound described in Preparation 34, the title compound was prepared as a solid (1.55 g, 29%). ¹H-NMR (400 MHz, CDCl₃): δ 1.55 (d, 6H), 4.05 (s, 3H), 5.60 (m, 1H), 7.75 (d, 2H), 8.15 (d, 2H).

Preparation 36: 4-Cyano-3-(4-cyanophenyl)-1-isopropyl-1H-pyrazole-5-carboxylic acid

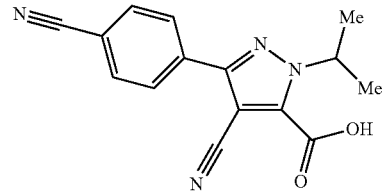

Using a procedure similar to that described for Preparation 11, but using the compound described in Preparation 35, the title compound was prepared as a solid (0.89 g, 62%). ¹H-NMR (400 MHz, CDCl₃): δ 1.50 (d, 6H), 5.60 (m, 1H), 7.75 (d, 2H), 8.15 (d, 2H).

Preparation 37: 4-(2-Cyano-3-phenylpropanoyl)benzonitrile

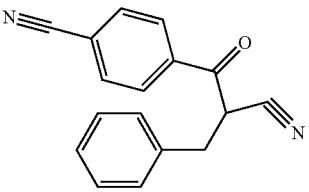

Using a procedure similar to that described for Preparation 1, but using 3-phenylpropionitrile, the title compound was prepared as an oil (2.43 g, 30%). ¹H-NMR (400 MHz, CDCl₃): δ 3.25 (m, 1 H), 3.35 (m, 1 H), 4.45 (m, 1H), 7.30 (m, 5H), 7.80 (d, 2H), 8.00 (d, 1H).

Preparation 38: 4-(5-Amino-4-benzyl-1-isopropyl-1H-pyrazol-3-yl)benzonitrile

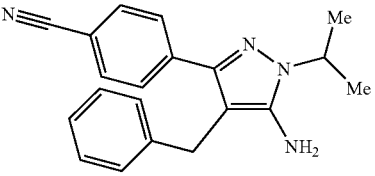

Using a procedure similar to that described for Preparation 2, but using the compound described in Preparation 37, the title compound was prepared as a solid (1.55 g, 53%).

¹H-NMR (400 MHz, CDCl₃): δ 1.55 (d, 6H), 3.20 (m, 2H), 3.90 (s, 2H), 4.45 (m, 1H), 7.10-7.40 (m, 5H), 7.55 (d, 2H), 7.65 (d, 2H).

Preparation 39: 4-(4-Benzyl-5-iodo-1-isopropyl-1H-pyrazol-3-yl)benzonitrile

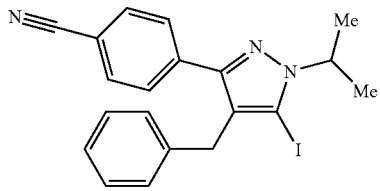

Using a procedure similar to that described for Preparation 9, but using the compound described in Preparation 38, the title compound was prepared as a solid (1.18 g, 62%). ¹H-NMR (400 MHz, CDCl₃): δ 1.55 (d, 6H), 4.00 (s, 2H), 4.80 (m, 1H), 7.05 (m, 2H), 7.20 (m, 1H), 7.25 (m, 2H), 7.55 (d, 2H), 7.65 (d, 2H).

Preparation 40: Methyl 4-benzyl-3-(4-cyanophenyl)-1-isopropyl-1H-pyrazole-5-carboxylate

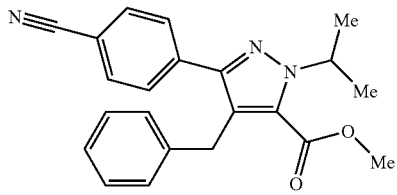

Using a procedure similar to that described for Preparation 10, but using the compound described in Preparation 39, the title compound was prepared as a solid (0.7 g, 70%). ¹H-NMR (400 MHz, CDCl₃): δ 1.55 (d, 6H), 3.75 (s, 3H), 4.20 (s, 2H), 5.45 (m, 1H), 7.05 (m, 2H), 7.15 (m, 1H), 7.25 (m, 2H), 7.60 (m, 4H).

Preparation 41: 4-Benzyl-3-(4-cyanophenyl)-1-isopropyl-1H-pyrazole-5-carboxylic acid

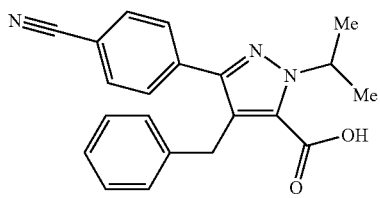

Using a procedure similar to that described for Preparation 11, but using the compound described in Preparation 40, the title compound was prepared as a solid (0.63 g, 94%). ¹H-NMR (400 MHz, CD₃OD): δ 1.55 (d, 6H), 4.25 (s, 2H), 5.55 (m, 1H), 7.00 (m, 2H), 7.10 (m, 1H), 7.20 (m, 2H), 7.65 (m, 4H).

Preparation 42: (3,3-Difluorocyclobutane)carboxylic acid ethyl ester

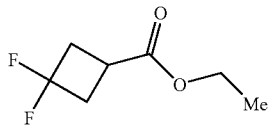

(Diethylamino)sulphur trifluoride (4 mL, 29.5 mmol) was added to a cooled (−4° C.) solution of 3-oxo-cyclobutanecarboxylic acid ethyl ester (2.80 g, 15 mmol) (prepared according to Tetrahedron Letters (1967), (47), 4729-31) in dichloromethane (100 mL). This mixture was allowed to warm to room temperature and then stirred for 88 hours, After which time it was quenched onto a mixture of sodium carbonate and ice, and allowed to stir for 10 minutes. This mixture was then extracted with dichloromethane (3×75 mL) and the combined organic extracts were dried over sodium sulphate, filtered, and evaporated under reduced pressure to give an oil. This crude residue was purified by column chromatography eluting with dichloromethane to give the title compound as a yellow oil (2.30 g, 95%). ¹H-NMR (400 MHz, CDCl₃): δ 1.25 (t, 3H), 2.60-3.00 (m, 4H), 4.15 (q, 2H).

Preparation 43: (3,3-Difluoro-cyclobutyl)methanol

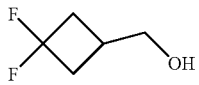

A solution of the compound described in Preparation 42 (2.30 g, 14 mmol), in diethyl ether (14 mL), was added to a suspension of lithium aluminium hydride (1.17 g, 30.8 mmol), in diethyl ether (70 mL), cooled to −45° C. This mixture was stirred at −45° C. for 1 hour, then warmed to −10° C. for 1 hour. It was then slowly warmed to room temperature and stirred for 15 hours, After which time it was cooled to 4° C. and quenched with sequential addition of water (1.2 mL), 10% aqueous solution of sodium hydroxide (1.2 mL) and finally water (3.6 mL). Diethyl ether (50 mL) was then added and the solution was allowed to stir for 90 minutes. The organic layer was separated and the aqueous phase was back extracted with diethyl ether (3×50 mL). The combined organic layers were dried over magnesium sulphate, filtered, and concentrated under reduced pressure to give a 45% solution of the title compound in diethyl ether (1.56 g, 92%).

¹H-NMR (400 MHz, CDCl₃): δ 2.30 (m, 3H), 2.60 (m, 2H), 3.65 (m, 2H).

Preparation 44: Toluene-4-sulfonic acid (3,3-difluorocyclobutyl)methyl ester

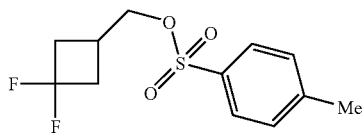

p-Toluenesulphonyl chloride (19.4 g, 102 mmol) was added to a solution of the compound described in Preparation 43 (4.29 g, 35.2 mmol) in pyridine (50 mL), and stirred at room temperature for 16 hours. The mixture was then partitioned between brine (50 mL) and diethyl ether (2×50 mL). The combined organic extracts were washed with brine (50 mL), dried over magnesium sulphate, filtered and evaporated under reduced pressure to give gum. This crude residue was purified by column chromatography eluting with 5% ethyl acetate in pentane to give the title compound as a white solid (4.31 g, 44%). ¹H-NMR (400 MHz, CDCl₃): δ 2.25 (m, 2H), 2.45 (m, 4H), 2.65 (m, 2H), 4.05 (d, 2H), 7.35 (d, 2H), 7.80 (d, 2H).

Preparation 45: (3,3-Difluorocyclobutyl)acetonitrile

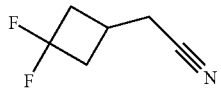

Sodium cyanide (1.91 g, 38.9 mmol) was added to a solution of the compound described in Preparation 44 (4.30 g, 15.56 mmol) in dimethyl sulphoxide (20 mL). This mixture was stirred at room temperature for 3 hours, and after this time it was heated to 80° C. for 2 hours. It was then cooled to room temperature and partitioned between brine (50 mL) and diethyl ether (2×50 mL). The combined organic extracts were washed with brine (50 mL), dried over magnesium sulphate, filtered and evaporated under reduced pressure to an oil (1.72 g, 84%). ¹H-NMR (400 MHz, CDCl₃): δ 2.40 (m, 2H), 2.55 (m, 3H), 2.85 (m, 2H).

Preparation 46: 4-[Cyano(3,3-difluorocyclobutyl)acetyl]benzonitrile

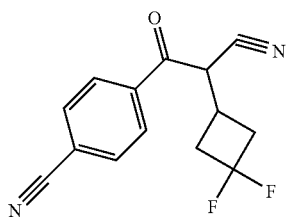

Using a procedure similar to that described for Preparation 1, but using the compound described in Preparation 45, the title compound was prepared as a solid (1.89 g, 55%). ¹H-NMR (400 MHz, CDCl₃): δ 2.40 (m, 1H), 2.65 (m, 1H), 2.90 (m, 3H), 4.40 (d, 1H), 7.85 (d, 2H), 8.10 (d, 2H).

Preparation 47: 4-[5-Amino-4-(3,3-difluorocyclobutyl)-1-isopropyl-1H-pyrazol-3-yl]benzonitrile

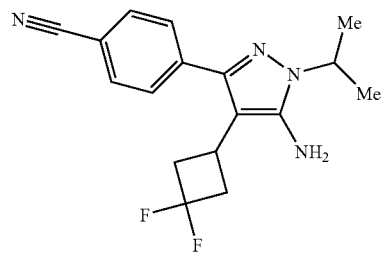

Using a procedure similar to that described for Preparation 2, but using the compound described in Preparation 46, the title compound was prepared as a solid (1.53 g, 67%). ¹H-NMR (400 MHz, CDCl₃): δ 1.55 (d, 6H), 2.65 (m, 2H), 2.95 (m, 2H), 3.40 (m, 3H), 4.40 (m, 1H), 7.55 (d, 2 H), 7.65 (d, 2 H).

Preparation 48: 4-[4-(3,3-Difluorocyclobutyl)-5-iodo-1-isopropyl-1H-pyrazol-3-yl]benzonitrile

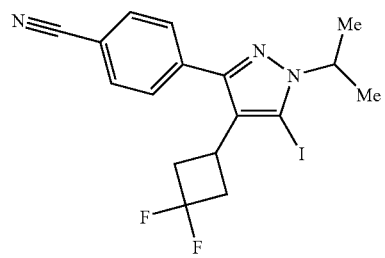

Using a procedure similar to that described for Preparation 8, but using the compound described in Preparation 47, the title compound was prepared as a solid (0.70 g, 39%). ¹H-NMR (400 MHz, CDCl₃): δ 1.55 (d, 6H), 2.60-3.00 (m, 4H), 3.40 (m, 1H), 4.75 (m, 1H), 7.55 (d, 2H), 7.70 (d, 1H).

Preparation 49: Methyl 3-(4-cyanophenyl)-4-(3,3-difluorocyclobutyl)-1-isopropyl-1H-pyrazole-5-carboxylate

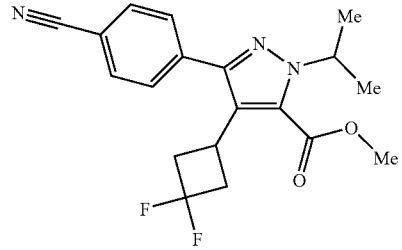

Using a procedure similar to that described for Preparation 10, but using the compound described in Preparation 48, the title compound was prepared as a solid (0.30 g, 50%). LCMS R$_t$=1.79 mins ESCI MS m/z 360 [M−H]$^+$

Preparation 50: 3-(4-Cyanophenyl)-4-(3,3-difluorocyclobutyl)-1-isopropyl-1H-pyrazole-5-carboxylic acid

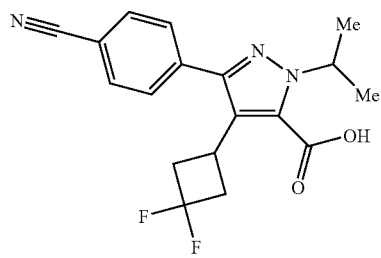

Using a procedure similar to that described for Preparation 11, but using the compound described in Preparation 49, the title compound was prepared as a solid (0.25 g, 88%). $^1$H-NMR (400 MHz, CD$_3$OD): δ 1.50 (d, 6H), 2.60 (m, 2H), 2.80 (m, 2H), 3.60 (m, 1H), 5.40 (m, 1H), 7.60 (d, 2H), 7.80 (m, 2H).

Preparation 51: 4-(2-Cyanobutanoyl)benzonitrile

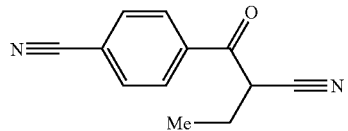

Using a procedure similar to that described for Preparation 1, but using butyronitrile, the title compound was prepared as a gum (800 mg, 65%). ESCI MS m/z 197 [M−H]$^−$.

Preparation 52: 4-(5-Amino-4-ethyl-1-isopropyl-1H-pyrazol-3-yl)benzonitrile

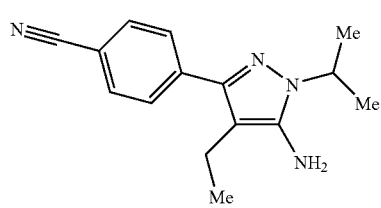

Using a procedure similar to that described for Preparation 2, but using the compound described in Preparation 51, the title compound was prepared as a white solid (691 mg, 64%). $^1$H-NMR (400 MHz, CDCl$_3$): δ 1.15 (t, 3H), 1.50 (d, 6H), 2.50 (q, 2H), 3.35 (m, 2H), 4.45 (m, 1H), 7.65 (d, 2H), 7.75 (d, 2H).

Preparation 53: 4-(4-Ethyl-5-iodo-1-isopropyl-1H-pyrazol-3-yl)benzonitrile

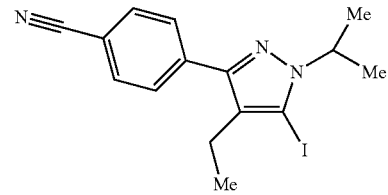

Using a procedure similar to that described for Preparation 9, but using the compound described in Preparation 52, the title compound was prepared as a solid (9.00 g, 63%). $^1$H-NMR (400 MHz, CDCl$_3$): δ 1.15 (t, 3H), 1.50 (d, 6H), 2.60 (q, 2H), 4.70 (m, 1H), 7.65 (d, 2H), 7.75 (d, 2H).

Preparation 54: Methyl 3-(4-cyanophenyl)-4-ethyl-1-isopropyl-1H-pyrazole-5-carboxylate

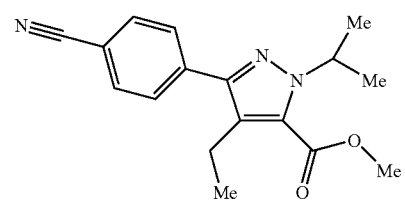

Using a procedure similar to that described for Preparation 10, but using the compound described in Preparation 53, the title compound was prepared as a solid (2.45 g, 100%). $^1$H-NMR (400 MHz, CDCl$_3$): δ 1.20 (t, 3H), 1.55 (d, 6H), 2.80 (q, 2H), 3.95 (s, 3H), 5.45 (m, 1H), 7.75 (m, 4H).

Preparation 55: 3-(4-Cyanophenyl)-4-ethyl-1-isopropyl-1H-pyrazole-5-carboxylic acid

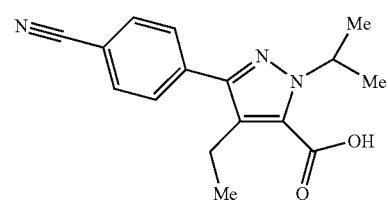

Using a procedure similar to that described for Preparation 11, but using the compound described in Preparation 54, the title compound was prepared as a solid (2.00 g, 89%).

$^1$H-NMR (400 MHz, CDCl$_3$): δ 1.25 (t, 3H), 1.55 (d, 6H), 2.90 (q, 2H), 5.50 (m, 1H), 7.75 (m, 4H).

Preparation 56: (+/−)-4-(5-Amino-1-sec-butyl-4-ethyl-1H-pyrazol-3-yl)-2-methylbenzonitrile

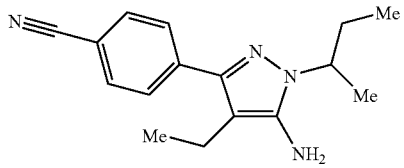

Using a procedure similar to that described for Preparation 2, but using the compound described in Preparation 51 and (+/−)-sec-butyl-hydrazine hydrochloride, the title compound was prepared as solid (630 mg, 70%). $^1$H NMR (400 MHz, CDCl$_3$): δ 0.85 (t, 3H), 1.15 (t, 3H), 1.45 (d, 3H), 1.80 (m, 1H), 2.00 (m, 1H), 2.55 (q, 2H) 3.25 (m, 2H), 4.20 (m, 1H), 7.65 (d, 2H), 7.75 (d, 2H).

Preparation 57: (+/−)-4-(1-sec-butyl-4-ethyl-5-iodo-1H-pyrazol-3-yl)benzonitrile

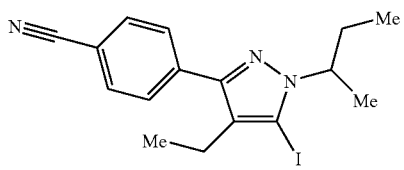

Using a procedure similar to that described for Preparation 9, but using the compound described in Preparation 56, the title compound was prepared as a solid (16.00 g, 61%). $^1$H NMR (400 MHz, CDCl$_3$): δ 0.85 (t, 3H), 1.15 (t, 3H), 1.45 (d, 3H), 1.80 (m, 1H), 2.05 (m, 1H), 2.60 (q, 2H), 4.45 (m, 1H), 7.70 (d, 2H), 7.75 (d, 2H).

Preparation 58: (+/−)-Methyl 1-sec-butyl-3-(4-cyanophenyl)-4-ethyl-1H-pyrazole-5-carboxylate

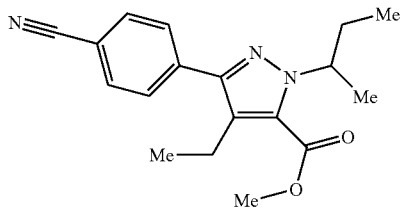

Using a procedure similar to that described for Preparation 10, but using the compound described in Preparation 57, the title compound was prepared as a solid (1.03 g, 42%). $^1$H NMR (400 MHz, CDCl$_3$): δ 0.80 (t, 3H), 1.20 (t, 3H), 1.50 (d, 3H), 1.80 (m, 1H), 2.05 (m, 1H), 2.80 (m, 2H) 3.95 (s, 3H), 5.20 (m, 1H), 7.75 (m, 4H).

Preparation 59: (+/−)-1-sec-Butyl-3-(4-cyanophenyl)-4-ethyl-1H-pyrazole-5-carboxylic acid

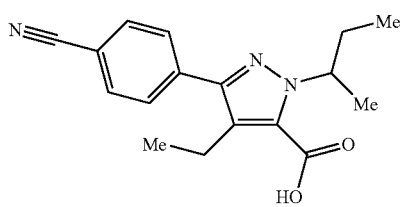

Using a procedure similar to that described for Preparation 11, but using the compound described in Preparation 58, the title compound was prepared as a solid (0.54 g, 54%). $^1$H NMR (400 MHz, CDCl$_3$): δ 0.85 (t, 3H), 1.25 (t, 3H), 1.55 (d, 3H), 1.80 (m, 1H), 2.05 (m, 1H), 2.85 (m, 2H), 5.30 (m, 1H), 7.75 (m, 4H).

Preparation 60: 4-[Cyano(cyclopropyl)acetyl]-2-methylbenzonitrile

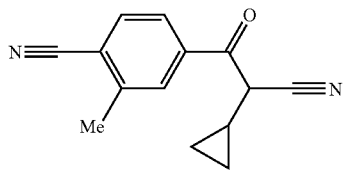

Using a procedure similar to that described for Preparation 1, but using the compound described in Preparation 6, the title compound was prepared as an oil which crystallised over time (3.39 g, 53%). APCI MS m/z 225 [MH]$^+$ Preparation 61: 4-(5-Amino-4-cyclopropyl-1-isopropyl-1H-pyrazol-3-yl)-2-methylbenzonitrile

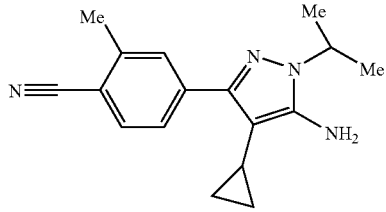

Using a procedure similar to that described for Preparation 2, but using the compound described in Preparation 60, the title compound was prepared as an oil (5.23 g, 84%). $^1$H NMR (400 MHz, CDCl$_3$): 0.35 (m, 2H), 0.85 (m, 2H), 1.45 (d, 6H), 1.60 (m, 1H), 2.55 (s, 3H), 4.35 (m, 1H), 7.60 (d, 1H), 7.70 (m, 1H), 7.85 (m, 1H).

Preparation 62: 4-(4-Cyclopropyl-5-iodo-1-isopropyl-1H-pyrazol-3-yl)-2-methyl benzonitrile

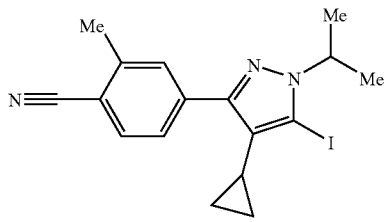

Using a procedure similar to that described for Preparation 9, but using the compound described in Preparation 61, the title compound was prepared as a solid (0.8 g, 57%). $^1$H NMR (400 MHz, CDCl$_3$): 0.35 (m, 2H), 0.95 (m, 2H), 1.50 (d, 6H), 1.65 (m, 1H), 2.60 (s, 3H), 4.70 (m, 1H), 7.60 (d, 1H), 7.75 (m, 1H), 7.80 (d, 1H).

Preparation 63: Methyl 3-(4-cyano-3-methylphenyl)-4-cyclopropyl-1-isopropyl-1H-pyrazole-5-carboxylate

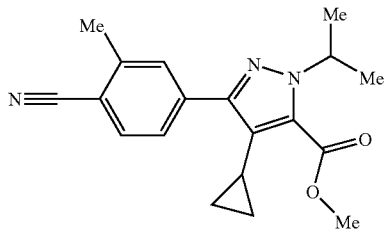

Using a procedure similar to that described for Preparation 10, but using the compound described in Preparation 62, the title compound was prepared as a solid (0.50 g, 80%). $^1$H NMR (400 MHz, CDCl$_3$): 0.20 (m, 2H), 0.90 (m, 2H), 1.50 (d, 6H), 1.85 (m, 1H), 2.60 (s, 3H), 3.95 (s, 3H), 5.30 (m, 1H), 7.65 (d, 1H), 7.70 (m, 1H), 7.75 (d, 1H).

Preparation 64: 3-(4-Cyano-3-methylphenyl)-4-cyclopropyl-1-isopropyl-1H-pyrazole-5-carboxylic Acid

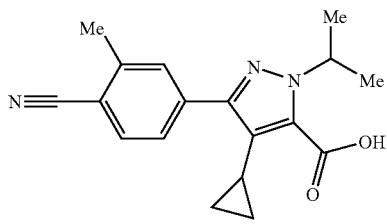

Using a procedure similar to that described for Preparation 11, but using the compound described in Preparation 63, the title compound was prepared as a solid (0.43 g, 94%). $^1$H NMR (400 MHz, CDCl$_3$): 0.30 (m, 2H), 0.95 (m, 2H), 1.55 (d, 6H), 1.95 (m, 1H), 2.60 (s, 3H), 5.45 (m, 1H), 7.65 (d, 1H), 7.70 (m, 1H), 7.75 (d, 1H).

Preparation 65: cis-3-Aminocyclobutanol hydrochloride

Using a procedure similar to that described for Preparation 19, but using (cis) tert-butyl-3-hydroxycyclobutyl carbamate (Allweys), the title compound was prepared as a solid (0.14 g, 99%). $^1$H NMR (400 MHz, CD$_3$OD): δ 2.05 (m, 3H), 2.75 (m, 2H), 3.35 (m, 1H), 4.05 (m, 1H).

Preparation 66: (S)-6,7-Dihydro-5H-pyrrolo[1,2-a]imidazol-6-ol

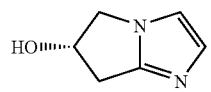

Step 1

Imidazole (93.73 g, 1.26 mol) and tert-butyldimethylsilyl chloride (145.3 g, 0.96 mol) were added to a solution of (S)-4-hydroxy-2-pyrrolidone (92.8 g, 0.92 mol) in dimethylformamide (560 mL). The mixture was then stirred at room temperature for 16 hours, after which time it was poured over ice and an aqueous solution of hydrochloric acid (0.2 M, 300 mL) was added. The mixture was stirred at room temperature for 10 minutes, and then extracted with ethyl acetate (4×500 mL). The combined organic extracts were washed with brine (1000 mL), dried over sodium sulphate, filtered, and evaporated under reduced pressure to give (S)-4-(tert-butyl-dimethyl-silanyloxy)-pyrrolidin-2-one as a solid (200 g, 100%).

Step 2

Caesium carbonate (800 g, 2.48 mol) was added to a mixture of the compound isolated in Step 1 (180 g, 0.84 mol) in dichloromethane (5400 mL).

This mixture was stirred at room temperature for 5 minutes, and then triethyloxonium tetrafluoroborate (180 g, 0.95 mol) was added. The mixture was stirred at room temperature for 16 hours, quenched with water (1500 mL), and then stirred at room temperature for 10 minutes. The organic phase was then separated and washed with water (5×1000 mL). It was dried over sodium sulphate, filtered, and evaporated under reduced pressure to give (S)-3-(tert-butyl-dimethyl-silanyloxy)-5-ethoxy-3,4-dihydro-2H-pyrrole as a liquid (202 g, 97%).

Step 3

Ethanolic hydrogen chloride (1M, 420 mL) was added dropwise to a solution of aminoacetaldehyde diethyl acetal (55.1 g, 0.14 mol) and the compound isolated in Step 2 (101 g, 0.41 mol) in ethanol (1500 mL). This mixture was stirred at room temperature for 16 hours, and then evaporated under reduced pressure. The resulting solid was recrystalised from ether to give [(S)-4-(tert-butyl-dimethyl-silanyloxy)-4,5-dihydro-3H-pyrrol-2-yl]-(2,2-diethoxy-ethyl)-amine as a solid (201 g, 78%).

Step 4

An aqueous solution of hydrochloric acid (0.625 M, 1000 mL) was added to a mixture of the compound isolated in Step 3 (207 g, 0.625 mol) in 1,4-dioxane (200 mL). The mixture was refluxed for 2 hours, and then cooled to room temperature, before washing with diethyl ether (3×300 mL). The aqueous layer was basified with sodium carbonate and extracted with dichloromethane (20×500 mL). The combined organic extracts were washed with brine (500 mL) evaporated under reduced pressure to give the title compound as a solid (55.5 gm 71%). $^1$H NMR (400 MHz, (CD$_3$)$_2$SO): δ 2.45 (m, 1H), 2.90 (m, 1H), 3.60 (m, 1H), 4.00 (m, 1H), 4.75 (m, 1H), 5.40 (m, 1H), 6.75 (m, 1H), 6.95 (m, 1H).

Preparation 67: (R)-(6,7-Dihydro-5H-pyrrolo[1,2-a]imidazol-6-yl)amine hydrochloride

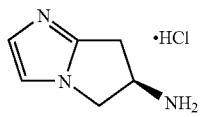

Diisopropyl azodicarboxylate (93.1 g, 461 mmol) was added to a solution of the compound described in Preparation 66 (Step 4) (48 g), 384 mmol) and triphenylphosphine (121 g, 461 mmol) in tetrahydrofuran (1800 mL), cooled to 10° C., followed by diphenylphosphoryl azide (98.8 g, 461 mmol). This mixture was stirred at room temperature for 16 hours, and then evaporated under reduced pressure. The crude residue was purified by column chromatography eluting with 33% ethyl acetate in pentane. The clean fractions were concentrated under reduced volume (150 mL), which was diluted with ethanol (1000 mL). 10% palladium on carbon was then added. The mixture was hydrogenated at 1 atmosphere. It was then filtered, and the filtrate was concentrated under reduced pressure to a reduced volume (500 mL). Ethanolic hydrogen chloride (10M, 50 mL) was added dropwise, and the solid which formed was filtered, and washed with ethanol to give the title compound as a solid (30 g, 44%). $^1$H NMR (400 MHz, (CD$_3$)$_2$SO): δ 2.95 (m, 1H), 3.25 (m, 1H), 4.05 (m, 1H), 4.35 (m, 1H), 4.45 (m, 1H), 7.05 (m, 1H), 7.20 (m, 1H).

Preparation 68: (S)-(6,7-Dihydro-5H-pyrrolo[1,2-a]imidazol-6-yl)amine hydrochloride

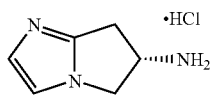

Using a procedure similar to that described for Preparation 67, but using (R)-6,7-dihydro-5H-pyrrolo[1,2-a]imidazol-6-ol. The title compound was prepared as a solid (32.65 g, 44%). $^1$H NMR (400 MHz, (CD$_3$)$_2$SO): δ 2.95 (m, 1H), 3.25 (m, 1H), 4.05 (m, 1H), 4.35 (m, 1H), 4.45 (m, 1H), 7.05 (m, 1H), 7.20 (m, 1H).

Preparation 69: 4-[Cyano(cyclopropyl)acetyl]benzonitrile

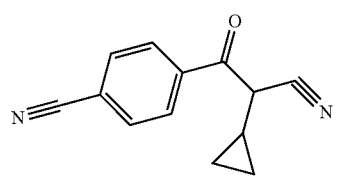

A 2.5 molar solution of n-butyl lithium (114 mL, 285 mmol) in hexane was added to a cooled (−78° C.) solution of diisopropylamine (38.3 mL, 273 mmol) in tetrahydrofuran (300 mL). This cooled reaction mixture was then allowed to stir for 1 hour, after which time cyclopropylacetonitrile (20.8 mL, 261 mmol) was added at such a rate as to keep the temperature below −60° C. This mixture was then allowed to stir at −78° C. for 1 hour, after which time a solution of 4-cyano-benzoic acid methyl ester (40 g, 248 mmol) in tetrahydrofuran (100 mL) was added at such a rate as to keep the temperature below −60° C. This mixture was then slowly warmed to room temperature and stirred for 18 hours after which time it was quenched onto an aqueous 10% solution (weight/volume) citric acid (600 mL) and extracted with ethyl acetate (2×2500 mL). The organic extracts were washed with brine (600 mL), dried over magnesium sulphate, filtered, and evaporated under reduced pressure to give a brown oil (52.7 g, 100%). This material was used for subsequent steps without further purification. $^1$H NMR (400 MHz, CDCl$_3$): δ 0.60 (m, 2H), 0.80 (m, 2H), 1.40 (m, 1H), 4.10 (d, 1H), 7.85 (d, 2H), 8.10 (d, 2H). ESCI MS m/z 243 [M−H]$^-$ Preparation 70: 4-(5-Amino-4-cyclopropyl-1-isopropyl-1H-pyrazol-3-yl)benzonitrile

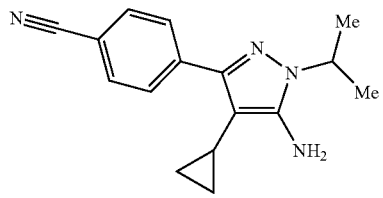

Isopropylhydrazine hydrochloride (31.4 g, 284 mmol) and diisopropylethylamine (90 mL, 517 mmol) were added to a solution of the compound described in Preparation 69 (54.3 g, 258 mmol) in ethanol (550 mL) followed by acetic acid (88.7 mL, 1550 mmol). This mixture was stirred at 60° C. for 16 hours. It was then cooled to room temperature and concentrated under reduced pressure. The crude material was partitioned between ethyl acetate (500 mL) and a saturated aqueous solution of sodium hydrogen carbonate (2×300 mL). The combined aqueous layers were extracted with ethyl acetate (500 mL). The combined organic extracts were dried over magnesium sulphate, filtered, and evaporated under reduced pressure to give a solid. This solid was triturated with tert-butyl methyl ether to give the title compound as a solid (53.41 g, 78%). $^1$H NMR (400 MHz, CDCl$_3$): δ 0.35 (m, 2H), 0.85 (m, 2H), 1.45 (d, 6H), 1.60 (m, 1H), 3.60 (m, 2H), 4.35 (m, 1H), 7.65 (d, 2H), 8.00 (d, 2H).

Preparation 71: 4-(4-Cyclopropyl-5-iodo-1-isopropyl-1H-pyrazol-3-yl)benzonitrile

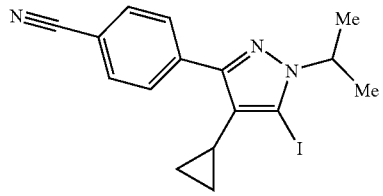

Acetic acid (48 mL, 845 mmol) was added to a cooled (0° C.) solution of the compound described in Preparation 70 (75 g, 282 mmol) in acetonitrile (1125 mL). This cooled solution was allowed to stir for 15 minutes after which time a solution of potassium iodide (117 g, 704 mmol) in water (375 mL) was added followed by a solution of tert-butyl nitrite (83.7 mL, 704 mmol) in acetonitrile (375 mL) over 15 minutes. This mixture was stirred at 0° C. for 10 minutes, then warmed to room temperature and allowed to stir for 16 hours. The resulting solid that precipitated out in the reaction mixture was filtered off. The cake obtained was made up into a suspension using a 10% w/w solution of sodium thiosulfate (200 mL). The suspension was stirred for 2 hours, filtered, rinsed with water (2×100 mL) and dried to afford the title compound as a pale brown solid (73.3 g, 69%). $^1$H NMR (400 MHz, CDCl$_3$): δ 0.40 (m, 2H), 0.95 (m, 2H), 1.50 (d, 6H), 1.70 (m, 1H), 4.70 (m, 1H), 7.65 (d, 2H), 7.95 (d, 2H).

Preparation 72: 3-(4-Cyanophenyl)-4-cyclopropyl-1-isopropyl-1H-pyrazole-5-carboxylic acid

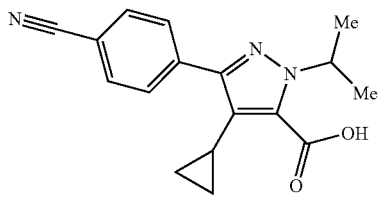

A 2.5 molar solution of n-butyl lithium (137 mL, 342 mmol) in hexane was added to a cooled (−78° C.) solution of the compound described in Preparation 71 (145 g, 340 mmol) in tetrahydrofuran (1450 mL). This mixture was stirred at −78° C. for 30 minutes, after which time carbon dioxide was bubbled through the solution for 1 hour. The reaction mixture was then quenched carefully with an aqueous 10% w/w solution of citric acid (900 mL). The organic layer was then collected and the aqueous layer was extracted with ethyl acetate (2×200 mL). The organic layers were combined and evaporated to dryness to afford an orange solid which was put in suspension in methyl tert-butyl ether (1000 mL) and extracted with an aqueous solution of sodium hydroxide (1.0 M, 1400 mL). The aqueous layer was then acidified with an aqueous solution of hydrochloric acid (2 M, 350 mL) to pH 5 to form a precipitate which was filtered off. The cake obtained was washed with water (100 mL) and dried to give the title compound as a pale brown solid (61 g, 60%). $^1$H NMR (400 MHz, CDCl$_3$): δ 0.30 (m, 2H), 0.95 (m, 2H), 1.50 (d, 6H), 1.90 (m, 1H), 5.40 (m, 1H), 7.65 (d, 2H), 7.95 (d, 2H).

Preparation 73: 4-Cyano-5-(4-cyano-3-methyl-phenyl)-2-isopropyl-2H-pyrazole-3-carboxylic acid

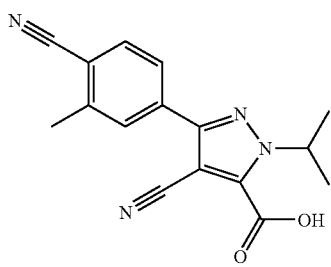

Using procedures similar to those described in Preparations 1, 2, 32, 33, 34, and 11 but using the compound described in Preparation 6, the title compound was prepared as a yellow solid (79 mg, 83%). $^1$H NMR (400 MHz, CDCl$_3$): δ 1.61 (d, 6H), 2.63 (s, 3H), 5.60 (m, 1H), 7.71 (d, 1H), 7.96-8.03 (m, 2H).

Preparation 74: (Z)-4-(4-Cyano-phenyl)-4-hydroxy-2-oxo-but-3-enoic acid tert-butyl ester

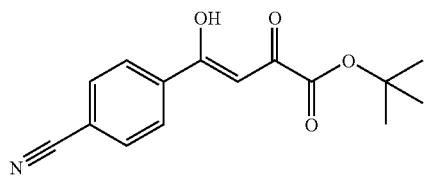

A solution of 4-acetylbenzonitrile (13.2 g, 90.9 mmol) in anhydrous tetrahydrofuran (100 mL) was cooled to −70° C. under nitrogen and sodium bis(trimethylsilyl)amide solution (1.0 M in THF, 100 mL, 100 mmol) added dropwise over 30 minutes. The solution was stirred at −70° C. for 1 hour before di-tert-butyl oxalate (22.1 g, 109 mmol) was added. The resulting suspension allowed to warm to room temperature and stir for 16 hours. The suspension was poured onto water (250 mL) containing ammonium chloride (53.5 g, 1.0 mol) and extracted with ethyl acetate (100 mL+50 mL). The organic layer was washed with water (100 mL) and concentrated under reduced pressure to afford a dark solid residue. The residue was triturated with diethyl ether (130 mL) and the residue filtered and dried under reduced pressure to give the title compound as a brown solid (7.13 g, 29%). $^1$H NMR (400 MHz, CDCl$_3$): δ 1.40 (9 H, s), 7.01 (1 H, br), 8.01-8.23 (4 H, m).

Preparation 75: 5-(4-Cyano-phenyl)-2H-pyrazole-3-carboxylic acid tert-butyl ester

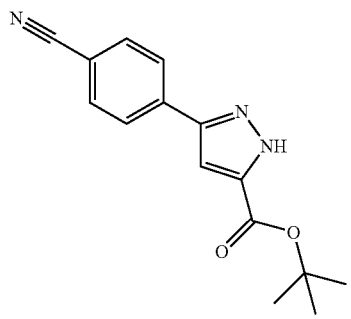

The compound described in Preparation 74 (7.08 g, 25.9 mmol) was suspended in acetonitrile (50 mL) and hydrazine monohydrate (64-65% w/w; 3.9 mL, 52 mmol) and acetic acid (4.5 mL, 4.7 g, 79 mmol) added. The resulting mixture was warmed to 80° C. and stirred for 3 hours. After cooling to room temperature, the mixture was concentrated under reduced pressure to give a yellow solid which was partitioned between ethyl acetate (100 mL) and water (100 mL). The organic layer was isolated and concentrated under reduced pressure to afford the title compound as a yellow solid (7.45 g, 27.7 mmol). $^1$H NMR (400 MHz, CDCl$_3$): δ 1.5 (9 H, s), 7.4 (1 H, s), 7.9 (2 H, m), 8.0 (2 H, m).

Preparation 76: 5-(4-Cyano-phenyl)-2-isopropyl-2H-pyrazole-3-carboxylic acid tert-butyl ester

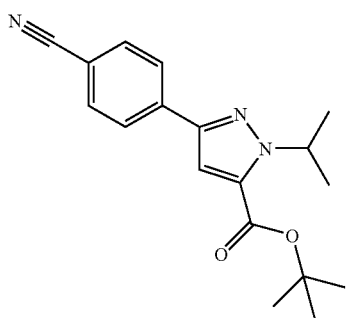

Potassium carbonate (16.1 g, 117 mmol) and 2-iodo-propane (8.73 mL, 87.4 mmol) were added to a solution of the compound described in Preparation 75 (15.7 g, 58.3 mmol) in acetonitrile (200 mL). The resulting mixture was stirred at reflux for 3 hours. The reaction mixture was then partitioned between ethyl acetate (300 mL) and water (300 mL). The aqueous layer was further extracted with ethyl acetate (2×200 mL) and the combined organics washed with brine (200 mL), dried over magnesium sulphate and concentrated under reduced pressure to afford an off-white solid. The crude material was purified by silica-gel column chromatography (eluting with 20% ethyl acetate in pentane) to afford the title compound as a white solid (16.3 g, 90%). $^1$H NMR (400 MHz, CDCl$_3$): δ 1.55 (d, 6H), 1.60 (s, 9H), 5.55 (m, 1H), 7.05 (s, 1H), 7.65 (d, 2H), 7.90 (d, 2H).

Preparation 77: 4-Chloro-5-(4-cyano-phenyl)-2-isopropyl-2H-pyrazole-3-carboxylic acid tert-butyl ester

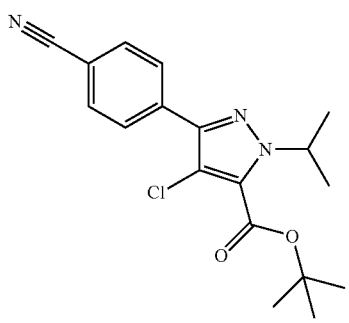

A solution of the compound described in Preparation 76 (1.62 g, 5.2 mmol) in acetonitrile (25 mL) was treated with N-chlorosuccinimide (1.39 g, 10.4 mmol) and trifluoroacetic acid (1.31 g, 11.5 mmol). The resulting mixture was stirred at room temperature for 18 hours and then concentrated under reduced pressure. The resultant pink residue was partitioned between ethyl acetate (100 mL) and 10% w/w aqueous solution of sodium metabisulfite (100 mL). The organic layer was washed with water (50 mL) and concentrated under reduced pressure. The crude material was purified by silica-gel column chromatography (eluting with 10% ethyl acetate in heptane) to afford the title compound as a white solid (772 mg, 2.23 mmol, 43%). $^1$H NMR (400 MHz, CDCl$_3$): δ 1.46 (d, 9H), 5.29 (m, 1H), 7.95 (d, 2H), 8.05 (d, 2H).

Preparation 78: 4-Chloro-5-(4-cyano-phenyl)-2-isopropyl-2H-pyrazole-3-carboxylic acid

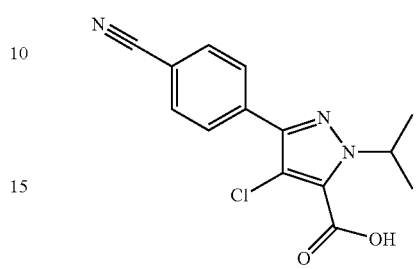

Trifluoroacetic acid (1.7 mL, 23 mmol) was added to a solution of the compound described in Preparation 77 (768 mg, 2.22 mmol) in tetrahydrofuran (6 mL). The resulting mixture was stirred at 70° C. for 70 hours. After cooling, the mixture was concentrated under reduced pressure and the residue partitioned between 1M aqueous sodium hydroxide (10 mL) and ethyl acetate (10 mL). The aqueous phase was neutralised to pH7 using 2M aqueous hydrogen chloride and extracted with ethyl acetate (3×10 mL). The combined organics were dried over magnesium sulphate and concentrated under reduced pressure to afford the title compound as a white solid (284 mg, 0.98 mmol, 44%). $^1$H NMR (400 MHz, d$_6$-DMSO): δ 1.4 (6 H, d), 5.4 (1 H, dq), 7.9 (2 H, m), 8.0 (2 H, m).

All of the above reactions and the preparations of novel starting materials used in the preceding methods are conventional and appropriate reaction conditions for their performance or preparation as well as procedures for isolating the desired products will be well-known to those skilled in the art with reference to literature precedents and the Examples and Preparations herein.

Biological Data

Progesterone receptor antagonist (PRA) K$_i$ values were determined for the compounds of the Examples using the in vitro functional assay for the progesterone receptor as described at 1.0 above:

| Ex No | PR Ki (nM) |
|---|---|
| 1 | 19.8 |
| 2 | 9.39 |
| 3 | 13.9 |
| 4 | 7.06 |
| 5 | 7.92 |
| 6 | 145 |
| 7 | 9.73 |
| 8 | 162 |
| 9 | 836 |
| 10 | 285 |
| 11 | 18.6 |
| 12 | 17.2 |
| 13 | 34.8 |
| 14 | 302 |
| 15 | 280 |
| 16 | 42.8 |
| 17 | 42.2 |
| 18 | 38.2 |
| 19 | 51.4 |
| 20 | 3.78 |

| Ex No | PR Ki (nM) | | |
|---|---|---|---|
| 21 | 8.27 | | |
| 22 | 6.67 | | |
| 23 | 10.2 | | |
| 24 | 19.4 | | |
| 25 | 24.5 | | |
| 26 | 86.1 | | |
| 27 | 161 | | |
| 28 | 171 | | |
| 29 | 235 | | |
| 30 | 30.9 | | |
| 31 | 36.3 | | |
| 32 | 34.6 | | |
| 33 | 7.11 | | |
| 34 | 18.9 | | |
| 35 | 11.2 | | |
| 36 | 12 | | |
| 37 | 13.4 | | |
| 38 | >57.2 | | |
| 39 | 17.8 | | |
| 40 | 17.5 | | |
| 41 | 25 | | |
| 42 | 27.3 | | |
| 43 | 26 | | |
| 44 | 40.8 | | |
| 45 | 104 | | |
| 46 | >2010 | | |
| 47 | — | | |
| 48 | 5.27 | | |
| 49 | 4.94 | | |
| 50 | 3.59 | | |
| 51 | 4.65 | | |
| 52 | 5.7 | | |
| 53 | 7.38 | | |
| 54 | 8.45 | | |
| 55 | 13.8 | | |
| 56 | 82.6 | | |
| 57 | 7.43 | | |
| 58 | 6.87 | | |
| 59 | 7.84 | | |
| 60 | 42.1 | | |
| 61 | 8.29 | | |
| 62 | 3.09 | | |
| 63 | 6.24 | | |
| 64 | 10.9 | | |
| 65 | 3.55 | | |
| 66 | 3.56 | | |
| 67 | 4.4 | | |
| 68 | 6.38 | | |
| 69 | 3.4 | | |
| 70 | 5.51 | | |
| 71 | 8.25 | | |
| 72 | 13.3 | | |
| 73 | 29.1 | | |
| 74 | 18.5 | | |
| 75 | — | | |
| 76 | Rac | 26.9 | |
| | Ent 1 | 22.3 | |
| | Ent 2 | 147 | |
| 77 | Rac | 28.2 | |
| | Ent 1 | 69.5 | |
| | Ent 2 | 102 | |
| 78 | Mix | 71.6 | |
| | Diast 1 | >242 | |
| | Diast 2 | 49.4 | |
| 79 | Mix | — | |
| | Diast 1 | >766 | |
| | Diast 2 | 163 | |
| 80 | Rac | 138 | |
| | Ent 1 | 57.1 | |
| | Ent 2 | >733 | |
| 81 | 61.2 | | |
| 82 | 70.2 | | |
| 83 | 96.5 | | |
| 84 | 125 | | |
| 85 | 139 | | |
| 86 | >137 | | |
| 87 | >191 | | |
| 88 | — | | |
| 89 | 7.75 | | |
| 90 | — | | |
| 91 | 6.48 | | |
| 92 | 8.84 | | |
| 93 | — | | |
| 94 | 10.6 | | |
| 95 | 315 | | |
| 96 | 374 | | |
| 97 | 399 | | |
| 98 | 208 | | |
| 99 | 52.5 | | |
| 100 | 151 | | |
| 101 | 7.67 | | |
| 102 | 14.7 | | |
| 103 | 12.7 | | |
| 104 | 17.8 | | |
| 105 | 14.2 | | |
| 106 | Rac | 23.8 | |
| | Ent 1 | 14.8 | |
| | Ent 2 | 38.2 | |
| 107 | 63 | | |
| 108 | 91.4 | | |
| 109 | Rac 1 | 199 | |
| | Ent 1 | 99 | |
| | Ent 2 | 190 | |
| 110 | 8.24 | | |
| 111 | 23.1 | | |
| 112 | 26 | | |
| 113 | 27.1 | | |
| 114 | 30.9 | | |
| 115 | 85 | | |
| 116 | 32.1 | | |
| 117 | 36.4 | | |
| 118 | 54.8 | | |
| 119 | >145 | | |
| 120 | 8.66 | | |
| 121 | 5.06 | | |
| 122 | 5.18 | | |
| 123 | 5.49 | | |
| 124 | 5.93 | | |
| 125 | 8.28 | | |
| 126 | 10.2 | | |
| 127 | 11.3 | | |
| 128 | 11.9 | | |
| 129 | 13.2 | | |
| 130 | 14.8 | | |
| 131 | 17.2 | | |
| 132 | 17.8 | | |
| 133 | 19.3 | | |
| 134 | 21.9 | | |

The invention claimed is:

1. A compound of Formula (I):

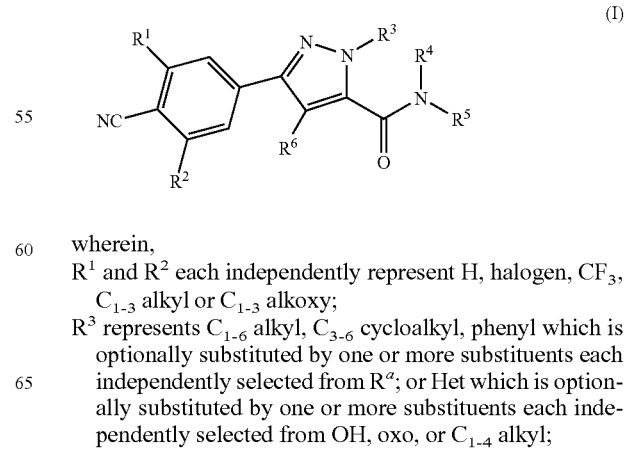

wherein, $R^1$ and $R^2$ each independently represent H, halogen, $CF_3$, $C_{1-3}$ alkyl or $C_{1-3}$ alkoxy;

$R^3$ represents $C_{1-6}$ alkyl, $C_{3-6}$ cycloalkyl, phenyl which is optionally substituted by one or more substituents each independently selected from $R^a$; or Het which is optionally substituted by one or more substituents each independently selected from OH, oxo, or $C_{1-4}$ alkyl;

$R^a$ represents halogen, $CF_3$, or CN;

Het represents a 5- or 6- membered, saturated, partially saturated, or aromatic, heterocyclic ring comprising (a) from 1 to 4 nitrogen atoms, or (b) 1 or 2 nitrogen atoms and 1 oxygen atom or 1 sulphur atom, or (c) 1 oxygen atom or 1 sulphur atom;

$R^4$ represents H or $C_{1-3}$ alkyl;

$R^5$ represents $Het^2$ which is optionally substituted by one or more substituents each independently selected from $R^d$; where $Het^2$ represents a 4- to 6-membered, saturated, partially saturated, or aromatic, monocyclic heterocyclic ring, or a 7- to 12-membered saturated, partially saturated, or aromatic, bicyclic heterocyclic ring, comprising (a) from 1 to 4 nitrogen atoms, or (b) 1 or 2 nitrogen atoms and 1 oxygen atom or 1 sulphur atom, or (c) 1 oxygen atom or 1 sulphur atom; and $R^d$ represents $C_{1-4}$ alkyl, oxo, OH, $COC_{1-4}$ alkyl, $COOC_{1-4}$ alkyl, $SO_2C_{1-4}$ alkyl, $NH_2$, $CONHC_{1-4}$ alkyl, or $CON(C_{1-4}$ alkyl$)_2$; and $R^6$ represents $C_{1-3}$ alkyl which is optionally substituted by one or more substituents each independently selected from $R^f$; $C_{3-5}$ cycloalkyl which is optionally substituted by one or more halogen; CN or halogen; where $R^f$ represents halogen or phenyl; or a pharmaceutically acceptable salt or solvate thereof.

2. A compound according to claim 1, wherein $R^1$ represents H or $C_{1-3}$ alkyl; or a pharmaceutically acceptable salt or solvate thereof.

3. A compound according to claim 1 wherein $R^1$ represents H or methyl; or a pharmaceutically acceptable salt or solvate thereof.

4. A compound according to claim 1, wherein $R^2$ represents H; or a pharmaceutically acceptable salt or solvate thereof.

5. A compound according to claim 1, wherein $R^3$ represents $C_{1-6}$ alkyl, $C_{3-6}$ cycloalkyl, or Het; or a pharmaceutically acceptable salt or solvate thereof.

6. A compound according to claim 1 wherein $R^3$ is isopropyl, butan-2-yl, cyclopropyl, cyclobutyl or 3-tetrahydrofuranyl; or a pharmaceutically acceptable salt or solvate thereof.

7. A compound according to claim 1 wherein $R^3$ is isopropyl, cyclobutyl or butan-2-yl; or a pharmaceutically acceptable salt or solvate thereof.

8. A compound according to claim 1 wherein $R^4$ is H or methyl; or a pharmaceutically acceptable salt or solvate thereof.

9. A compound according to claim 1 wherein $R^4$ is H; or a pharmaceutically acceptable salt or solvate thereof.

10. A compound according to claim 1 wherein $R^5$ is $Het^2$ and represents a 4- to 6-membered saturated monocyclic heterocyclic ring, comprising (a) from 1 to 4 nitrogen atoms, or (b) 1 or 2 nitrogen atoms and 1 oxygen atom or 1 sulphur atom, or (c) 1 oxygen atom or 1 sulphur atom; and which is optionally substituted with one to three $R^d$; or a pharmaceutically acceptable salt or solvate thereof.

11. A compound according to claim 1 wherein $R^5$ is tetrahydrofuran-2-ylmethyl, 1-t-butoxycarbonylpyrrolidin-3-yl, 1-t-butoxycarbonylazetidin3-yl, pyrrolidin-3-yl, azetidin-3-yl, 1-isopropylcarbonylpyrrolidin-3-yl, 1-ethylcarbonylpyrrolidin-3-yl, 1-methanesulphonylpyrrolidin-3-yl, 1-isopropylcarbonylazetidin-3-yl, 1-ethylcarbonylazetidin-3-yl, 1-methanesulphonylazetidin-3-yl, 1-acetylazetidin-3-yl, 2-oxotetrahydrofuran-3-yl, 6,7-dihydro-5H-pyrrolo[1,2-a]imidazol-6-yl, tetrahydro-2H-pyran-3-yl, tetrahydro-2H-pyran-4-yl, 1-methyl-6-oxopiperidin-3-yl, 5-oxopyrrolidin-3-yl, tetrahydrofuran-3-yl, 1,1-dioxidotetrahydro-3-thienyl; or a pharmaceutically acceptable salt or solvate thereof.

12. A compound according to claim 1 wherein $R^6$ represents $C_{1-3}$ alkyl which is optionally substituted by one or more phenyl substituents; $C_{3-5}$ cycloalkyl which is optionally substituted by one or more halogen; CN or halogen; or a pharmaceutically acceptable salt or solvate thereof.

13. A compound according to claim 1 wherein $R^6$ is methyl, ethyl, cyclopropyl, 3,3-difluorocyclobutyl, benzyl, cyano or chloro; or a pharmaceutically acceptable salt or solvate thereof.

14. A compound according to claim 1 wherein $R^6$ is methyl, cyclopropyl, cyano or chloro; or a pharmaceutically acceptable salt or solvate thereof.

15. A compound as claimed in claim 1 of Formula (Ia):

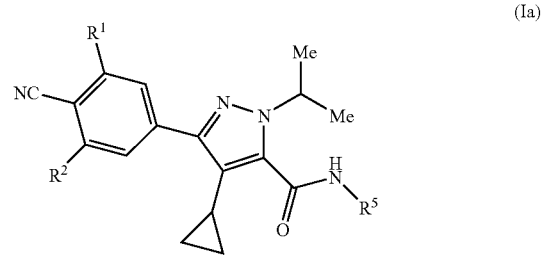

(Ia)

wherein $R^1$, $R^2$ and $R^5$ are as defined in claim 1; or a pharmaceutically acceptable salt or solvate thereof.

16. A compound of the formula (Ia) as claimed in claim 15 wherein $R^1$ and $R^2$ are both H; or a pharmaceutically acceptable salt or solvate thereof.

17. A compound selected from:

tert-butyl (3R)-3-({[3-(4-cyanophenyl)-4-cyclopropyl-1-isopropyl-1H-pyrazol-5-yl]carbonyl}amino)pyrrolidine-1-carboxylate;

tert-butyl (3S)-3-({[3-(4-cyanophenyl)-4-cyclopropyl-1-isopropyl-1H-pyrazol-5-yl]carbonyl}amino)pyrrolidine-1-carboxylate;

tert-butyl 3-({[3-(4-cyanophenyl)-4-cyclopropyl-1-isopropyl-1H-pyrazol-5-yl]carbonyl}amino)azetidine-1-carboxylate;

3-(4-cyanophenyl)-4-cyclopropyl-1-isopropyl-N-[(3R)-pyrrolidin-3-yl]-1H-pyrazole-5-carboxamide;

3-(4-cyanophenyl)-4-cyclopropyl-1-isopropyl-N-[(3S)-pyrrolidin-3-yl]-1H-pyrazole-5-carboxamide;

N-azetidin-3-yl-3-(4-cyanophenyl)-4-cyclopropyl-1-isopropyl-1H-pyrazole-5-carboxamide;

3-(4-cyanophenyl)-4-cyclopropyl-N-[(3R)-1-isobutyrylpyrrolidin-3-yl]-1-isopropyl-1H-pyrazole-5-carboxamide;

3-(4-cyanophenyl)-4-cyclopropyl-1-isopropyl-N-[(3R)-1-(methylsulfonyl)pyrrolidin-3-yl]-1H-pyrazole-5-carboxamide;

3-(4-cyanophenyl)-4-cyclopropyl-N-[(3S)-1-isobutyrylpyrrolidin-3-yl]-1-isopropyl-1H-pyrazole-5-carboxamide;

3-(4-cyanophenyl)-4-cyclopropyl-1-isopropyl-N-[(3S)-1-propionylpyrrolidin-3-yl]-1H-pyrazole-5-carboxamide;

3-(4-cyanophenyl)-4-cyclopropyl-N-(1-isobutyrylazetidin-3-yl)-1-isopropyl-1H-pyrazole-5-carboxamide;

3-(4-cyanophenyl)-4-cyclopropyl-1-isopropyl-N-(1-propionylazetidin-3-yl)-1H-pyrazole-5-carboxamide;

3-(4-cyanophenyl)-4-cyclopropyl-1-isopropyl-N-[1-(methylsulfonyl)azetidin-3-yl]-1H-pyrazole-5-carboxamide;

N-(1-acetylazetidin-3-yl)-3-(4-cyanophenyl)-4-cyclopropyl-1-isopropyl-1H-pyrazole-5-carboxamide;

3-(4-cyanophenyl)-4-cyclopropyl-1-isopropyl-N-[(3S)-2-oxotetrahydrofuran-3-yl]-1H-pyrazole-5-carboxamide;

3-(4-cyanophenyl)-4-cyclopropyl-N-[(6S)-6,7-dihydro-5H-pyrrolo[1,2-a]imidazol-6-yl]-1-isopropyl-1H-pyrazole-5-carboxamide;

3-(4-cyanophenyl)-4-cyclopropyl-N-[(6R)-6,7-dihydro-5H-pyrrolo[1,2-a]imidazol-6-yl]-1-isopropyl-1H-pyrazole-5-carboxamide;

3-(4-cyanophenyl)-4-cyclopropyl-1-isopropyl-N-(tetrahydro-2H-pyran-3-yl)-1H-pyrazole-5-carboxamide;

3-(4-cyanophenyl)-4-cyclopropyl-1-isopropyl-N-(1-methyl-6-oxopiperidin-3-yl)-1H-pyrazole-5-carboxamide;

3-(4-cyanophenyl)-4-cyclopropyl-1-isopropyl-N-(tetrahydro-2H-pyran-4-yl)-1H-pyrazole-5-carboxamide;

3-(4-cyanophenyl)-4-cyclopropyl-1-isopropyl-N-[(3R)-5-oxopyrrolidin-3-yl]-1H-pyrazole-5-carboxamide;

3-(4-cyanophenyl)-4-cyclopropyl-1-isopropyl-N-(tetrahydrofuran-3-yl)-1H-pyrazole-5-carboxamide; and 3-(4-cyanophenyl)-4-cyclopropyl-N-(1,1-dioxidotetrahydro-3-thienyl)-1-isopropyl-1H-pyrazole-5-carboxamide;

and the pharmaceutically acceptable salts and solvates thereof.

18. A pharmaceutical composition comprising a compound according to claim 1; or a pharmaceutically acceptable salt or solvate thereof, and a pharmaceutically acceptable excipient, diluent, carrier or adjuvant.

19. A method of treating endometriosis, uterine fibroids, menorrhagia, adenomyosis, primary dysmenorrhoea, secondary dysmenorrhoea, chronic pelvic pain syndrome, breast cancer, ovarian cancer or endometrial cancer in a mammal, the method comprising administering to a mammal in need of treatment thereof a therapeutically effective amount of a pharmaceutical composition according to claim 18.

20. A method of treating endometriosis, uterine fibroids, menorrhagia, adenomyosis, primary dysmenorrhoea, secondary dysmenorrhoea, chronic pelvic pain syndrome, breast cancer, ovarian cancer or endometrial cancer in a mammal, the method comprising administering to a mammal in need of treatment thereof a therapeutically effective amount of a compound according to claim 1, or a pharmaceutically acceptable salt or solvate thereof.

21. A combination of a compound according to claim 1, or a pharmaceutically acceptable salt or solvate thereof, and another therapeutically active entity.

22. The compound 3-(4-cyanophenyl)-4-cyclopropyl-N-(1,1-dioxidotetrahydro-3-thienyl)-1-isopropyl-1H-pyrazole-5-carboxamide; or pharmaceutically acceptable salts and solvates thereof.

23. A pharmaceutical composition comprising 3-(4-cyanophenyl)-4-cyclopropyl-N-(1,1-dioxidotetrahydro-3-thienyl)-1-isopropyl-1H-pyrazole-5-carboxamide; or pharmaceutically acceptable salts and solvates thereof, and one or more pharmaceutically acceptable excipients, diluents, carriers or adjuvants.

* * * * *